United States Patent
Langlade-Demoyen et al.

(10) Patent No.: US 8,003,773 B2
(45) Date of Patent: Aug. 23, 2011

(54) POLYNUCLEOTIDES ENCODING MHC CLASS I-RESTRICTED HTERT EPITOPES, ANALOGUES THEREOF OR POLYEPITOPES

(75) Inventors: Pierre Langlade-Demoyen, Paris (FR); Fransisco Garcia Pons, Maurepas (FR); Olivier Adotevi, Nogent sur Marne (FR); Sylvain Cardinaud, Carrieres sur Seine (FR); Christine Neuveut, Arcueil (FR); Kostas Kosmatopoulos, Paris (FR); Stéphanie Graff-Dubois, Paris (FR); Jeanne Menez-Jamet, Montrouge (FR)

(73) Assignees: Institut Pasteur, Paris (FR); INSERM, Paris (FR)

( * ) Notice: Subject to any disclaimer, the term of this patent is extended or adjusted under 35 U.S.C. 154(b) by 704 days.

(21) Appl. No.: 11/826,134

(22) Filed: Jul. 12, 2007

(65) Prior Publication Data

US 2009/0175892 A1    Jul. 9, 2009

Related U.S. Application Data

(63) Continuation-in-part of application No. 11/795,027, filed as application No. PCT/EP2006/007571 on Jul. 31, 2006.

(30) Foreign Application Priority Data

Jul. 29, 2005   (EP) .................................... 05291627

(51) Int. Cl.
*C07H 21/02* (2006.01)
*C07H 21/04* (2006.01)
*C12N 15/63* (2006.01)
*C12N 15/85* (2006.01)
*C12N 15/86* (2006.01)

(52) U.S. Cl. ..................... 536/23.2; 435/325; 435/320.1

(58) Field of Classification Search ................ 536/23.2; 435/325, 320.1
See application file for complete search history.

*Primary Examiner* — Thaian N Ton
*Assistant Examiner* — Magdalene Sgagias
(74) *Attorney, Agent, or Firm* — Finnegan, Henderson, Farabow, Garrett & Dunner LLP

(57) ABSTRACT

This invention relates to the field of anticancer therapy, and to the identification of immunogenic peptides derived from the human telomerase reverse transcriptase (hTERT). The present invention relates to polynucleotides encoding hTERT epitopes restricted to MHC class I molecule, analogues thereof and polyepitopes containing such epitopes and/or analogues. Are also included in the present invention, vector and cell comprising such polynucleotides. The present invention also concerns composition comprising hTERT polypeptides, corresponding polynucleotides, vectors and cells, for use in the treatment and/or prevention of cancer.

12 Claims, 27 Drawing Sheets

```
gcagcgctgc gtcctgctgc gcacgtggga agccctggcc ccggccaccc ccgcg atg    58
                                                              Met
                                                                1 ccg cgc gct ccc cgc tgc cga gcc gtg cgc tcc ctg ctg cgc agc cac    106
Pro Arg Ala Pro Arg Cys Arg Ala Val Arg Ser Leu Leu Arg Ser His
              5                  10                  15 tac cgc gag gtg ctg ccg ctg gcc acg ttc gtg cgg cgc ctg ggg ccc    154
Tyr Arg Glu Val Leu Pro Leu Ala Thr Phe Val Arg Arg Leu Gly Pro
          20                  25                  30 cag ggc tgg cgg ctg gtg cag cgc ggg gac ccg gcg gct ttc cgc gcg    202
Gln Gly Trp Arg Leu Val Gln Arg Gly Asp Pro Ala Ala Phe Arg Ala
      35                  40                  45 ctg gtg gcc cag tgc ctg gtg tgc gtg ccc tgg gac gca cgg ccg ccc    250
Leu Val Ala Gln Cys Leu Val Cys Val Pro Trp Asp Ala Arg Pro Pro
 50                  55                  60                  65 ccc gcc gcc ccc tcc ttc cgc cag gtg tcc tgc ctg aag gag ctg gtg    298
Pro Ala Ala Pro Ser Phe Arg Gln Val Ser Cys Leu Lys Glu Leu Val
                  70                  75                  80 gcc cga gtg ctg cag agg ctg tgc gag cgc ggc gcg aag aac gtg ctg    346
Ala Arg Val Leu Gln Arg Leu Cys Glu Arg Gly Ala Lys Asn Val Leu
              85                  90                  95 gcc ttc ggc ttc gcg ctg ctg gac ggg gcc cgc ggg ggc ccc ccc gag    394
Ala Phe Gly Phe Ala Leu Leu Asp Gly Ala Arg Gly Gly Pro Pro Glu
          100                 105                 110 gcc ttc acc acc agc gtg cgc agc tac ctg ccc aac acg gtg acc gac    442
Ala Phe Thr Thr Ser Val Arg Ser Tyr Leu Pro Asn Thr Val Thr Asp
      115                 120                 125 gca ctg cgg ggg agc ggg gcg tgg ggg ctg ctg ctg cgc cgc gtg ggc    490
Ala Leu Arg Gly Ser Gly Ala Trp Gly Leu Leu Leu Arg Arg Val Gly
130                 135                 140                 145 gac gac gtg ctg gtt cac ctg ctg gca cgc tgc gcg ctc ttt gtg ctg    538
Asp Asp Val Leu Val His Leu Leu Ala Arg Cys Ala Leu Phe Val Leu
                  150                 155                 160 gtg gct ccc agc tgc gcc tac cag gtg tgc ggg ccg ccg ctg tac cag    586
Val Ala Pro Ser Cys Ala Tyr Gln Val Cys Gly Pro Pro Leu Tyr Gln
              165                 170                 175 ctc ggc gct gcc act cag gcc cgg ccc ccg cca cac gct agt gga ccc    634
Leu Gly Ala Ala Thr Gln Ala Arg Pro Pro Pro His Ala Ser Gly Pro
          180                 185                 190 cga agg cgt ctg gga tgc gaa cgg gcc tgg aac cat agc gtc agg gag    682
Arg Arg Arg Leu Gly Cys Glu Arg Ala Trp Asn His Ser Val Arg Glu
      195                 200                 205
```

Figure 1A

| | | |
|---|---|---|
| gcc ggg gtc ccc ctg ggc ctg cca gcc ccg ggt gcg agg agg cgc ggg<br>Ala Gly Val Pro Leu Gly Leu Pro Ala Pro Gly Ala Arg Arg Arg Gly<br>210                   215                   220                 225 | 730 |
| ggc agt gcc agc cga agt ctg ccg ttg ccc aag agg ccc agg cgt ggc<br>Gly Ser Ala Ser Arg Ser Leu Pro Leu Pro Lys Arg Pro Arg Arg Gly<br>                  230                   235                   240 | 778 |
| gct gcc cct gag ccg gag cgg acg ccc gtt ggg cag ggg tcc tgg gcc<br>Ala Ala Pro Glu Pro Glu Arg Thr Pro Val Gly Gln Gly Ser Trp Ala<br>               245                   250                 255 | 826 |
| cac ccg ggc agg acg cgt gga ccg agt gac cgt ggt ttc tgt gtg gtg<br>His Pro Gly Arg Thr Arg Gly Pro Ser Asp Arg Gly Phe Cys Val Val<br>            260                   265                   270 | 874 |
| tca cct gcc aga ccc gcc gaa gaa gcc acc tct ttg gag ggt gcg ctc<br>Ser Pro Ala Arg Pro Ala Glu Glu Ala Thr Ser Leu Glu Gly Ala Leu<br>275                   280                   285 | 922 |
| tct ggc acg cgc cac tcc cac cca tcc gtg ggc cgc cag cac cac gcg<br>Ser Gly Thr Arg His Ser His Pro Ser Val Gly Arg Gln His His Ala<br>290                   295                   300                 305 | 970 |
| ggc ccc cca tcc aca tcg cgg cca cca cgt ccc tgg gac acg cct tgt<br>Gly Pro Pro Ser Thr Ser Arg Pro Pro Arg Pro Trp Asp Thr Pro Cys<br>                   310                   315                 320 | 1018 |
| ccc ccg gtg tac gcc gag acc aag cac ttc ctc tac tcc tca ggc gac<br>Pro Pro Val Tyr Ala Glu Thr Lys His Phe Leu Tyr Ser Ser Gly Asp<br>               325                   330                 335 | 1066 |
| aag gag cag ctg cgg ccc tcc ttc cta ctc agc tct ctg agg ccc agc<br>Lys Glu Gln Leu Arg Pro Ser Phe Leu Leu Ser Ser Leu Arg Pro Ser<br>            340                   345                   350 | 1114 |
| ctg act ggc gct cgg agg ctc gtg gag acc atc ttt ctg ggt tcc agg<br>Leu Thr Gly Ala Arg Arg Leu Val Glu Thr Ile Phe Leu Gly Ser Arg<br>355                   360                   365 | 1162 |
| ccc tgg atg cca ggg act ccc cgc agg ttg ccc cgc ctg ccc cag cgc<br>Pro Trp Met Pro Gly Thr Pro Arg Arg Leu Pro Arg Leu Pro Gln Arg<br>370                   375                   380                 385 | 1210 |
| tac tgg caa atg cgg ccc ctg ttt ctg gag ctg ctt ggg aac cac gcg<br>Tyr Trp Gln Met Arg Pro Leu Phe Leu Glu Leu Leu Gly Asn His Ala<br>                   390                   395                 400 | 1258 |
| cag tgc ccc tac ggg gtg ctc ctc aag acg cac tgc ccg ctg cga gct<br>Gln Cys Pro Tyr Gly Val Leu Leu Lys Thr His Cys Pro Leu Arg Ala<br>               405                   410                 415 | 1306 |
| gcg gtc acc cca gca gcc ggt gtc tgt gcc cgg gag aag ccc cag ggc<br>Ala Val Thr Pro Ala Ala Gly Val Cys Ala Arg Glu Lys Pro Gln Gly<br>            420                   425                   430 | 1354 |

Figure 1B

```
tct gtg gcg gcc ccc gag gag gag gac aca gac ccc cgt cgc ctg gtg    1402
Ser Val Ala Ala Pro Glu Glu Glu Asp Thr Asp Pro Arg Arg Leu Val
    435             440                 445 cag ctg ctc cgc cag cac agc agc ccc tgg cag gtg tac ggc ttc gtg    1450
Gln Leu Leu Arg Gln His Ser Ser Pro Trp Gln Val Tyr Gly Phe Val
450             455                 460                 465 cgg gcc tgc ctg cgc cgg ctg gtg ccc cca ggc ctc tgg ggc tcc agg    1498
Arg Ala Cys Leu Arg Arg Leu Val Pro Pro Gly Leu Trp Gly Ser Arg
                470                 475                 480 cac aac gaa cgc cgc ttc ctc agg aac acc aag aag ttc atc tcc ctg    1546
His Asn Glu Arg Arg Phe Leu Arg Asn Thr Lys Lys Phe Ile Ser Leu
            485                 490                 495 ggg aag cat gcc aag ctc tcg ctg cag gag ctg acg tgg aag atg agc    1594
Gly Lys His Ala Lys Leu Ser Leu Gln Glu Leu Thr Trp Lys Met Ser
        500                 505                 510 gtg cgg gac tgc gct tgg ctg cgc agg agc cca ggg gtt ggc tgt gtt    1642
Val Arg Asp Cys Ala Trp Leu Arg Arg Ser Pro Gly Val Gly Cys Val
    515                 520                 525 ccg gcc gca gag cac cgt ctg cgt gag gag atc ctg gcc aag ttc ctg    1690
Pro Ala Ala Glu His Arg Leu Arg Glu Glu Ile Leu Ala Lys Phe Leu
530             535                 540                 545 cac tgg ctg atg agt gtg tac gtc gtc gag ctg ctc agg tct ttc ttt    1738
His Trp Leu Met Ser Val Tyr Val Val Glu Leu Leu Arg Ser Phe Phe
                550                 555                 560 tat gtc acg gag acc acg ttt caa aag aac agg ctc ttt ttc tac cgg    1786
Tyr Val Thr Glu Thr Thr Phe Gln Lys Asn Arg Leu Phe Phe Tyr Arg
            565                 570                 575 aag agt gtc tgg agc aag ttg caa agc att gga atc aga cag cac ttg    1834
Lys Ser Val Trp Ser Lys Leu Gln Ser Ile Gly Ile Arg Gln His Leu
        580                 585                 590 aag agg gtg cag ctg cgg gag ctg tcg gaa gca gag gtc agg cag cat    1882
Lys Arg Val Gln Leu Arg Glu Leu Ser Glu Ala Glu Val Arg Gln His
    595                 600                 605 cgg gaa gcc agg ccc gcc ctg ctg acg tcc aga ctc cgc ttc atc ccc    1930
Arg Glu Ala Arg Pro Ala Leu Leu Thr Ser Arg Leu Arg Phe Ile Pro
610             615                 620                 625 aag cct gac ggg ctg cgg ccg att gtg aac atg gac tac gtc gtg gga    1978
Lys Pro Asp Gly Leu Arg Pro Ile Val Asn Met Asp Tyr Val Val Gly
                630                 635                 640 gcc aga acg ttc cgc aga gaa aag agg gcc gag cgt ctc acc tcg agg    2026
Ala Arg Thr Phe Arg Arg Glu Lys Arg Ala Glu Arg Leu Thr Ser Arg
            645                 650                 655
```

Figure 1C

```
gtg aag gca ctg ttc agc gtg ctc aac tac gag cgg gcg cgg cgc ccc    2074
Val Lys Ala Leu Phe Ser Val Leu Asn Tyr Glu Arg Ala Arg Arg Pro
        660                 665                 670 ggc ctc ctg ggc gcc tct gtg ctg ggc ctg gac gat atc cac agg gcc    2122
Gly Leu Leu Gly Ala Ser Val Leu Gly Leu Asp Asp Ile His Arg Ala
675                 680                 685 tgg cgc acc ttc gtg ctg cgt gtg cgg gcc cag gac ccg ccg cct gag    2170
Trp Arg Thr Phe Val Leu Arg Val Arg Ala Gln Asp Pro Pro Pro Glu
690                 695                 700                 705 ctg tac ttt gtc aag gtg gat gtg acg ggc gcg tac gac acc atc ccc    2218
Leu Tyr Phe Val Lys Val Asp Val Thr Gly Ala Tyr Asp Thr Ile Pro
        710                 715                 720 cag gac agg ctc acg gag gtc atc gcc agc atc atc aaa ccc cag aac    2266
Gln Asp Arg Leu Thr Glu Val Ile Ala Ser Ile Ile Lys Pro Gln Asn
            725                 730                 735 acg tac tgc gtg cgt cgg tat gcc gtg gtc cag aag gcc gcc cat ggg    2314
Thr Tyr Cys Val Arg Arg Tyr Ala Val Val Gln Lys Ala Ala His Gly
            740                 745                 750 cac gtc cgc aag gcc ttc aag agc cac gtc tct acc ttg aca gac ctc    2362
His Val Arg Lys Ala Phe Lys Ser His Val Ser Thr Leu Thr Asp Leu
755                 760                 765 cag ccg tac atg cga cag ttc gtg gct cac ctg cag gag acc agc ccg    2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc    2458
Leu Arg Asp Ala Val Val Ile Glu Gln Ser Ser Ser Leu Asn Glu Ala
                790                 795                 800 agc agt ggc ctc ttc gac gtc ttc cta cgc ttc atg tgc cac cac gcc    2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag    2554
Val Arg Ile Arg Gly Lys Ser Tyr Val Gln Cys Gln Gly Ile Pro Gln
            820                 825                 830 ggc tcc atc ctc tcc acg ctg ctc tgc agc ctg tgc tac ggc gac atg    2602
Gly Ser Ile Leu Ser Thr Leu Leu Cys Ser Leu Cys Tyr Gly Asp Met
835                 840                 845 gag aac aag ctg ttt gcg ggg att cgg cgg gac ggg ctg ctc ctg cgt    2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa    2698
Leu Val Asp Asp Phe Leu Leu Val Thr Pro His Leu Thr His Ala Lys
                870                 875                 880
```

Figure 1D

```
acc ttc ctc agg acc ctg gtc cga ggt gtc cct gag tat ggc tgc gtg    2746
Thr Phe Leu Arg Thr Leu Val Arg Gly Val Pro Glu Tyr Gly Cys Val
        885                 890                 895 gtg aac ttg cgg aag aca gtg gtg aac ttc cct gta gaa gac gag gcc    2794
Val Asn Leu Arg Lys Thr Val Val Asn Phe Pro Val Glu Asp Glu Ala
        900                 905                 910 ctg ggt ggc acg gct ttt gtt cag atg ccg gcc cac ggc cta ttc ccc    2842
Leu Gly Gly Thr Ala Phe Val Gln Met Pro Ala His Gly Leu Phe Pro
        915                 920                 925 tgg tgc ggc ctg ctg ctg gat acc cgg acc ctg gag gtg cag agc gac    2890
Trp Cys Gly Leu Leu Leu Asp Thr Arg Thr Leu Glu Val Gln Ser Asp
930                 935                 940                 945 tac tcc agc tat gcc cgg acc tcc atc aga gcc agt ctc acc ttc aac    2938
Tyr Ser Ser Tyr Ala Arg Thr Ser Ile Arg Ala Ser Leu Thr Phe Asn
                950                 955                 960 cgc ggc ttc aag gct ggg agg aac atg cgt cgc aaa ctc ttt ggg gtc    2986
Arg Gly Phe Lys Ala Gly Arg Asn Met Arg Arg Lys Leu Phe Gly Val
        965                 970                 975 ttg cgg ctg aag tgt cac agc ctg ttt ctg gat ttg cag gtg aac agc    3034
Leu Arg Leu Lys Cys His Ser Leu Phe Leu Asp Leu Gln Val Asn Ser
        980                 985                 990 ctc cag acg gtg tgc acc aac atc tac aag atc ctc ctg cag gcg        3082
Leu Gln Thr Val Cys Thr Asn Ile Tyr Lys Ile Leu Leu Leu Gln Ala
        995                 1000                1005 tac agg ttt cac gca tgt gtg ctg cag ctc cca ttt cat cag caa gtt    3130
Tyr Arg Phe His Ala Cys Val Leu Gln Leu Pro Phe His Gln Gln Val
1010                1015                1020                1025 tgg aag aac ccc aca ttt ttc ctg cgc gtc atc tct gac acg gcc tcc    3178
Trp Lys Asn Pro Thr Phe Phe Leu Arg Val Ile Ser Asp Thr Ala Ser
                1030                1035                1040 ctc tgc tac tcc atc ctg aaa gcc aag aac gca ggg atg tcg ctg ggg    3226
Leu Cys Tyr Ser Ile Leu Lys Ala Lys Asn Ala Gly Met Ser Leu Gly
                1045                1050                1055 gcc aag ggc gcc gcc ggc cct ctg ccc tcc gag gcc gtg cag tgg ctg    3274
Ala Lys Gly Ala Ala Gly Pro Leu Pro Ser Glu Ala Val Gln Trp Leu
        1060                1065                1070 tgc cac caa gca ttc ctg ctc aag ctg act cga cac cgt gtc acc tac    3322
Cys His Gln Ala Phe Leu Leu Lys Leu Thr Arg His Arg Val Thr Tyr
    1075                1080                1085 gtg cca ctc ctg ggg tca ctc agg aca gcc cag acg cag ctg agt cgg    3370
Val Pro Leu Leu Gly Ser Leu Arg Thr Ala Gln Thr Gln Leu Ser Arg
1090                1095                1100                1105
```

Figure 1E

```
aag ctc ccg ggg acg acg ctg act gcc ctg gag gcc gca gcc aac ccg   3418
Lys Leu Pro Gly Thr Thr Leu Thr Ala Leu Glu Ala Ala Ala Asn Pro
            1110                1115                1120 gca ctg ccc tca gac ttc aag acc atc ctg gac tga tggccacccg        3464
Ala Leu Pro Ser Asp Phe Lys Thr Ile Leu Asp
            1125                1130 cccacagcca ggccgagagc agacaccagc agccctgtca cgccgggctc tacgtcccag 3524
ggagggaggg gcggcccaca cccaggcccg caccgctggg agtctgaggc ctgagtgagt 3584
gtttggccga ggcctgcatg tccggctgaa ggctgagtgt ccggctgagg cctgagcgag 3644
tgtccagcca agggctgagt gtccagcaca cctgccgtct tcacttcccc acaggctggc 3704
gctcggctcc accccagggc cagcttttcc tcaccaggag cccggcttcc actccccaca 3764
taggaatagt ccatccccag attcgccatt gttcacccct cgccctgccc tcctttgcct 3824
tccacccccca ccatccaggt ggagaccctg agaaggaccc tgggagctct gggaatttgg 3884
agtgaccaaa ggtgtgccct gtacacaggc gaggaccctg cacctggatg ggggtccctg 3944
tgggtcaaat tgggggggagg tgctgtggga gtaaaatact gaatatatga gttttttcagt 4004
tttgaaaaaa a                                                      4015
```

Figure 1F

A.
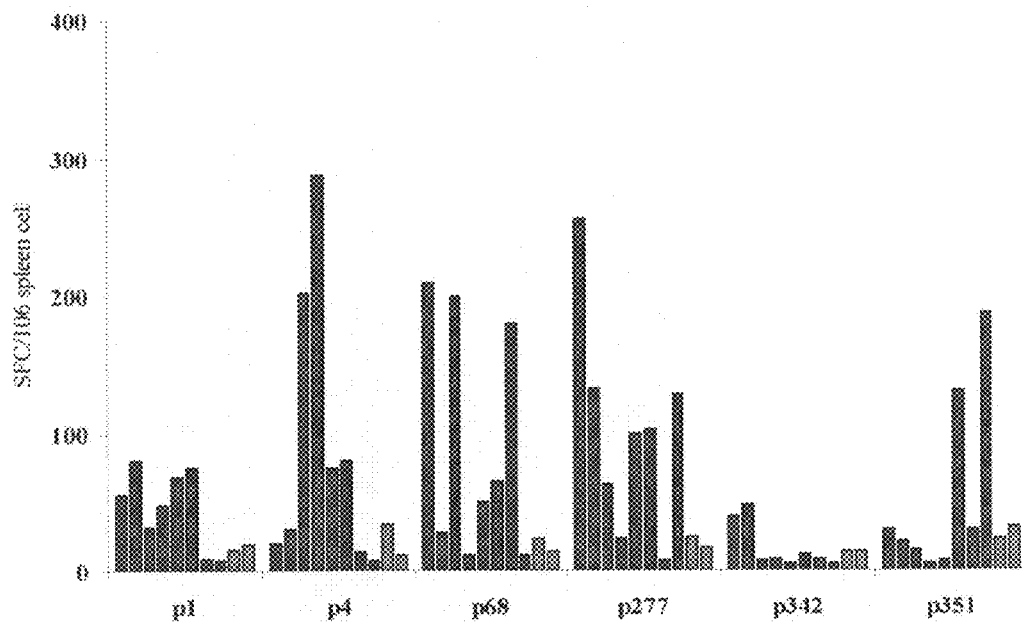
B.
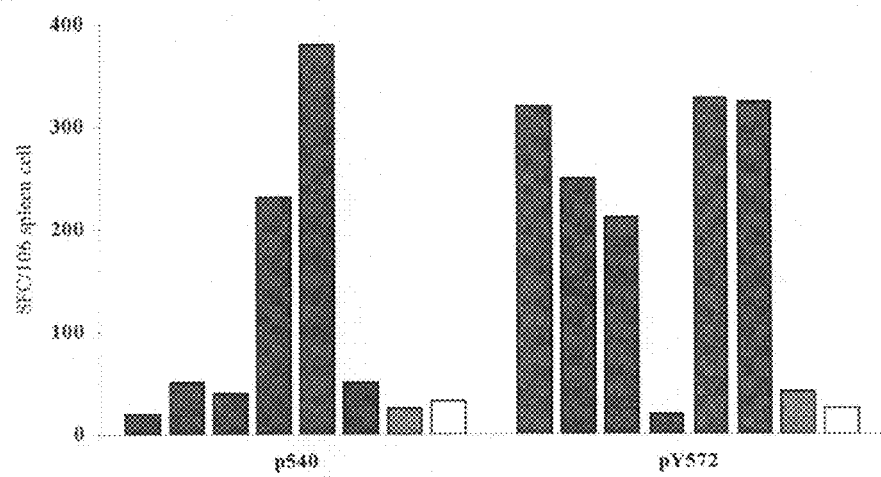
Figure 5

| | | | | | | | | | | |
|---|---|---|---|---|---|---|---|---|---|---|
| caggcagcgc | tgcgtcctgc | tgcgcacgtg | ggaagccctg | gccccggcca | ccccccgcg | | | | | 58 |

| | | | | | | | | | | | | | | | | |
|---|---|---|---|---|---|---|---|---|---|---|---|---|---|---|---|---|
| <u>atg</u> | ccg | cgc | gct | ccc | cgc | tgc | cga | gcc | gtg | cgc | tcc | ctg | ctg | cgc | agc | 106 |
| Met | Pro | Arg | Ala | Pro | Arg | Cys | Arg | Ala | Val | Arg | Ser | Leu | Leu | Arg | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | tac | cgc | gag | gtg | ctg | ccg | ctg | gcc | acg | ttc | gtg | cgg | cgc | ctg | ggg | 154 |
| His | Tyr | Arg | Glu | Val | Leu | Pro | Leu | Ala | Thr | Phe | Val | Arg | Arg | Leu | Gly | |
| | | | | 20 | | | | | 25 | | | | | 30 | | |

| | | | | | | | | | | | | | | | | |
|---|---|---|---|---|---|---|---|---|---|---|---|---|---|---|---|---|
| ccc | cag | ggc | tgg | cgg | ctg | gtg | cag | cgc | ggg | gac | ccg | gcg | gct | ttc | cgc | 202 |
| Pro | Gln | Gly | Trp | Arg | Leu | Val | Gln | Arg | Gly | Asp | Pro | Ala | Ala | Phe | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| gcg | ctg | gtg | gcc | cag | tgc | ctg | gtg | tgc | gtg | ccc | tgg | gac | gca | cgg | ccg | 250 |
| Ala | Leu | Val | Ala | Gln | Cys | Leu | Val | Cys | Val | Pro | Trp | Asp | Ala | Arg | Pro | |
| | | 50 | | | | | 55 | | | | | 60 | | | | |

| | | | | | | | | | | | | | | | | |
|---|---|---|---|---|---|---|---|---|---|---|---|---|---|---|---|---|
| ccc | ccc | gcc | gcc | ccc | tcc | ttc | cgc | cag | gtg | tcc | tgc | ctg | aag | gag | ctg | 298 |
| Pro | Pro | Ala | Ala | Pro | Ser | Phe | Arg | Gln | Val | Ser | Cys | Leu | Lys | Glu | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtg | gcc | cga | gtg | ctg | cag | agg | ctg | tgc | gag | cgc | ggc | gcg | aag | aac | gtg | 346 |
| Val | Ala | Arg | Val | Leu | Gln | Arg | Leu | Cys | Glu | Arg | Gly | Ala | Lys | Asn | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | gcc | ttc | ggc | ttc | gcg | ctg | ctg | gac | ggg | gcc | cgc | ggg | ggc | ccc | ccc | 394 |
| Leu | Ala | Phe | Gly | Phe | Ala | Leu | Leu | Asp | Gly | Ala | Arg | Gly | Gly | Pro | Pro | |
| | | | | 100 | | | | | 105 | | | | | 110 | | |

| | | | | | | | | | | | | | | | | |
|---|---|---|---|---|---|---|---|---|---|---|---|---|---|---|---|---|
| gag | gcc | ttc | acc | acc | agc | gtg | cgc | agc | tac | ctg | ccc | aac | acg | gtg | acc | 442 |
| Glu | Ala | Phe | Thr | Thr | Ser | Val | Arg | Ser | Tyr | Leu | Pro | Asn | Thr | Val | Thr | |
| | | | | 115 | | | | | 120 | | | | | 125 | | |

| | | | | | | | | | | | | | | | | |
|---|---|---|---|---|---|---|---|---|---|---|---|---|---|---|---|---|
| gac | gca | ctg | cgg | ggg | agc | ggg | gcg | tgg | ggg | ctg | ctg | ctg | cgc | cgc | gtg | 490 |
| Asp | Ala | Leu | Arg | Gly | Ser | Gly | Ala | Trp | Gly | Leu | Leu | Leu | Arg | Arg | Val | |
| | | 130 | | | | | 135 | | | | | 140 | | | | |

| | | | | | | | | | | | | | | | | |
|---|---|---|---|---|---|---|---|---|---|---|---|---|---|---|---|---|
| ggc | gac | gac | gtg | ctg | gtt | cac | ctg | ctg | gca | cgc | tgc | gcg | ctc | ttt | gtg | 538 |
| Gly | Asp | Asp | Val | Leu | Val | His | Leu | Leu | Ala | Arg | Cys | Ala | Leu | Phe | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctg | gtg | gct | ccc | agc | tgc | gcc | tac | cag | gtg | tgc | ggg | ccg | ccg | ctg | tac | 586 |
| Leu | Val | Ala | Pro | Ser | Cys | Ala | Tyr | Gln | Val | Cys | Gly | Pro | Pro | Leu | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | ctc | ggc | gct | gcc | act | cag | gcc | cgg | ccc | ccg | cca | cac | gct | agt | gga | 634 |
| Gln | Leu | Gly | Ala | Ala | Thr | Gln | Ala | Arg | Pro | Pro | Pro | His | Ala | Ser | Gly | |
| | | | | 180 | | | | | 185 | | | | | 190 | | |

| | | | | | | | | | | | | | | | | |
|---|---|---|---|---|---|---|---|---|---|---|---|---|---|---|---|---|
| ccc | cga | agg | cgt | ctg | gga | tgc | gaa | cgg | gcc | tgg | aac | cat | agc | gtc | agg | 682 |
| Pro | Arg | Arg | Arg | Leu | Gly | Cys | Glu | Arg | Ala | Trp | Asn | His | Ser | Val | Arg | |
| | | 195 | | | | | 200 | | | | | 205 | | | | |

| | | | | | | | | | | | | | | | | |
|---|---|---|---|---|---|---|---|---|---|---|---|---|---|---|---|---|
| gag | gcc | ggg | gtc | ccc | ctg | ggc | ctg | cca | gcc | ccg | ggt | gcg | agg | agg | cgc | 730 |
| Glu | Ala | Gly | Val | Pro | Leu | Gly | Leu | Pro | Ala | Pro | Gly | Ala | Arg | Arg | Arg | |
| | | 210 | | | | | 215 | | | | | 220 | | | | |

Figure 9A

```
ggg ggc agt gcc agc cga agt ctg ccg ttg ccc aag agg ccc agg cgt    778
Gly Gly Ser Ala Ser Arg Ser Leu Pro Leu Pro Lys Arg Pro Arg Arg
225                 230                 235                 240 ggc gct gcc cct gag ccg gag cgg acg ccc gtt ggg cag ggg tcc tgg    826
Gly Ala Ala Pro Glu Pro Glu Arg Thr Pro Val Gly Gln Gly Ser Trp
                245                 250                 255 gcc cac ccg ggc agg acg cgt gga ccg agt gac cgt ggt ttc tgt gtg    874
Ala His Pro Gly Arg Thr Arg Gly Pro Ser Asp Arg Gly Phe Cys Val
                260                 265                 270 gtg tca cct gcc aga ccc gcc gaa gaa gcc acc tct ttg gag ggt gcg    922
Val Ser Pro Ala Arg Pro Ala Glu Glu Ala Thr Ser Leu Glu Gly Ala
            275                 280                 285 ctc tct ggc acg cgc cac tcc cac cca tcc gtg ggc cgc cag cac cac    970
Leu Ser Gly Thr Arg His Ser His Pro Ser Val Gly Arg Gln His His
            290                 295                 300 gcg ggc ccc cca tcc aca tcg cgg cca cca cgt ccc tgg gac acg cct   1018
Ala Gly Pro Pro Ser Thr Ser Arg Pro Pro Arg Pro Trp Asp Thr Pro
305                 310                 315                 320 tgt ccc ccg gtg tac gcc gag acc aag cac ttc ctc tac tcc tca ggc   1066
Cys Pro Pro Val Tyr Ala Glu Thr Lys His Phe Leu Tyr Ser Ser Gly
                325                 330                 335 gac aag gag cag ctg cgg ccc tcc ttc cta ctc agc tct ctg agg ccc   1114
Asp Lys Glu Gln Leu Arg Pro Ser Phe Leu Leu Ser Ser Leu Arg Pro
                340                 345                 350 agc ctg act ggc gct cgg agg ctc gtg gag acc atc ttt ctg ggt tcc   1162
Ser Leu Thr Gly Ala Arg Arg Leu Val Glu Thr Ile Phe Leu Gly Ser
            355                 360                 365 agg ccc tgg atg cca ggg act ccc cgc agg ttg ccc cgc ctg ccc cag   1210
Arg Pro Trp Met Pro Gly Thr Pro Arg Arg Leu Pro Arg Leu Pro Gln
370                 375                 380 cgc tac tgg caa atg cgg ccc ctg ttt ctg gag ctg ctt ggg aac cac   1258
Arg Tyr Trp Gln Met Arg Pro Leu Phe Leu Glu Leu Leu Gly Asn His
385                 390                 395                 400 gcg cag tgc ccc tac ggg gtg ctc ctc aag acg cac tgc ccg ctg cga   1306
Ala Gln Cys Pro Tyr Gly Val Leu Leu Lys Thr His Cys Pro Leu Arg
                405                 410                 415 gct gcg gtc acc cca gca gcc ggt gtc tgt gcc cgg gag aag ccc cag   1354
Ala Ala Val Thr Pro Ala Ala Gly Val Cys Ala Arg Glu Lys Pro Gln
            420                 425                 430 ggc tct gtg gcg gcc ccc gag gag gag gac aca gac ccc cgt cgc ctg   1402
Gly Ser Val Ala Ala Pro Glu Glu Glu Asp Thr Asp Pro Arg Arg Leu
            435                 440                 445
```

Figure 9B

```
gtg cag ctg ctc cgc cag cac agc agc ccc tgg cag gtg tac ggc ttc    1450
Val Gln Leu Leu Arg Gln His Ser Ser Pro Trp Gln Val Tyr Gly Phe
    450             455                 460 gtg cgg gcc tgc ctg cgc cgg ctg gtg ccc cca ggc ctg tgg ggc tcc    1498
Val Arg Ala Cys Leu Arg Arg Leu Val Pro Pro Gly Leu Trp Gly Ser
465             470                 475                 480 agg cac aac gaa cgc cgc ttc ctc agg aac acc aag aag ttc atc tcc    1546
Arg His Asn Glu Arg Arg Phe Leu Arg Asn Thr Lys Lys Phe Ile Ser
                485                 490                 495 ctg ggg aag cat gcc aag ctc tcg ctg cag gag ctg acg tgg aag atg    1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt    1642
Ser Val Arg Asp Cys Ala Trp Leu Arg Arg Ser Pro Gly Val Gly Cys
        515                 520                 525 gtt ccg gcc gca gag cac cgt ctg cgt gag gag atc ctg gcc aag ttc    1690
Val Pro Ala Ala Glu His Arg Leu Arg Glu Glu Ile Leu Ala Lys Phe
    530                 535                 540 ctg cac tgg ctg atg agt gtg tac gtc gtc gag ctg ctc agg tct ttc    1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac    1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac    1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag    1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc    1930
His Arg Glu Ala Arg Pro Ala Leu Leu Thr Ser Arg Leu Arg Phe Ile
    610                 615                 620 ccc aag cct gac ggg ctg cgg ccg att gtg aac atg gac tac gtc gtg    1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg    2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
            660                 665                 670
```

Figure 9C

```
ccc ggc ctc ctg ggc gcc tct gtg ctg ggc ctg gac gat atc cac agg   2122
Pro Gly Leu Leu Gly Ala Ser Val Leu Gly Leu Asp Asp Ile His Arg
        675             680             685 gcc tgg cgc acc ttc gtg ctg cgt gtg cgg gcc cag gac ccg ccg cct   2170
Ala Trp Arg Thr Phe Val Leu Arg Val Arg Ala Gln Asp Pro Pro Pro
        690             695             700 gag ctg tac ttt gtc aag gtg gat gtg acg ggc gcg tac gac acc atc   2218
Glu Leu Tyr Phe Val Lys Val Asp Val Thr Gly Ala Tyr Asp Thr Ile
705             710             715                 720 ccc cag gac agg ctc acg gag gtc atc gcc agc atc atc aaa ccc cag   2266
Pro Gln Asp Arg Leu Thr Glu Val Ile Ala Ser Ile Ile Lys Pro Gln
                725             730             735 aac acg tac tgc gtg cgt cgg tat gcc gtg gtc cag aag gcc gcc cat   2314
Asn Thr Tyr Cys Val Arg Arg Tyr Ala Val Val Gln Lys Ala Ala His
                740             745             750 ggg cac gtc cgc aag gcc ttc aag agc cac gtc tct acc ttg aca gac   2362
Gly His Val Arg Lys Ala Phe Lys Ser His Val Ser Thr Leu Thr Asp
        755             760             765 ctc cag ccg tac atg cga cag ttc gtg gct cac ctg cag gag acc agc   2410
Leu Gln Pro Tyr Met Arg Gln Phe Val Ala His Leu Gln Glu Thr Ser
        770             775             780 ccg ctg agg gat gcc gtc gtc atc gag cag agc tcc tcc ctg aat gag   2458
Pro Leu Arg Asp Ala Val Val Ile Glu Gln Ser Ser Ser Leu Asn Glu
785             790             795             800 gcc agc agt ggc ctc ttc gac gtc ttc cta cgc ttc atg tgc cac cac   2506
Ala Ser Ser Gly Leu Phe Asp Val Phe Leu Arg Phe Met Cys His His
                805             810             815 gcc gtg cgc atc agg ggc aag tcc tac gtc cag tgc cag ggg atc ccg   2554
Ala Val Arg Ile Arg Gly Lys Ser Tyr Val Gln Cys Gln Gly Ile Pro
        820             825             830 cag ggc tcc atc ctc tcc acg ctg ctc tgc agc ctg tgc tac ggc gac   2602
Gln Gly Ser Ile Leu Ser Thr Leu Leu Cys Ser Leu Cys Tyr Gly Asp
        835             840             845 atg gag aac aag ctg ttt gcg ggg att cgg cgg gac ggg ctg ctc ctg   2650
Met Glu Asn Lys Leu Phe Ala Gly Ile Arg Arg Asp Gly Leu Leu Leu
850             855             860 cgt ttg ttc ttg ttg gtg aca cct cac ctc acc cac gcg aaa acc ttc   2698
Arg Leu Phe Leu Leu Val Thr Pro His Leu Thr His Ala Lys Thr Phe
865             870             875             880 ctc agg acc ctg gtc cga ggt gtc cct gag tat ggc tgc gtg gtg aac   2746
Leu Arg Thr Leu Val Arg Gly Val Pro Glu Tyr Gly Cys Val Val Asn
                885             890             895
```

Figure 9D

```
ttg cgg aag aca gtg gtg aac ttc cct gta gaa gac gag gcc ctg ggt      2794
Leu Arg Lys Thr Val Val Asn Phe Pro Val Glu Asp Glu Ala Leu Gly
        900                 905                 910 ggc acg gct ttt gtt cag atg ccg gcc cac ggc cta ttc ccc tgg tgc      2842
Gly Thr Ala Phe Val Gln Met Pro Ala His Gly Leu Phe Pro Trp Cys
        915                 920                 925 ggc ctg ctg ctg gat acc cgg acc ctg gag gtg cag agc gac tac tcc      2890
Gly Leu Leu Leu Asp Thr Arg Thr Leu Glu Val Gln Ser Asp Tyr Ser
        930                 935                 940 agc tat gcc cgg acc tcc atc aga gcc agt ctc acc ttc aac cgc ggc      2938
Ser Tyr Ala Arg Thr Ser Ile Arg Ala Ser Leu Thr Phe Asn Arg Gly
945                 950                 955                 960 ttc aag gct ggg agg aac atg cgt cgc aaa ctc ttt ggg gtc ttg cgg      2986
Phe Lys Ala Gly Arg Asn Met Arg Arg Lys Leu Phe Gly Val Leu Arg
                965                 970                 975 ctg aag tgt cac agc ctg ttt ctg gat ttg cag gtg aac agc ctc cag      3034
Leu Lys Cys His Ser Leu Phe Leu Asp Leu Gln Val Asn Ser Leu Gln
            980                 985                 990 acg gtg tgc acc aac atc tac aag atc ctc ctg ctg cag  gcg tac agg     3082
Thr Val Cys Thr Asn Ile Tyr Lys Ile Leu Leu Leu Gln  Ala Tyr Arg
            995                1000                1005 ttt cac gca tgt gtg ctg cag ctc cca ttt cat cag caa gtt tgg          3127
Phe His Ala Cys Val Leu Gln Leu Pro Phe His Gln Gln Val Trp
        1010                1015                1020 aag aac ccc aca ttt ttc ctg cgc gtc atc tct gac acg gcc tcc          3172
Lys Asn Pro Thr Phe Phe Leu Arg Val Ile Ser Asp Thr Ala Ser
        1025                1030                1035 ctc tgc tac tcc atc ctg aaa gcc aag aac gca ggg atg tcg ctg          3217
Leu Cys Tyr Ser Ile Leu Lys Ala Lys Asn Ala Gly Met Ser Leu
        1040                1045                1050 ggg gcc aag ggc gcc gcc ggc cct ctg ccc tcc gag gcc gtg cag          3262
Gly Ala Lys Gly Ala Ala Gly Pro Leu Pro Ser Glu Ala Val Gln
        1055                1060                1065 tgg ctg tgc cac caa gca ttc ctg ctc aag ctg act cga cac cgt          3307
Trp Leu Cys His Gln Ala Phe Leu Leu Lys Leu Thr Arg His Arg
        1070                1075                1080 gtc acc tac gtg cca ctc ctg ggg tca ctc agg aca gcc cag acg          3352
Val Thr Tyr Val Pro Leu Leu Gly Ser Leu Arg Thr Ala Gln Thr
        1085                1090                1095 cag ctg agt cgg aag ctc ccg ggg acg acg ctg act gcc ctg gag          3397
Gln Leu Ser Arg Lys Leu Pro Gly Thr Thr Leu Thr Ala Leu Glu
        1100                1105                1110
```

Figure 9E

| | | | | | | | | | | | | |
|---|---|---|---|---|---|---|---|---|---|---|---|---|
| gcc | gca | gcc | aac | ccg | gca | ctg | ccc | tca | gac | ttc | aag | acc atc ctg |
| Ala | Ala | Ala | Asn | Pro | Ala | Leu | Pro | Ser | Asp | Phe | Lys | Thr Ile Leu |
| | 1115 | | | | 1120 | | | | | 1125 | | |

3442 gac tga tggccacccg cccacagcca ggccgagagc agacaccagc agccctgtca  3498
Asp cgccgggctc tacgtcccag ggagggaggg gcggcccaca cccaggcccg caccgctggg  3558
agtctgaggc ctgagtgagt gtttggccga ggcctgcatg tccggctgaa ggctgagtgt  3618
ccggctgagg cctgagcgag tgtccagcca agggctgagt gtccagcaca cctgccgtct  3678
tcacttcccc acaggctggc gctcggctcc accccagggc cagcttttcc tcaccaggag  3738
cccggcttcc actccccaca taggaatagt ccatcccag attcgccatt gttcacccct  3798
cgccctgccc tcctttgcct tcaccccca ccatccaggt ggagaccctg agaaggaccc  3858
tgggagctct gggaatttgg agtgaccaaa ggtgtgccct gtacacaggc gaggaccctg  3918
cacctggatg ggggtccctg tgggtcaaat tggggggagg tgctgtggga gtaaaatact  3978
gaatatatga gttttcagt tttgaaaaaa a  4009

Figure 9F

```
          caggcagcgc tgcgtcctgc tgcgcacgtg ggaagccctg gccccggcca ccccgcg          58 atg ccg cgc gct ccc cgc tgc cga gcc gtg cgc tcc ctg ctg cgc agc          106
     Met Pro Arg Ala Pro Arg Cys Arg Ala Val Arg Ser Leu Leu Arg Ser
     1             5                  10                 15 cac tac cgc gag gtg ctg ccg ctg gcc acg ttc gtg cgg cgc ctg ggg          154
     His Tyr Arg Glu Val Leu Pro Leu Ala Thr Phe Val Arg Arg Leu Gly
                 20                  25                 30 ccc cag ggc tgg cgg ctg gtg cag cgc ggg gac ccg gcg gct ttc cgc          202
     Pro Gln Gly Trp Arg Leu Val Gln Arg Gly Asp Pro Ala Ala Phe Arg
             35                  40                  45 gcg ctg gtg gcc cag tgc ctg gtg tgc gtg ccc tgg gac gca cgg ccg          250
     Ala Leu Val Ala Gln Cys Leu Val Cys Val Pro Trp Asp Ala Arg Pro
         50                  55                  60 ccc ccc gcc gcc ccc tcc ttc cgc cag gtg tcc tgc ctg aag gag ctg          298
     Pro Pro Ala Ala Pro Ser Phe Arg Gln Val Ser Cys Leu Lys Glu Leu
     65                  70                  75                 80 gtg gcc cga gtg ctg cag agg ctg tgc gag cgc ggc gcg aag aac gtg          346
     Val Ala Arg Val Leu Gln Arg Leu Cys Glu Arg Gly Ala Lys Asn Val
                     85                  90                 95 ctg gcc ttc ggc ttc gcg ctg ctg gac ggg gcc cgc ggg ggc ccc ccc          394
     Leu Ala Phe Gly Phe Ala Leu Leu Asp Gly Ala Arg Gly Gly Pro Pro
                 100                 105                110 gag gcc ttc acc acc agc gtg cgc agc tac ctg ccc aac acg gtg acc          442
     Glu Ala Phe Thr Thr Ser Val Arg Ser Tyr Leu Pro Asn Thr Val Thr
             115                 120                 125 gac gca ctg cgg ggg agc ggg gcg tgg ggg ctg ctg ctg cgc cgc gtg          490
     Asp Ala Leu Arg Gly Ser Gly Ala Trp Gly Leu Leu Leu Arg Arg Val
         130                 135                 140 ggc gac gac gtg ctg gtt cac ctg ctg gca cgc tgc gcg ctc ttt gtg          538
     Gly Asp Asp Val Leu Val His Leu Leu Ala Arg Cys Ala Leu Phe Val
     145                 150                 155                160 ctg gtg gct ccc agc tgc gcc tac cag gtg tgc ggg ccg ccg ctg tac          586
     Leu Val Ala Pro Ser Cys Ala Tyr Gln Val Cys Gly Pro Pro Leu Tyr
                     165                 170                175 cag ctc ggc gct gcc act cag gcc cgg ccc cca cac gct agt gga          634
     Gln Leu Gly Ala Ala Thr Gln Ala Arg Pro Pro His Ala Ser Gly
                 180                 185                 190 ccc cga agg cgt ctg gga tgc gaa cgg gcc tgg aac cat agc gtc agg          682
     Pro Arg Arg Arg Leu Gly Cys Glu Arg Ala Trp Asn His Ser Val Arg
             195                 200                 205
```

Figure 10A

```
gag gcc ggg gtc ccc ctg ggc ctg cca gcc ccg ggt gcg agg agg cgc    730
Glu Ala Gly Val Pro Leu Gly Leu Pro Ala Pro Gly Ala Arg Arg Arg
    210             215             220 ggg ggc agt gcc agc cga agt ctg ccg ttg ccc aag agg ccc agg cgt    778
Gly Gly Ser Ala Ser Arg Ser Leu Pro Leu Pro Lys Arg Pro Arg Arg
225             230             235             240 ggc gct gcc cct gag ccg gag cgg acg ccc gtt ggg cag ggg tcc tgg    826
Gly Ala Ala Pro Glu Pro Glu Arg Thr Pro Val Gly Gln Gly Ser Trp
                245             250             255 gcc cac ccg ggc agg acg cgt gga ccg agt gac cgt ggt ttc tgt gtg    874
Ala His Pro Gly Arg Thr Arg Gly Pro Ser Asp Arg Gly Phe Cys Val
            260             265             270 gtg tca cct gcc aga ccc gcc gaa gaa gcc acc tct ttg gag ggt gcg    922
Val Ser Pro Ala Arg Pro Ala Glu Glu Ala Thr Ser Leu Glu Gly Ala
        275             280             285 ctc tct ggc acg cgc cac tcc cac cca tcc gtg ggc cgc cag cac cac    970
Leu Ser Gly Thr Arg His Ser His Pro Ser Val Gly Arg Gln His His
    290             295             300 gcg ggc ccc cca tcc aca tcg cgg cca cca cgt ccc tgg gac acg cct   1018
Ala Gly Pro Pro Ser Thr Ser Arg Pro Pro Arg Pro Trp Asp Thr Pro
305             310             315             320 tgt ccc ccg gtg tac gcc gag acc aag cac ttc ctc tac tcc tca ggc   1066
Cys Pro Pro Val Tyr Ala Glu Thr Lys His Phe Leu Tyr Ser Ser Gly
                325             330             335 gac aag gag cag ctg cgg ccc tcc ttc cta ctc agc tct ctg agg ccc   1114
Asp Lys Glu Gln Leu Arg Pro Ser Phe Leu Leu Ser Ser Leu Arg Pro
            340             345             350 agc ctg act ggc gct cgg agg ctc gtg gag acc atc ttt ctg ggt tcc   1162
Ser Leu Thr Gly Ala Arg Arg Leu Val Glu Thr Ile Phe Leu Gly Ser
        355             360             365 agg ccc tgg atg cca ggg act ccc cgc agg ttg ccc cgc ctg ccc cag   1210
Arg Pro Trp Met Pro Gly Thr Pro Arg Arg Leu Pro Arg Leu Pro Gln
    370             375             380 cgc tac tgg caa atg cgg ccc ctg ttt ctg gag ctg ctt ggg aac cac   1258
Arg Tyr Trp Gln Met Arg Pro Leu Phe Leu Glu Leu Leu Gly Asn His
385             390             395             400 gcg cag tgc ccc tac ggg gtg ctc ctc aag acg cac tgc ccg ctg cga   1306
Ala Gln Cys Pro Tyr Gly Val Leu Leu Lys Thr His Cys Pro Leu Arg
                405             410             415 gct gcg gtc acc cca gca gcc ggt gtc tgt gcc cgg gag aag ccc cag   1354
Ala Ala Val Thr Pro Ala Ala Gly Val Cys Ala Arg Glu Lys Pro Gln
            420             425             430
```

Figure 10B

| | |
|---|---|
| ggc tct gtg gcg gcc ccc gag gag gag gac aca gac ccc cgt cgc ctg<br>Gly Ser Val Ala Ala Pro Glu Glu Glu Asp Thr Asp Pro Arg Arg Leu<br>435           440           445 | 1402 |
| gtg cag ctg ctc cgc cag cac agc agc ccc tgg cag gtg tac ggc ttc<br>Val Gln Leu Leu Arg Gln His Ser Ser Pro Trp Gln Val Tyr Gly Phe<br>450           455           460 | 1450 |
| gtg cgg gcc tgc ctg cgc cgg ctg gtg ccc cca ggc ctc tgg ggc tcc<br>Val Arg Ala Cys Leu Arg Arg Leu Val Pro Pro Gly Leu Trp Gly Ser<br>465           470           475           480 | 1498 |
| agg cac aac gaa cgc cgc ttc ctc agg aac acc aag aag ttc atc tcc<br>Arg His Asn Glu Arg Arg Phe Leu Arg Asn Thr Lys Lys Phe Ile Ser<br>485           490           495 | 1546 |
| ctg ggg aag cat gcc aag ctc tcg ctg cag gag ctg acg tgg aag atg<br>Leu Gly Lys His Ala Lys Leu Ser Leu Gln Glu Leu Thr Trp Lys Met<br>500           505           510 | 1594 |
| agc gtg cgg gac tgc gct tgg ctg cgc agg agc cca ggg gtt ggc tgt<br>Ser Val Arg Asp Cys Ala Trp Leu Arg Arg Ser Pro Gly Val Gly Cys<br>515           520           525 | 1642 |
| gtt ccg gcc gca gag cac cgt ctg cgt gag gag atc ctg gcc aag ttc<br>Val Pro Ala Ala Glu His Arg Leu Arg Glu Glu Ile Leu Ala Lys Phe<br>530           535           540 | 1690 |
| ctg cac tgg ctg atg agt gtg tac gtc gtc gag ctg ctc agg tct ttc<br>Leu His Trp Leu Met Ser Val Tyr Val Val Glu Leu Leu Arg Ser Phe<br>545           550           555           560 | 1738 |
| ttt tat gtc acg gag acc acg ttt caa aag aac agg ctc ttt ttc tac<br>Phe Tyr Val Thr Glu Thr Thr Phe Gln Lys Asn Arg Leu Phe Phe Tyr<br>565           570           575 | 1786 |
| cgg aag agt gtc tgg agc aag ttg caa agc att gga atc aga cag cac<br>Arg Lys Ser Val Trp Ser Lys Leu Gln Ser Ile Gly Ile Arg Gln His<br>580           585           590 | 1834 |
| ttg aag agg gtg cag ctg cgg gag ctg tcg gaa gca gag gtc agg cag<br>Leu Lys Arg Val Gln Leu Arg Glu Leu Ser Glu Ala Glu Val Arg Gln<br>595           600           605 | 1882 |
| cat cgg gaa gcc agg ccc gcc ctg ctg acg tcc aga ctc cgc ttc atc<br>His Arg Glu Ala Arg Pro Ala Leu Leu Thr Ser Arg Leu Arg Phe Ile<br>610           615           620 | 1930 |
| ccc aag cct gac ggg ctg cgg ccg att gtg aac atg gac tac gtc gtg<br>Pro Lys Pro Asp Gly Leu Arg Pro Ile Val Asn Met Asp Tyr Val Val<br>625           630           635           640 | 1978 |
| gga gcc aga acg ttc cgc aga gaa aag agg gcc gag cgt ctc acc tcg<br>Gly Ala Arg Thr Phe Arg Arg Glu Lys Arg Ala Glu Arg Leu Thr Ser<br>645           650           655 | 2026 |

Figure 10C

```
agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
        660                 665                 670 ccc ggc ctc ctg ggc gcc tct gtg ctg ggc ctg gac gat atc cac agg    2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct    2170
Ala Trp Arg Thr Phe Val Leu Arg Val Arg Ala Gln Asp Pro Pro Pro
690                 695                 700 gag ctg tac ttt gtc aag gtg gat gtg acg ggc gcg tac gac acc atc    2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag    2266
Pro Gln Asp Arg Leu Thr Glu Val Ile Ala Ser Ile Ile Lys Pro Gln
        725                 730                 735 aac acg tac tgc gtg cgt cgg tat gcc gtg gtc cag aag gcc gcc cat    2314
Asn Thr Tyr Cys Val Arg Arg Tyr Ala Val Val Gln Lys Ala Ala His
        740                 745                 750 ggg cac gtc cgc aag gcc ttc aag agc cac gtc tct acc ttg aca gac    2362
Gly His Val Arg Lys Ala Phe Lys Ser His Val Ser Thr Leu Thr Asp
        755                 760                 765 ctc cag ccg tac atg cga cag ttc gtg gct cac ctg cag gag acc agc    2410
Leu Gln Pro Tyr Met Arg Gln Phe Val Ala His Leu Gln Glu Thr Ser
        770                 775                 780 ccg ctg agg gat gcc gtc gtc atc gag cag agc tcc tcc ctg aat gag    2458
Pro Leu Arg Asp Ala Val Val Ile Glu Gln Ser Ser Ser Leu Asn Glu
785                 790                 795                 800 gcc agc agt ggc ctc ttc gac gtc ttc cta cgc ttc atg tgc cac cac    2506
Ala Ser Ser Gly Leu Phe Asp Val Phe Leu Arg Phe Met Cys His His
                805                 810                 815 gcc gtg cgc atc agg ggc aag tcc tac gtc cag tgc cag ggg atc ccg    2554
Ala Val Arg Ile Arg Gly Lys Ser Tyr Val Gln Cys Gln Gly Ile Pro
        820                 825                 830 cag ggc tcc atc ctc tcc acg ctc ctc tgc agc ctg tgc tac ggc gac    2602
Gln Gly Ser Ile Leu Ser Thr Leu Leu Cys Ser Leu Cys Tyr Gly Asp
        835                 840                 845 atg gag aac aag ctg ttt gcg ggg att cgg cgg gac ggg ctg ctc gtg    2650
Met Glu Asn Lys Leu Phe Ala Gly Ile Arg Arg Asp Gly Leu Leu Val
        850                 855                 860 aca cct cac ctc acc cac gcg aaa acc ttc ctc agg acc ctg gtc cga    2698
Thr Pro His Leu Thr His Ala Lys Thr Phe Leu Arg Thr Leu Val Arg
865                 870                 875                 880
```

Figure 10D

```
ggt gtc cct gag tat ggc tgc gtg gtg aac ttg cgg aag aca gtg gtg         2746
Gly Val Pro Glu Tyr Gly Cys Val Val Asn Leu Arg Lys Thr Val Val
            885                 890                 895 aac ttc cct gta gaa gac gag gcc ctg ggt ggc acg gct ttt gtt cag         2794
Asn Phe Pro Val Glu Asp Glu Ala Leu Gly Gly Thr Ala Phe Val Gln
            900                 905                 910 atg ccg gcc cac ggc cta ttc ccc tgg tgc ggc ctg ctg ctg gat acc         2842
Met Pro Ala His Gly Leu Phe Pro Trp Cys Gly Leu Leu Leu Asp Thr
            915                 920                 925 cgg acc ctg gag gtg cag agc gac tac tcc agc tat gcc cgg acc tcc         2890
Arg Thr Leu Glu Val Gln Ser Asp Tyr Ser Ser Tyr Ala Arg Thr Ser
            930                 935                 940 atc aga gcc agt ctc acc ttc aac cgc ggc ttc aag gct ggg agg aac         2938
Ile Arg Ala Ser Leu Thr Phe Asn Arg Gly Phe Lys Ala Gly Arg Asn
945                     950                 955                 960 atg cgt cgc aaa ctc ttt ggg gtc ttg cgg ctg aag tgt cac agc ctg         2986
Met Arg Arg Lys Leu Phe Gly Val Leu Arg Leu Lys Cys His Ser Leu
                965                 970                 975 ttt ctg gat ttg cag gtg aac agc ctc cag acg gtg tgc acc aac atc         3034
Phe Leu Asp Leu Gln Val Asn Ser Leu Gln Thr Val Cys Thr Asn Ile
            980                 985                 990 tac aag atc ctc ctg ctg cag gcg tac agg ttt cac gca tgt gtg ctg         3082
Tyr Lys Ile Leu Leu Leu Gln Ala Tyr Arg Phe His Ala Cys Val Leu
            995                 1000                1005 cag ctc cca ttt cat cag caa gtt tgg aag aac ccc aca ttt ttc             3127
Gln Leu Pro Phe His Gln Gln Val Trp Lys Asn Pro Thr Phe Phe
        1010                1015                1020 ctg cgc gtc atc tct gac acg gcc tcc ctc tgc tac tcc atc ctg             3172
Leu Arg Val Ile Ser Asp Thr Ala Ser Leu Cys Tyr Ser Ile Leu
        1025                1030                1035 aaa gcc aag aac gca ggg atg tcg ctg ggg gcc aag ggc gcc gcc             3217
Lys Ala Lys Asn Ala Gly Met Ser Leu Gly Ala Lys Gly Ala Ala
        1040                1045                1050 ggc cct ctg ccc tcc gag gcc gtg cag tgg ctg tgc cac caa gca             3262
Gly Pro Leu Pro Ser Glu Ala Val Gln Trp Leu Cys His Gln Ala
        1055                1060                1065 ttc ctg ctc aag ctg act cga cac cgt gtc acc tac gtg cca ctc             3307
Phe Leu Leu Lys Leu Thr Arg His Arg Val Thr Tyr Val Pro Leu
        1070                1075                1080 ctg ggg tca ctc agg aca gcc cag acg cag ctg agt cgg aag ctc             3352
Leu Gly Ser Leu Arg Thr Ala Gln Thr Gln Leu Ser Arg Lys Leu
        1085                1090                1095
```

Figure 10E

| | | |
|---|---|---|
| ccg ggg acg acg ctg act gcc ctg gag gcc gca gcc aac ccg gca<br>Pro Gly Thr Thr Leu Thr Ala Leu Glu Ala Ala Ala Asn Pro Ala<br>    1100                               1105                         1110 | | 3397 |
| ctg ccc tca gac ttc aag acc atc ctg gac tga tggccacccg<br>Leu Pro Ser Asp Phe Lys Thr Ile Leu Asp<br>    1115                           1120 | | 3440 |
| cccacagcca ggccgagagc agacaccagc agccctgtca cgccgggctc tacgtcccag | | 3500 |
| ggagggaggg gcggcccaca cccaggcccg caccgctggg agtctgaggc ctgagtgagt | | 3560 |
| gtttggccga ggcctgcatg tccggctgaa ggctgagtgt ccggctgagg cctgagcgag | | 3620 |
| tgtccagcca agggctgagt gtccagcaca cctgccgtct tcacttcccc acaggctggc | | 3680 |
| gctcggctcc accccagggc cagcttttcc tcaccaggag cccggcttcc actccccaca | | 3740 |
| taggaatagt ccatccccag attcgccatt gttcacccct cgccctgccc tcctttgcct | | 3800 |
| tccaccccca ccatccaggt ggagaccctg agaaggaccc tgggagctct gggaatttgg | | 3860 |
| agtgaccaaa ggtgtgccct gtacacaggc gaggaccctg cacctggatg ggggtccctg | | 3920 |
| tgggtcaaat tgggggggagg tgctgtggga gtaaaatact gaatatatga gtttttcagt | | 3980 |
| tttgaaaaaa a | | 3991 |

Figure 10F

A
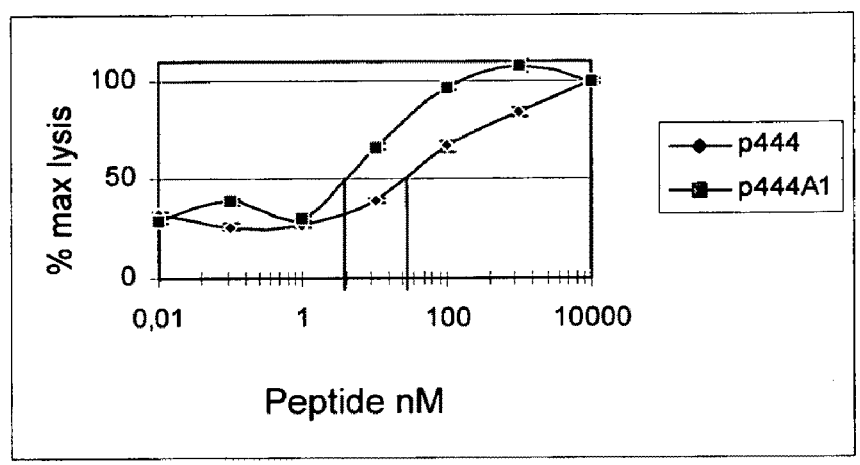
B
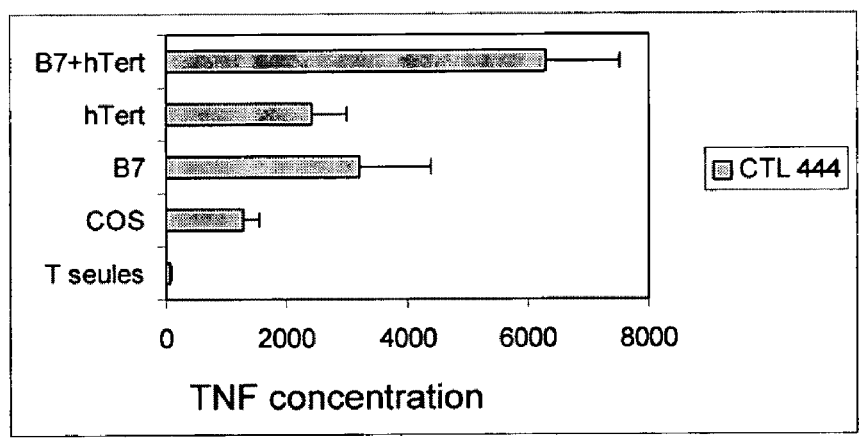
Figure 12

SEQUENCE LISTING

```
<160> NUMBER OF SEQ ID NOS: 42

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Leu Ala Lys Phe Leu His Trp Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Pro Arg Cys Arg Ala Val Arg Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Leu Phe Gly Val Leu Arg Leu Lys
1               5

<210> SEQ ID NO 4
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Val Tyr Ala Glu Thr Lys His Phe Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Tyr Gly Phe Val Arg Ala Cys Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Pro Arg Ala Pro Arg Cys Arg Ala
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Pro Arg Cys Arg Ala Val Arg Ser Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Pro Ser Phe Arg Gln Val Ser Cys Leu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Pro Ala Glu Glu Ala Thr Ser Leu
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Pro Ser Phe Leu Leu Ser Ser Leu
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Pro Ser Leu Thr Gly Ala Arg Arg Leu
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Pro Arg Arg Leu Val Gln Leu Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Val Arg Ala Cys Leu Arg Arg Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gly Arg Asn Met Arg Arg Lys Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Leu Pro Gly Thr Thr Leu Thr Ala Leu
1               5
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Leu Pro Ser Pro Lys Phe Thr Ile Leu
1               5
```

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ala Pro Arg Arg Leu Val Gln Leu Leu
1               5
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (9)..(9)
<223> OTHER INFORMATION: Ala, Leu, Ile, Met, Val, Phe, Trp or Tyr

<400> SEQUENCE: 18

```
Xaa Pro Xaa Xaa Xaa Xaa Xaa Xaa Xaa
1               5
```

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(9)
<223> OTHER INFORMATION: Any amino acid
<220> FEATURE:
<221> NAME/KEY: MOD_RES
<222> LOCATION: (10)..(10)
<223> OTHER INFORMATION: Ala, Leu, Ile, Met, Val, Phe, Trp or Tyr

<400> SEQUENCE: 19

```
Xaa Pro Xaa Xaa Xaa Xaa Xaa Xaa Xaa Xaa
1               5                   10
```

<210> SEQ ID NO 20
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Met Pro Arg Ala Pro Arg Cys Arg Ala Ala Pro Arg Cys Arg Ala Val
1               5                   10                  15

Arg Ser Leu Ala Pro Ser Phe Arg Gln Val Ser Cys Leu Arg Pro Ala
            20                  25                  30

Glu Glu Ala Thr Ser Leu Arg Pro Ser Phe Leu Leu Ser Ser Leu Arg
        35                  40                  45

Pro Ser Leu Thr Gly Ala Arg Arg Leu
    50                  55
```

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atgccgcgcg ctccccgctg ccgagcc                                              27

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gctccccgct gccgagccgt gcgctccctg                                           30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gccccctcct tccgccaggt gtcctgcctg                                           30

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agacccgccg aagaagccac ctctttg                                              27

<210> SEQ ID NO 25

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cggccctcct tcctactcag ctctctg                                              27

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aggcccagcc tgactggcgc tcggaggctc                                           30

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 gaccccgtc gcctggtgca gctgctc                                               27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttcgtgcggg cctgcctgcg ccggctg                                              27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gctgggagga acatgcgtcg caaactc                                              27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcccgggga cgacgctgac tgccctg                                              27

<210> SEQ ID NO 31
<211> LENGTH: 27
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 31
ctgccctcag acttcaagac catcctg                                       27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 gcccccgtc gcctggtgca gctgctc                                        27

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Pro His Glu Arg Asn Gly Phe Thr Val
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Pro Arg Arg Ile Arg Gln Gly Leu
1               5

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Pro Pro Ala Thr Arg Pro Pro Asn Ala Pro Ile Leu
1               5                   10

<210> SEQ ID NO 36
<211> LENGTH: 4015
<212> TYPE: DNA
<213> ORGANISM: Homo sapiens
<220> FEATURE:
<221> NAME/KEY: CDS
<222> LOCATION: (56)..(3454)

<400> SEQUENCE: 36
gcagcgctgc gtcctgctgc gcacgtggga agccctggcc ccggccaccc ccgcg atg    58
                                                             Met
                                                             1 ccg cgc gct ccc cgc tgc cga gcc gtg cgc tcc ctg ctg cgc agc cac    106

|  |  |  |  |  |  |  |  |  |  |  |  |  |  |  |  |
|---|---|---|---|---|---|---|---|---|---|---|---|---|---|---|---|
| Pro | Arg | Ala | Pro<br>5 | Arg | Cys | Arg | Ala | Val<br>10 | Arg | Ser | Leu | Leu<br>15 | Arg | Ser | His |

| tac<br>Tyr | cgc<br>Arg<br>20 | gag<br>Glu | gtg<br>Val | ctg<br>Leu | ccg<br>Pro<br>25 | ctg<br>Leu | gcc<br>Ala | acg<br>Thr | ttc<br>Phe | gtg<br>Val<br>30 | cgg<br>Arg | cgc<br>Arg | ctg<br>Leu | ggg<br>Gly | ccc<br>Pro | 154 |

| cag<br>Gln | ggc<br>Gly<br>35 | tgg<br>Trp | cgg<br>Arg | ctg<br>Leu | gtg<br>Val<br>40 | cag<br>Gln | cgc<br>Arg | ggg<br>Gly | gac<br>Asp | ccg<br>Pro<br>45 | gcg<br>Ala | gct<br>Ala | ttc<br>Phe | cgc<br>Arg | gcg<br>Ala | 202 |

| ctg<br>Leu<br>50 | gtg<br>Val | gcc<br>Ala | cag<br>Gln | tgc<br>Cys | ctg<br>Leu<br>55 | gtg<br>Val | tgc<br>Cys | gtg<br>Val | ccc<br>Pro | tgg<br>Trp<br>60 | gac<br>Asp | gca<br>Ala | cgg<br>Arg | ccg<br>Pro | ccc<br>Pro<br>65 | 250 |

| ccc<br>Pro | gcc<br>Ala | gcc<br>Ala | ccc<br>Pro | tcc<br>Ser<br>70 | ttc<br>Phe | cgc<br>Arg | cag<br>Gln | gtg<br>Val | tcc<br>Ser<br>75 | tgc<br>Cys | ctg<br>Leu | aag<br>Lys | gag<br>Glu | ctg<br>Leu<br>80 | gtg<br>Val | 298 |

| gcc<br>Ala | cga<br>Arg | gtg<br>Val | ctg<br>Leu<br>85 | cag<br>Gln | agg<br>Arg | ctg<br>Leu | tgc<br>Cys | gag<br>Glu<br>90 | cgc<br>Arg | ggc<br>Gly | gcg<br>Ala | aag<br>Lys | aac<br>Asn<br>95 | gtg<br>Val | ctg<br>Leu | 346 |

| gcc<br>Ala | ttc<br>Phe | ggc<br>Gly<br>100 | ttc<br>Phe | gcg<br>Ala | ctg<br>Leu | ctg<br>Leu | gac<br>Asp<br>105 | ggg<br>Gly | gcc<br>Ala | cgg<br>Arg | ggc<br>Gly | ggc<br>Gly<br>110 | ccc<br>Pro | ccc<br>Pro | gag<br>Glu | 394 |

| gcc<br>Ala | ttc<br>Phe | acc<br>Thr<br>115 | acc<br>Thr | agc<br>Ser | gtg<br>Val | cgc<br>Arg | agc<br>Ser<br>120 | tac<br>Tyr | ctg<br>Leu | ccc<br>Pro | aac<br>Asn | acg<br>Thr<br>125 | gtg<br>Val | acc<br>Thr | gac<br>Asp | 442 |

| gca<br>Ala<br>130 | ctg<br>Leu | cgg<br>Arg | ggg<br>Gly | agc<br>Ser | ggg<br>Gly<br>135 | gcg<br>Ala | tgg<br>Trp | ggg<br>Gly | ctg<br>Leu | ctg<br>Leu<br>140 | ctg<br>Leu | cgc<br>Arg | cgc<br>Arg | gtg<br>Val | ggc<br>Gly<br>145 | 490 |

| gac<br>Asp | gac<br>Asp | gtg<br>Val | ctg<br>Leu | gtt<br>Val<br>150 | cac<br>His | ctg<br>Leu | ctg<br>Leu | gca<br>Ala | cgc<br>Arg<br>155 | tgc<br>Cys | gcg<br>Ala | ctc<br>Leu | ttt<br>Phe | gtg<br>Val<br>160 | ctg<br>Leu | 538 |

| gtg<br>Val | gct<br>Ala | ccc<br>Pro | agc<br>Ser<br>165 | tgc<br>Cys | gcc<br>Ala | tac<br>Tyr | cag<br>Gln | gtg<br>Val<br>170 | tgc<br>Cys | ggg<br>Gly | ccg<br>Pro | ccg<br>Pro | ctg<br>Leu<br>175 | tac<br>Tyr | cag<br>Gln | 586 |

| ctc<br>Leu | ggc<br>Gly | gct<br>Ala<br>180 | gcc<br>Ala | act<br>Thr | cag<br>Gln | gcc<br>Ala | cgg<br>Arg<br>185 | ccc<br>Pro | ccg<br>Pro | cca<br>Pro | cac<br>His | gct<br>Ala<br>190 | agt<br>Ser | gga<br>Gly | ccc<br>Pro | 634 |

| cga<br>Arg | agg<br>Arg<br>195 | cgt<br>Arg | ctg<br>Leu | gga<br>Gly | tgc<br>Cys | gaa<br>Glu<br>200 | cgg<br>Arg | gcc<br>Ala | tgg<br>Trp | aac<br>Asn | cat<br>His<br>205 | agc<br>Ser | gtc<br>Val | agg<br>Arg | gag<br>Glu | 682 |

| gcc<br>Ala<br>210 | ggg<br>Gly | gtc<br>Val | ccc<br>Pro | ctg<br>Leu | ggc<br>Gly<br>215 | ctg<br>Leu | cca<br>Pro | gcc<br>Ala | ccg<br>Pro | ggt<br>Gly<br>220 | gcg<br>Ala | agg<br>Arg | agg<br>Arg | cgc<br>Arg | ggg<br>Gly<br>225 | 730 |

| ggc<br>Gly | agt<br>Ser | gcc<br>Ala | agc<br>Ser | cga<br>Arg<br>230 | agt<br>Ser | ctg<br>Leu | ccg<br>Pro | ttg<br>Leu | ccc<br>Pro<br>235 | aag<br>Lys | agg<br>Arg | ccc<br>Pro | agg<br>Arg | cgt<br>Arg<br>240 | ggc<br>Gly | 778 |

| gct<br>Ala | gcc<br>Ala | cct<br>Pro | gag<br>Glu<br>245 | ccg<br>Pro | gag<br>Glu | cgg<br>Arg | acg<br>Thr | ccc<br>Pro<br>250 | gtt<br>Val | ggg<br>Gly | cag<br>Gln | ggg<br>Gly | tcc<br>Ser<br>255 | tgg<br>Trp | gcc<br>Ala | 826 |

| cac<br>His | ccg<br>Pro | ggc<br>Gly<br>260 | agg<br>Arg | acg<br>Thr | cgt<br>Arg | gga<br>Gly | ccg<br>Pro<br>265 | agt<br>Ser | gac<br>Asp | cgt<br>Arg | ggt<br>Gly | ttc<br>Phe<br>270 | tgt<br>Cys | gtg<br>Val | gtg<br>Val | 874 |

| tca<br>Ser<br>275 | cct<br>Pro | gcc<br>Ala | aga<br>Arg | ccc<br>Pro | gcc<br>Ala<br>280 | gaa<br>Glu | gaa<br>Glu | gcc<br>Ala | acc<br>Thr | tct<br>Ser<br>285 | ttg<br>Leu | gag<br>Glu | ggt<br>Gly | gcg<br>Ala | ctc<br>Leu | 922 |

| tct<br>Ser | ggc<br>Gly<br>290 | acg<br>Thr | cgc<br>Arg | cac<br>His | tcc<br>Ser<br>295 | cac<br>His | cca<br>Pro | tcc<br>Ser | gtg<br>Val | ggc<br>Gly<br>300 | cgc<br>Arg | cag<br>Gln | cac<br>His | cac<br>His | gcg<br>Ala<br>305 | 970 |

| ggc<br>Gly | ccc<br>Pro | cca<br>Pro | tcc<br>Ser | aca<br>Thr<br>310 | tcg<br>Ser | cgg<br>Arg | cca<br>Pro | cca<br>Pro | cgt<br>Arg<br>315 | ccc<br>Pro | tgg<br>Trp | gac<br>Asp | acg<br>Thr | cct<br>Pro<br>320 | tgt<br>Cys | 1018 |

| ccc<br>Pro | ccg<br>Pro | gtg<br>Val | tac<br>Tyr | gcc<br>Ala | gag<br>Glu | acc<br>Thr | aag<br>Lys | cac<br>His | ttc<br>Phe | ctc<br>Leu | tac<br>Tyr | tcc<br>Ser | tca<br>Ser | ggc<br>Gly | gac<br>Asp | 1066 |

```
                Pro Pro Val Tyr Ala Glu Thr Lys His Phe Leu Tyr Ser Ser Gly Asp
                        325                 330                 335 aag gag cag ctg cgg ccc tcc ttc cta ctc agc tct ctg agg ccc agc        1114
Lys Glu Gln Leu Arg Pro Ser Phe Leu Leu Ser Ser Leu Arg Pro Ser
            340                 345                 350 ctg act ggc gct cgg agg ctc gtg gag acc atc ttt ctg ggt tcc agg        1162
Leu Thr Gly Ala Arg Arg Leu Val Glu Thr Ile Phe Leu Gly Ser Arg
        355                 360                 365 ccc tgg atg cca ggg act ccc cgc agg ttg ccc cgc ctg ccc cag cgc        1210
Pro Trp Met Pro Gly Thr Pro Arg Arg Leu Pro Arg Leu Pro Gln Arg
370                 375                 380                 385 tac tgg caa atg cgg ccc ctg ttt ctg gag ctg ctt ggg aac cac gcg        1258
Tyr Trp Gln Met Arg Pro Leu Phe Leu Glu Leu Leu Gly Asn His Ala
                390                 395                 400 cag tgc ccc tac ggg gtg ctc ctc aag acg cac tgc ccg ctg cga gct        1306
Gln Cys Pro Tyr Gly Val Leu Leu Lys Thr His Cys Pro Leu Arg Ala
            405                 410                 415 gcg gtc acc cca gca gcc ggt gtc tgt gcc cgg gag aag ccc cag ggc        1354
Ala Val Thr Pro Ala Ala Gly Val Cys Ala Arg Glu Lys Pro Gln Gly
        420                 425                 430 tct gtg gcg gcc ccc gag gag gag gac aca gac ccc cgt cgc ctg gtg        1402
Ser Val Ala Ala Pro Glu Glu Glu Asp Thr Asp Pro Arg Arg Leu Val
435                 440                 445 cag ctg ctc cgc cag cac agc agc ccc tgg cag gtg tac ggc ttc gtg        1450
Gln Leu Leu Arg Gln His Ser Ser Pro Trp Gln Val Tyr Gly Phe Val
450                 455                 460                 465 cgg gcc tgc ctg cgc cgg ctg gtg ccc cca ggc ctc tgg ggc tcc agg        1498
Arg Ala Cys Leu Arg Arg Leu Val Pro Pro Gly Leu Trp Gly Ser Arg
                470                 475                 480 cac aac gaa cgc cgc ttc ctc agg aac acc aag aag ttc atc tcc ctg        1546
His Asn Glu Arg Arg Phe Leu Arg Asn Thr Lys Lys Phe Ile Ser Leu
            485                 490                 495 ggg aag cat gcc aag ctc tcg ctg cag gag ctg acg tgg aag atg agc        1594
Gly Lys His Ala Lys Leu Ser Leu Gln Glu Leu Thr Trp Lys Met Ser
        500                 505                 510 gtg cgg gac tgc gct tgg ctg cgc agg agc cca ggg gtt ggc tgt gtt        1642
Val Arg Asp Cys Ala Trp Leu Arg Arg Ser Pro Gly Val Gly Cys Val
515                 520                 525 ccg gcc gca gag cac cgt ctg cgt gag gag atc ctg gcc aag ttc ctg        1690
Pro Ala Ala Glu His Arg Leu Arg Glu Glu Ile Leu Ala Lys Phe Leu
530                 535                 540                 545 cac tgg ctg atg agt gtg tac gtc gtc gag ctg ctc agg tct ttc ttt        1738
His Trp Leu Met Ser Val Tyr Val Val Glu Leu Leu Arg Ser Phe Phe
                550                 555                 560 tat gtc acg gag acc acg ttt caa aag aac agg ctc ttt ttc tac cgg        1786
Tyr Val Thr Glu Thr Thr Phe Gln Lys Asn Arg Leu Phe Phe Tyr Arg
            565                 570                 575 aag agt gtc tgg agc aag ttg caa agc att gga atc aga cag cac ttg        1834
Lys Ser Val Trp Ser Lys Leu Gln Ser Ile Gly Ile Arg Gln His Leu
        580                 585                 590 aag agg gtg cag ctg cgg gag ctg tcg gaa gca gag gtc agg cag cat        1882
Lys Arg Val Gln Leu Arg Glu Leu Ser Glu Ala Glu Val Arg Gln His
595                 600                 605 cgg gaa gcc agg ccc gcc ctg ctg acg tcc aga ctc cgc ttc atc ccc        1930
Arg Glu Ala Arg Pro Ala Leu Leu Thr Ser Arg Leu Arg Phe Ile Pro
610                 615                 620                 625 aag cct gac ggg ctg cgg ccg att gtg aac atg gac tac gtc gtg gga        1978
Lys Pro Asp Gly Leu Arg Pro Ile Val Asn Met Asp Tyr Val Val Gly
                630                 635                 640 gcc aga acg ttc cgc aga gaa aag agg gcc gag cgt ctc acc tcg agg        2026
```

-continued

```
            Ala Arg Thr Phe Arg Arg Glu Lys Arg Ala Glu Arg Leu Thr Ser Arg
                            645                 650                 655 gtg aag gca ctg ttc agc gtg ctc aac tac gag cgg gcg cgg cgc ccc              2074
Val Lys Ala Leu Phe Ser Val Leu Asn Tyr Glu Arg Ala Arg Arg Pro
            660                 665                 670 ggc ctc ctg ggc gcc tct gtg ctg ggc ctg gac gat atc cac agg gcc              2122
Gly Leu Leu Gly Ala Ser Val Leu Gly Leu Asp Asp Ile His Arg Ala
    675                 680                 685 tgg cgc acc ttc gtg ctg cgt gtg cgg gcc cag gac ccg ccg cct gag              2170
Trp Arg Thr Phe Val Leu Arg Val Arg Ala Gln Asp Pro Pro Pro Glu
690                 695                 700                 705 ctg tac ttt gtc aag gtg gat gtg acg ggc gcg tac gac acc atc ccc              2218
Leu Tyr Phe Val Lys Val Asp Val Thr Gly Ala Tyr Asp Thr Ile Pro
                710                 715                 720 cag gac agg ctc acg gag gtc atc gcc agc atc atc aaa ccc cag aac              2266
Gln Asp Arg Leu Thr Glu Val Ile Ala Ser Ile Ile Lys Pro Gln Asn
            725                 730                 735 acg tac tgc gtg cgt cgg tat gcc gtg gtc cag aag gcc gcc cat ggg              2314
Thr Tyr Cys Val Arg Arg Tyr Ala Val Val Gln Lys Ala Ala His Gly
        740                 745                 750 cac gtc cgc aag gcc ttc aag agc cac gtc tct acc ttg aca gac ctc              2362
His Val Arg Lys Ala Phe Lys Ser His Val Ser Thr Leu Thr Asp Leu
    755                 760                 765 cag ccg tac atg cga cag ttc gtg gct cac ctg cag gag acc agc ccg              2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc              2458
Leu Arg Asp Ala Val Val Ile Glu Gln Ser Ser Ser Leu Asn Glu Ala
                790                 795                 800 agc agt ggc ctc ttc gac gtc ttc cta cgc ttc atg tgc cac cac gcc              2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag              2554
Val Arg Ile Arg Gly Lys Ser Tyr Val Gln Cys Gln Gly Ile Pro Gln
        820                 825                 830 ggc tcc atc ctc tcc acg ctg ctc tgc agc ctg tgc tac ggc gac atg              2602
Gly Ser Ile Leu Ser Thr Leu Leu Cys Ser Leu Cys Tyr Gly Asp Met
    835                 840                 845 gag aac aag ctg ttt gcg ggg att cgg cgg gac ggg ctg ctc ctg cgt              2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa              2698
Leu Val Asp Asp Phe Leu Leu Val Thr Pro His Leu Thr His Ala Lys
                870                 875                 880 acc ttc ctc agg acc ctg gtc cga ggt gtc cct gag tat ggc tgc gtg              2746
Thr Phe Leu Arg Thr Leu Val Arg Gly Val Pro Glu Tyr Gly Cys Val
            885                 890                 895 gtg aac ttg cgg aag aca gtg gtg aac ttc cct gta gaa gac gag gcc              2794
Val Asn Leu Arg Lys Thr Val Val Asn Phe Pro Val Glu Asp Glu Ala
        900                 905                 910 ctg ggt ggc acg gct ttt gtt cag atg ccg gcc cac ggc cta ttc ccc              2842
Leu Gly Gly Thr Ala Phe Val Gln Met Pro Ala His Gly Leu Phe Pro
    915                 920                 925 tgg tgc ggc ctg ctg ctg gat acc cgg acc ctg gag gtg cag agc gac              2890
Trp Cys Gly Leu Leu Leu Asp Thr Arg Thr Leu Glu Val Gln Ser Asp
930                 935                 940                 945 tac tcc agc tat gcc cgg acc tcc atc aga gcc agt ctc acc ttc aac              2938
Tyr Ser Ser Tyr Ala Arg Thr Ser Ile Arg Ala Ser Leu Thr Phe Asn
                950                 955                 960 cgc ggc ttc aag gct ggg agg aac atg cgt gcg aaa ctc ttt ggg gtc              2986
```

```
                Arg Gly Phe Lys Ala Gly Arg Asn Met Arg Arg Lys Leu Phe Gly Val
                                965                 970                 975 ttg cgg ctg aag tgt cac agc ctg ttt ctg gat ttg cag gtg aac agc           3034
Leu Arg Leu Lys Cys His Ser Leu Phe Leu Asp Leu Gln Val Asn Ser
        980                 985                 990 ctc cag acg gtg tgc acc aac atc tac aag atc ctc ctg ctg cag gcg           3082
Leu Gln Thr Val Cys Thr Asn Ile Tyr Lys Ile Leu Leu Leu Gln Ala
    995                 1000                1005 tac agg ttt cac gca tgt gtg ctg cag ctc cca ttt cat cag caa               3127
Tyr Arg Phe His Ala Cys Val Leu Gln Leu Pro Phe His Gln Gln
1010                1015                1020 gtt tgg aag aac ccc aca ttt ttc ctg cgc gtc atc tct gac acg               3172
Val Trp Lys Asn Pro Thr Phe Phe Leu Arg Val Ile Ser Asp Thr
1025                1030                1035 gcc tcc ctc tgc tac tcc atc ctg aaa gcc aag aac gca ggg atg               3217
Ala Ser Leu Cys Tyr Ser Ile Leu Lys Ala Lys Asn Ala Gly Met
1040                1045                1050 tcg ctg ggg gcc aag ggc gcc gcc ggc cct ctg ccc tcc gag gcc               3262
Ser Leu Gly Ala Lys Gly Ala Ala Gly Pro Leu Pro Ser Glu Ala
1055                1060                1065 gtg cag tgg ctg tgc cac caa gca ttc ctg ctc aag ctg act cga               3307
Val Gln Trp Leu Cys His Gln Ala Phe Leu Leu Lys Leu Thr Arg
1070                1075                1080 cac cgt gtc acc tac gtg cca ctc ctg ggg tca ctc agg aca gcc               3352
His Arg Val Thr Tyr Val Pro Leu Leu Gly Ser Leu Arg Thr Ala
1085                1090                1095 cag acg cag ctg agt cgg aag ctc ccg ggg acg acg ctg act gcc               3397
Gln Thr Gln Leu Ser Arg Lys Leu Pro Gly Thr Thr Leu Thr Ala
1100                1105                1110 ctg gag gcc gca gcc aac ccg gca ctg ccc tca gac ttc aag acc               3442
Leu Glu Ala Ala Ala Asn Pro Ala Leu Pro Ser Asp Phe Lys Thr
1115                1120                1125 atc ctg gac tga tggccacccg cccacagcca ggccgagagc agacaccagc               3494
Ile Leu Asp
1130 agccctgtca cgccgggctc tacgtcccag ggagggaggg gcggcccaca cccaggcccg         3554 caccgctggg agtctgaggc ctgagtgagt gtttggccga ggcctgcatg tccggctgaa         3614 ggctgagtgt ccggctgagg cctgagcgag tgtccagcca agggctgagt gtccagcaca         3674 cctgccgtct tcacttcccc acaggctggc gctcggctcc accccagggc cagcttttcc         3734 tcaccaggag cccggcttcc actccccaca taggaatagt ccatcccag attcgccatt         3794 gttcacccct cgccctgccc tcctttgcct tccacccca catccaggt ggagaccctg          3854 agaaggaccc tgggagctct gggaatttgg agtgaccaaa ggtgtgccct gtacacaggc         3914 gaggaccctg cacctggatg ggggtccctg tgggtcaaat tgggggagg tgctgtggga         3974 gtaaaatact gaatatatga gttttcagt tttgaaaaaa a                              4015

<210> SEQ ID NO 37
<211> LENGTH: 1132
<212> TYPE: PRT
<213> ORGANISM: Homo sapiens

<400> SEQUENCE: 37

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
```

-continued

```
                35                  40                  45
Ala Leu Val Ala Gln Cys Leu Val Cys Val Pro Trp Asp Ala Arg Pro
 50                  55                  60
Pro Pro Ala Ala Pro Ser Phe Arg Gln Val Ser Cys Leu Lys Glu Leu
 65                  70                  75                  80
Val Ala Arg Val Leu Gln Arg Leu Cys Glu Arg Gly Ala Lys Asn Val
                 85                  90                  95
Leu Ala Phe Gly Phe Ala Leu Leu Asp Gly Ala Arg Gly Gly Pro Pro
                100                 105                 110
Glu Ala Phe Thr Thr Ser Val Arg Ser Tyr Leu Pro Asn Thr Val Thr
                115                 120                 125
Asp Ala Leu Arg Gly Ser Gly Ala Trp Gly Leu Leu Arg Arg Val
130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
                180                 185                 190
Pro Arg Arg Arg Leu Gly Cys Glu Arg Ala Trp Asn His Ser Val Arg
                195                 200                 205
Glu Ala Gly Val Pro Leu Gly Leu Pro Ala Pro Gly Ala Arg Arg Arg
                210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
                260                 265                 270
Val Ser Pro Ala Arg Pro Ala Glu Glu Ala Thr Ser Leu Glu Gly Ala
                275                 280                 285
Leu Ser Gly Thr Arg His Ser His Pro Ser Val Gly Arg Gln His His
                290                 295                 300
Ala Gly Pro Pro Ser Thr Ser Arg Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
                340                 345                 350
Ser Leu Thr Gly Ala Arg Arg Leu Val Glu Thr Ile Phe Leu Gly Ser
                355                 360                 365
Arg Pro Trp Met Pro Gly Thr Pro Arg Arg Leu Pro Arg Leu Pro Gln
370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
Gly Ser Val Ala Ala Pro Glu Glu Asp Thr Asp Pro Arg Arg Leu
                435                 440                 445
Val Gln Leu Leu Arg Gln His Ser Ser Pro Trp Gln Val Tyr Gly Phe
450                 455                 460
```

-continued

```
Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
            485                 490                 495

Leu Gly Lys His Ala Lys Leu Ser Leu Gln Glu Leu Thr Trp Lys Met
        500                 505                 510

Ser Val Arg Asp Cys Ala Trp Leu Arg Arg Ser Pro Gly Val Gly Cys
    515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
            565                 570                 575

Arg Lys Ser Val Trp Ser Lys Leu Gln Ser Ile Gly Ile Arg Gln His
        580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
            645                 650                 655

Arg Val Lys Ala Leu Phe Ser Val Leu Asn Tyr Glu Arg Ala Arg Arg
        660                 665                 670

Pro Gly Leu Leu Gly Ala Ser Val Leu Gly Leu Asp Asp Ile His Arg
    675                 680                 685

Ala Trp Arg Thr Phe Val Leu Arg Val Arg Ala Gln Asp Pro Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735

Asn Thr Tyr Cys Val Arg Arg Tyr Ala Val Val Gln Lys Ala Ala His
        740                 745                 750

Gly His Val Arg Lys Ala Phe Lys Ser His Val Ser Thr Leu Thr Asp
    755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
        820                 825                 830

Gln Gly Ser Ile Leu Ser Thr Leu Leu Cys Ser Leu Cys Tyr Gly Asp
    835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895
```

```
Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 38
<211> LENGTH: 4009
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (59)..(3448)

<400> SEQUENCE: 38
caggcagcgc tgcgtcctgc tgcgcacgtg ggaagccctg gccccggcca ccccgcg       58 atg ccg cgc gct ccc cgc tgc cga gcc gtg cgc tcc ctg ctg cgc agc    106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg    154
His Tyr Arg Glu Val Leu Pro Leu Ala Thr Phe Val Arg Arg Leu Gly
                20                  25                  30 ccc cag ggc tgg cgg ctg gtg cag cgc ggg gac ccg gcg gct ttc cgc    202
Pro Gln Gly Trp Arg Leu Val Gln Arg Gly Asp Pro Ala Ala Phe Arg
            35                  40                  45 gcg ctg gtg gcc cag tgc ctg gtg tgc gtg ccc tgg gac gca cgg ccg    250
Ala Leu Val Ala Gln Cys Leu Val Cys Val Pro Trp Asp Ala Arg Pro
        50                  55                  60
```

```
ccc ccc gcc gcc ccc tcc ttc cgc cag gtg tcc tgc ctg aag gag ctg        298
Pro Pro Ala Ala Pro Ser Phe Arg Gln Val Ser Cys Leu Lys Glu Leu
65              70                  75                  80 gtg gcc cga gtg ctg cag agg ctg tgc gag cgc ggc gcg aag aac gtg        346
Val Ala Arg Val Leu Gln Arg Leu Cys Glu Arg Gly Ala Lys Asn Val
                    85                  90                  95 ctg gcc ttc ggc ttc gcg ctg ctg gac ggg gcc cgc ggg ggc ccc ccc        394
Leu Ala Phe Gly Phe Ala Leu Leu Asp Gly Ala Arg Gly Gly Pro Pro
                100                 105                 110 gag gcc ttc acc acc agc gtg cgc agc tac ctg ccc aac acg gtg acc        442
Glu Ala Phe Thr Thr Ser Val Arg Ser Tyr Leu Pro Asn Thr Val Thr
            115                 120                 125 gac gca ctg cgg ggg agc ggg gcg tgg ggg ctg ctg cgc cgc gtg            490
Asp Ala Leu Arg Gly Ser Gly Ala Trp Gly Leu Leu Arg Arg Val
        130                 135                 140 ggc gac gac gtg ctg gtt cac ctg ctg gca cgc tgc gcg ctc ttt gtg        538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac        586
Leu Val Ala Pro Ser Cys Ala Tyr Gln Val Cys Gly Pro Pro Leu Tyr
                165                 170                 175 cag ctc ggc gct gcc act cag gcc cgg ccc ccg cac gct agt gga            634
Gln Leu Gly Ala Ala Thr Gln Ala Arg Pro Pro His Ala Ser Gly
        180                 185                 190 ccc cga agg cgt ctg gga tgc gaa cgg gcc tgg aac cat agc gtc agg        682
Pro Arg Arg Arg Leu Gly Cys Glu Arg Ala Trp Asn His Ser Val Arg
                195                 200                 205 gag gcc ggg gtc ccc ctg ggc ctg cca gcc ccg ggt gcg agg agg cgc        730
Glu Ala Gly Val Pro Leu Gly Leu Pro Ala Pro Gly Ala Arg Arg Arg
            210                 215                 220 ggg ggc agt gcc agc cga agt ctg ccg ttg ccc aag agg ccc agg cgt        778
Gly Gly Ser Ala Ser Arg Ser Leu Pro Leu Pro Lys Arg Pro Arg Arg
225                 230                 235                 240 ggc gct gcc cct gag ccg gag cgg acg ccc gtt ggg cag ggg tcc tgg        826
Gly Ala Ala Pro Glu Pro Glu Arg Thr Pro Val Gly Gln Gly Ser Trp
                245                 250                 255 gcc cac ccg ggc agg acg cgt gga ccg agt gac cgt ggt ttc tgt gtg        874
Ala His Pro Gly Arg Thr Arg Gly Pro Ser Asp Arg Gly Phe Cys Val
        260                 265                 270 gtg tca cct gcc aga ccc gcc gaa gaa gcc acc tct ttg gag ggt gcg        922
Val Ser Pro Ala Arg Pro Ala Glu Glu Ala Thr Ser Leu Glu Gly Ala
                275                 280                 285 ctc tct ggc acg cgc cac tcc cac cca tcc gtg ggc cgc cag cac cac        970
Leu Ser Gly Thr Arg His Ser His Pro Ser Val Gly Arg Gln His His
            290                 295                 300 gcg ggc ccc cca tcc aca tcg cgg cca cca cgt ccc tgg gac acg cct        1018
Ala Gly Pro Pro Ser Thr Ser Arg Pro Pro Arg Pro Trp Asp Thr Pro
305                 310                 315                 320 tgt ccc ccg gtg tac gcc gag acc aag cac ttc ctc tac tcc tca ggc        1066
Cys Pro Pro Val Tyr Ala Glu Thr Lys His Phe Leu Tyr Ser Ser Gly
                325                 330                 335 gac aag gag cag ctg cgg ccc tcc ttc cta ctc agc tct ctg agg ccc        1114
Asp Lys Glu Gln Leu Arg Pro Ser Phe Leu Leu Ser Ser Leu Arg Pro
            340                 345                 350 agc ctg act ggc gct cgg agg ctc gtg gag acc atc ttt ctg ggt tcc        1162
Ser Leu Thr Gly Ala Arg Arg Leu Val Glu Thr Ile Phe Leu Gly Ser
        355                 360                 365 agg ccc tgg atg cca ggg act ccc cgc agg ttg ccc cgc ctg ccc cag        1210
Arg Pro Trp Met Pro Gly Thr Pro Arg Arg Leu Pro Arg Leu Pro Gln
370                 375                 380
```

```
cgc tac tgg caa atg cgg ccc ctg ttt ctg gag ctg ctt ggg aac cac    1258
Arg Tyr Trp Gln Met Arg Pro Leu Phe Leu Glu Leu Leu Gly Asn His
385                 390                 395                 400 gcg cag tgc ccc tac ggg gtg ctc ctc aag acg cac tgc ccg ctg cga    1306
Ala Gln Cys Pro Tyr Gly Val Leu Leu Lys Thr His Cys Pro Leu Arg
                405                 410                 415 gct gcg gtc acc cca gca gcc ggt gtc tgt gcc cgg gag aag ccc cag    1354
Ala Ala Val Thr Pro Ala Ala Gly Val Cys Ala Arg Glu Lys Pro Gln
420                 425                 430 ggc tct gtg gcg gcc ccc gag gag gag gac aca gac ccc cgt cgc ctg    1402
Gly Ser Val Ala Ala Pro Glu Glu Glu Asp Thr Asp Pro Arg Arg Leu
    435                 440                 445 gtg cag ctg ctc cgc cag cac agc agc ccc tgg cag gtg tac ggc ttc    1450
Val Gln Leu Leu Arg Gln His Ser Ser Pro Trp Gln Val Tyr Gly Phe
450                 455                 460 gtg cgg gcc tgc ctg cgc cgg ctg gtg ccc cca ggc ctc tgg ggc tcc    1498
Val Arg Ala Cys Leu Arg Arg Leu Val Pro Pro Gly Leu Trp Gly Ser
465                 470                 475                 480 agg cac aac gaa cgc cgc ttc ctc agg aac acc aag aag ttc atc tcc    1546
Arg His Asn Glu Arg Arg Phe Leu Arg Asn Thr Lys Lys Phe Ile Ser
                485                 490                 495 ctg ggg aag cat gcc aag ctc tcg ctg cag gag ctg acg tgg aag atg    1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt    1642
Ser Val Arg Asp Cys Ala Trp Leu Arg Arg Ser Pro Gly Val Gly Cys
        515                 520                 525 gtt ccg gcc gca gag cac cgt ctg cgt gag gag atc ctg gcc aag ttc    1690
Val Pro Ala Ala Glu His Arg Leu Arg Glu Glu Ile Leu Ala Lys Phe
530                 535                 540 ctg cac tgg ctg atg agt gtg tac gtc gtc gag ctg ctc agg tct ttc    1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac    1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac    1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag    1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc    1930
His Arg Glu Ala Arg Pro Ala Leu Leu Thr Ser Arg Leu Arg Phe Ile
610                 615                 620 ccc aag cct gac ggg ctg cgg ccg att gtg aac atg gac tac gtc gtg    1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg    2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
            660                 665                 670 ccc ggc ctc ctg ggc gcc tct gtg ctg ggc ctg gac gat atc cac agg    2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct    2170
Ala Trp Arg Thr Phe Val Leu Arg Val Arg Ala Gln Asp Pro Pro Pro
690                 695                 700
```

```
                                                            -continued gag ctg tac ttt gtc aag gtg gat gtg acg ggc gcg tac gac acc atc    2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag    2266
Pro Gln Asp Arg Leu Thr Glu Val Ile Ala Ser Ile Ile Lys Pro Gln
                725                 730                 735 aac acg tac tgc gtg cgt cgg tat gcc gtg gtc cag aag gcc gcc cat    2314
Asn Thr Tyr Cys Val Arg Arg Tyr Ala Val Val Gln Lys Ala Ala His
        740                 745                 750 ggg cac gtc cgc aag gcc ttc aag agc cac gtc tct acc ttg aca gac    2362
Gly His Val Arg Lys Ala Phe Lys Ser His Val Ser Thr Leu Thr Asp
    755                 760                 765 ctc cag ccg tac atg cga cag ttc gtg gct cac ctg cag gag acc agc    2410
Leu Gln Pro Tyr Met Arg Gln Phe Val Ala His Leu Gln Glu Thr Ser
770                 775                 780 ccg ctg agg gat gcc gtc gtc atc gag cag agc tcc tcc ctg aat gag    2458
Pro Leu Arg Asp Ala Val Val Ile Glu Gln Ser Ser Ser Leu Asn Glu
785                 790                 795                 800 gcc agc agt ggc ctc ttc gac gtc ttc cta cgc ttc atg tgc cac cac    2506
Ala Ser Ser Gly Leu Phe Asp Val Phe Leu Arg Phe Met Cys His His
                805                 810                 815 gcc gtg cgc atc agg ggc aag tcc tac gtc cag tgc cag ggg atc ccg    2554
Ala Val Arg Ile Arg Gly Lys Ser Tyr Val Gln Cys Gln Gly Ile Pro
        820                 825                 830 cag ggc tcc atc ctc tcc acg ctg ctc tgc agc ctg tgc tac ggc gac    2602
Gln Gly Ser Ile Leu Ser Thr Leu Leu Cys Ser Leu Cys Tyr Gly Asp
    835                 840                 845 atg gag aac aag ctg ttt gcg ggg att cgg cgg gac ggg ctg ctc ctg    2650
Met Glu Asn Lys Leu Phe Ala Gly Ile Arg Arg Asp Gly Leu Leu Leu
850                 855                 860 cgt ttg ttc ttg ttg gtg aca cct cac ctc acc cac gcg aaa acc ttc    2698
Arg Leu Phe Leu Leu Val Thr Pro His Leu Thr His Ala Lys Thr Phe
865                 870                 875                 880 ctc agg acc ctg gtc cga ggt gtc cct gag tat ggc tgc gtg gtg aac    2746
Leu Arg Thr Leu Val Arg Gly Val Pro Glu Tyr Gly Cys Val Val Asn
                885                 890                 895 ttg cgg aag aca gtg gtg aac ttc cct gta gaa gac gag gcc ctg ggt    2794
Leu Arg Lys Thr Val Val Asn Phe Pro Val Glu Asp Glu Ala Leu Gly
        900                 905                 910 ggc acg gct ttt gtt cag atg ccg gcc cac ggc cta ttc ccc tgg tgc    2842
Gly Thr Ala Phe Val Gln Met Pro Ala His Gly Leu Phe Pro Trp Cys
    915                 920                 925 ggc ctg ctg ctg gat acc cgg acc ctg gag gtg cag agc gac tac tcc    2890
Gly Leu Leu Leu Asp Thr Arg Thr Leu Glu Val Gln Ser Asp Tyr Ser
930                 935                 940 agc tat gcc cgg acc tcc atc aga gcc agt ctc acc ttc aac cgc ggc    2938
Ser Tyr Ala Arg Thr Ser Ile Arg Ala Ser Leu Thr Phe Asn Arg Gly
945                 950                 955                 960 ttc aag gct ggg agg aac atg cgt cgc aaa ctc ttt ggg gtc ttg cgg    2986
Phe Lys Ala Gly Arg Asn Met Arg Arg Lys Leu Phe Gly Val Leu Arg
                965                 970                 975 ctg aag tgt cac agc ctg ttt ctg gat ttg cag gtg aac agc ctc cag    3034
Leu Lys Cys His Ser Leu Phe Leu Asp Leu Gln Val Asn Ser Leu Gln
        980                 985                 990 acg gtg tgc acc aac atc tac aag atc ctc ctg ctg cag gcg tac agg    3082
Thr Val Cys Thr Asn Ile Tyr Lys Ile Leu Leu Leu Gln Ala Tyr Arg
    995                 1000                1005 ttt cac gca tgt gtg ctg cag ctc cca ttt cat cag caa gtt tgg       3127
Phe His Ala Cys Val Leu Gln Leu Pro Phe His Gln Gln Val Trp
    1010                1015                1020
```

```
aag aac ccc aca ttt ttc ctg cgc gtc atc tct gac acg gcc tcc    3172
Lys Asn Pro Thr Phe Phe Leu Arg Val Ile Ser Asp Thr Ala Ser
    1025                1030                1035 ctc tgc tac tcc atc ctg aaa gcc aag aac gca ggg atg tcg ctg    3217
Leu Cys Tyr Ser Ile Leu Lys Ala Lys Asn Ala Gly Met Ser Leu
    1040                1045                1050 ggg gcc aag ggc gcc gcc ggc cct ctg ccc tcc gag gcc gtg cag    3262
Gly Ala Lys Gly Ala Ala Gly Pro Leu Pro Ser Glu Ala Val Gln
    1055                1060                1065 tgg ctg tgc cac caa gca ttc ctg ctc aag ctg act cga cac cgt    3307
Trp Leu Cys His Gln Ala Phe Leu Leu Lys Leu Thr Arg His Arg
    1070                1075                1080 gtc acc tac gtg cca ctc ctg ggg tca ctc agg aca gcc cag acg    3352
Val Thr Tyr Val Pro Leu Leu Gly Ser Leu Arg Thr Ala Gln Thr
    1085                1090                1095 cag ctg agt cgg aag ctc ccg ggg acg acg ctg act gcc ctg gag    3397
Gln Leu Ser Arg Lys Leu Pro Gly Thr Thr Leu Thr Ala Leu Glu
    1100                1105                1110 gcc gca gcc aac ccg gca ctg ccc tca gac ttc aag acc atc ctg    3442
Ala Ala Ala Asn Pro Ala Leu Pro Ser Asp Phe Lys Thr Ile Leu
    1115                1120                1125 gac tga tggccaccg cccacagcca ggccgagagc agacaccagc agccctgtca    3498
Asp cgccgggctc tacgtcccag ggagggaggg gcggcccaca cccaggcccg caccgctggg    3558
agtctgaggc ctgagtgagt gtttggccga ggcctgcatg tccggctgaa ggctgagtgt    3618
ccggctgagg cctgagcgag tgtccagcca agggctgagt gtccagcaca cctgccgtct    3678
tcacttcccc acaggctggc gctcggctcc accccagggc cagcttttcc tcaccaggag    3738
cccggcttcc actccccaca taggaatagt ccatccccag attcgccatt gttcacccct    3798
cgccctgccc tcctttgcct tccacccca ccatccaggt ggagaccctg agaaggaccc    3858
tgggagctct gggaatttgg agtgaccaaa ggtgtgccct gtacacaggc gaggaccctg    3918
cacctggatg ggggtccctg tgggtcaaat tgggggagg tgctgtggga gtaaaatact    3978
gaatatatga gttttcagt tttgaaaaaa a                                    4009
```

<210> SEQ ID NO 39
<211> LENGTH: 1129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
```

-continued

```
                100                 105                 110
Glu Ala Phe Thr Thr Ser Val Arg Ser Tyr Leu Pro Asn Thr Val Thr
            115                 120                 125
Asp Ala Leu Arg Gly Ser Gly Ala Trp Gly Leu Leu Leu Arg Arg Val
        130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
            180                 185                 190
Pro Arg Arg Leu Gly Cys Glu Arg Ala Trp Asn His Ser Val Arg
        195                 200                 205
Glu Ala Gly Val Pro Leu Gly Leu Pro Ala Pro Gly Ala Arg Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Ala Thr Ser Leu Glu Gly Ala
        275                 280                 285
Leu Ser Gly Thr Arg His Ser His Pro Ser Val Gly Arg Gln His His
    290                 295                 300
Ala Gly Pro Pro Ser Thr Ser Arg Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
        355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
        515                 520                 525
```

```
Val Pro Ala Ala Glu His Arg Leu Arg Glu Glu Ile Leu Ala Lys Phe
530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
595                 600                 605
His Arg Glu Ala Arg Pro Ala Leu Leu Thr Ser Arg Leu Arg Phe Ile
610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
850                 855                 860
Arg Leu Phe Leu Leu Val Thr Pro His Leu Thr His Ala Lys Thr Phe
865                 870                 875                 880
Leu Arg Thr Leu Val Arg Gly Val Pro Glu Tyr Gly Cys Val Val Asn
                885                 890                 895
Leu Arg Lys Thr Val Val Asn Phe Pro Val Glu Asp Glu Ala Leu Gly
            900                 905                 910
Gly Thr Ala Phe Val Gln Met Pro Ala His Gly Leu Phe Pro Trp Cys
        915                 920                 925
Gly Leu Leu Leu Asp Thr Arg Thr Leu Glu Val Gln Ser Asp Tyr Ser
930                 935                 940
Ser Tyr Ala Arg Thr Ser Ile Arg Ala Ser Leu Thr Phe Asn Arg Gly
945                 950                 955                 960
```

```
Phe Lys Ala Gly Arg Asn Met Arg Arg Lys Leu Phe Gly Val Leu Arg
            965                 970                 975

Leu Lys Cys His Ser Leu Phe Leu Asp Leu Gln Val Asn Ser Leu Gln
            980                 985                 990

Thr Val Cys Thr Asn Ile Tyr Lys Ile Leu Leu Leu Gln Ala Tyr Arg
            995                 1000                1005

Phe His Ala Cys Val Leu Gln Leu Pro Phe His Gln Gln Val Trp
        1010                1015                1020

Lys Asn Pro Thr Phe Phe Leu Arg Val Ile Ser Asp Thr Ala Ser
        1025                1030                1035

Leu Cys Tyr Ser Ile Leu Lys Ala Lys Asn Ala Gly Met Ser Leu
        1040                1045                1050

Gly Ala Lys Gly Ala Ala Gly Pro Leu Pro Ser Glu Ala Val Gln
        1055                1060                1065

Trp Leu Cys His Gln Ala Phe Leu Leu Lys Leu Thr Arg His Arg
        1070                1075                1080

Val Thr Tyr Val Pro Leu Leu Gly Ser Leu Arg Thr Ala Gln Thr
        1085                1090                1095

Gln Leu Ser Arg Lys Leu Pro Gly Thr Thr Leu Thr Ala Leu Glu
        1100                1105                1110

Ala Ala Ala Asn Pro Ala Leu Pro Ser Asp Phe Lys Thr Ile Leu
        1115                1120                1125

Asp
```

<210> SEQ ID NO 40
<211> LENGTH: 3991
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (59)..(3430)

<400> SEQUENCE: 40

```
caggcagcgc tgcgtcctgc tgcgcacgtg ggaagccctg gccccggcca ccccgcg        58 atg ccg cgc gct ccc cgc tgc cga gcc gtg cgc tcc ctg ctg cgc agc     106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg     154
His Tyr Arg Glu Val Leu Pro Leu Ala Thr Phe Val Arg Arg Leu Gly
            20                  25                  30 ccc cag ggc tgg cgg ctg gtg cag cgc ggg gac ccg gcg gct ttc cgc     202
Pro Gln Gly Trp Arg Leu Val Gln Arg Gly Asp Pro Ala Ala Phe Arg
        35                  40                  45 gcg ctg gtg gcc cag tgc ctg gtg tgc gtg ccc tgg gac gca cgg ccg     250
Ala Leu Val Ala Gln Cys Leu Val Cys Val Pro Trp Asp Ala Arg Pro
    50                  55                  60 ccc ccc gcc gcc ccc tcc ttc cgc cag gtg tcc tgc ctg aag gag ctg     298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg     346
Val Ala Arg Val Leu Gln Arg Leu Cys Glu Arg Gly Ala Lys Asn Val
                85                  90                  95 ctg gcc ttc ggc ttc gcg ctg ctg gac ggg gcc cgc ggg ggc ccc ccc     394
Leu Ala Phe Gly Phe Ala Leu Leu Asp Gly Ala Arg Gly Gly Pro Pro
            100                 105                 110
```

| | | |
|---|---|---|
| gag gcc ttc acc acc agc gtg cgc agc tac ctg ccc aac acg gtg acc<br>Glu Ala Phe Thr Thr Ser Val Arg Ser Tyr Leu Pro Asn Thr Val Thr<br>115                      120                  125 | 442 |
| gac gca ctg cgg ggg agc ggg gcg tgg ggg ctg ctg ctg cgc cgc gtg<br>Asp Ala Leu Arg Gly Ser Gly Ala Trp Gly Leu Leu Leu Arg Arg Val<br>    130                  135                  140 | 490 |
| ggc gac gac gtg ctg gtt cac ctg ctg gca cgc tgc gcg ctc ttt gtg<br>Gly Asp Asp Val Leu Val His Leu Leu Ala Arg Cys Ala Leu Phe Val<br>145                      150                  155                  160 | 538 |
| ctg gtg gct ccc agc tgc gcc tac cag gtg tgc ggg ccg ccg ctg tac<br>Leu Val Ala Pro Ser Cys Ala Tyr Gln Val Cys Gly Pro Pro Leu Tyr<br>                  165                  170                  175 | 586 |
| cag ctc ggc gct gcc act cag gcc cgg ccc cca cac gct agt gga<br>Gln Leu Gly Ala Ala Thr Gln Ala Arg Pro Pro Pro His Ala Ser Gly<br>            180                  185                  190 | 634 |
| ccc cga agg cgt ctg gga tgc gaa cgg gcc tgg aac cat agc gtc agg<br>Pro Arg Arg Arg Leu Gly Cys Glu Arg Ala Trp Asn His Ser Val Arg<br>        195                  200                  205 | 682 |
| gag gcc ggg gtc ccc ctg ggc ctg cca gcc ccg ggt gcg agg agg cgc<br>Glu Ala Gly Val Pro Leu Gly Leu Pro Ala Pro Gly Ala Arg Arg Arg<br>210                      215                  220 | 730 |
| ggg ggc agt gcc agc cga agt ctg ccg ttg ccc aag agg ccc agg cgt<br>Gly Gly Ser Ala Ser Arg Ser Leu Pro Leu Pro Lys Arg Pro Arg Arg<br>225                      230                  235                  240 | 778 |
| ggc gct gcc cct gag ccg gag cgg acg ccc gtt ggg cag ggg tcc tgg<br>Gly Ala Ala Pro Glu Pro Glu Arg Thr Pro Val Gly Gln Gly Ser Trp<br>                  245                  250                  255 | 826 |
| gcc cac ccg ggc agg acg cgt gga ccg agt gac cgt ggt ttc tgt gtg<br>Ala His Pro Gly Arg Thr Arg Gly Pro Ser Asp Arg Gly Phe Cys Val<br>            260                  265                  270 | 874 |
| gtg tca cct gcc aga ccc gcc gaa gaa gcc acc tct ttg gag ggt gcg<br>Val Ser Pro Ala Arg Pro Ala Glu Glu Ala Thr Ser Leu Glu Gly Ala<br>275                      280                  285 | 922 |
| ctc tct ggc acg cgc cac tcc cac cca tcc gtg ggc cgc cag cac cac<br>Leu Ser Gly Thr Arg His Ser His Pro Ser Val Gly Arg Gln His His<br>    290                  295                  300 | 970 |
| gcg ggc ccc cca tcc aca tcg cgg cca cca cgt ccc tgg gac acg cct<br>Ala Gly Pro Pro Ser Thr Ser Arg Pro Pro Arg Pro Trp Asp Thr Pro<br>305                      310                  315                  320 | 1018 |
| tgt ccc ccg gtg tac gcc gag acc aag cac ttc ctc tac tcc tca ggc<br>Cys Pro Pro Val Tyr Ala Glu Thr Lys His Phe Leu Tyr Ser Ser Gly<br>                  325                  330                  335 | 1066 |
| gac aag gag cag ctg cgg ccc tcc ttc cta ctc agc tct ctg agg ccc<br>Asp Lys Glu Gln Leu Arg Pro Ser Phe Leu Leu Ser Ser Leu Arg Pro<br>            340                  345                  350 | 1114 |
| agc ctg act ggc gct cgg agg ctc gtg gag acc atc ttt ctg ggt tcc<br>Ser Leu Thr Gly Ala Arg Arg Leu Val Glu Thr Ile Phe Leu Gly Ser<br>    355                  360                  365 | 1162 |
| agg ccc tgg atg cca ggg act ccc cgc agg ttg ccc cgc ctg ccc cag<br>Arg Pro Trp Met Pro Gly Thr Pro Arg Arg Leu Pro Arg Leu Pro Gln<br>370                      375                  380 | 1210 |
| cgc tac tgg caa atg cgg ccc ctg ttt ctg gag ctg ctt ggg aac cac<br>Arg Tyr Trp Gln Met Arg Pro Leu Phe Leu Glu Leu Leu Gly Asn His<br>385                      390                  395                  400 | 1258 |
| gcg cag tgc ccc tac ggg gtg ctc ctc aag acg cac tgc ccg ctg cga<br>Ala Gln Cys Pro Tyr Gly Val Leu Leu Lys Thr His Cys Pro Leu Arg<br>                  405                  410                  415 | 1306 |
| gct gcg gtc acc cca gca gcc ggt gtc tgt gcc cgg gag aag ccc cag<br>Ala Ala Val Thr Pro Ala Ala Gly Val Cys Ala Arg Glu Lys Pro Gln<br>            420                  425                  430 | 1354 |

```
ggc tct gtg gcg gcc ccc gag gag gag gac aca gac ccc cgt cgc ctg    1402
Gly Ser Val Ala Ala Pro Glu Glu Glu Asp Thr Asp Pro Arg Arg Leu
        435                 440                 445 gtg cag ctg ctc cgc cag cac agc agc ccc tgg cag gtg tac ggc ttc    1450
Val Gln Leu Leu Arg Gln His Ser Ser Pro Trp Gln Val Tyr Gly Phe
450                 455                 460 gtg cgg gcc tgc ctg cgc cgg ctg gtg ccc cca ggc ctg tgg ggc tcc    1498
Val Arg Ala Cys Leu Arg Arg Leu Val Pro Pro Gly Leu Trp Gly Ser
465                 470                 475                 480 agg cac aac gaa cgc cgc ttc ctc agg aac acc aag aag ttc atc tcc    1546
Arg His Asn Glu Arg Arg Phe Leu Arg Asn Thr Lys Lys Phe Ile Ser
                485                 490                 495 ctg ggg aag cat gcc aag ctc tcg ctg cag gag ctg acg tgg aag atg    1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt    1642
Ser Val Arg Asp Cys Ala Trp Leu Arg Arg Ser Pro Gly Val Gly Cys
        515                 520                 525 gtt ccg gcc gca gag cac cgt ctg cgt gag gag atc ctg gcc aag ttc    1690
Val Pro Ala Ala Glu His Arg Leu Arg Glu Glu Ile Leu Ala Lys Phe
530                 535                 540 ctg cac tgg ctg atg agt gtg tac gtc gtc gag ctg ctc agg tct ttc    1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac    1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac    1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag    1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc    1930
His Arg Glu Ala Arg Pro Ala Leu Leu Thr Ser Arg Leu Arg Phe Ile
610                 615                 620 ccc aag cct gac ggg ctg cgg ccg att gtg aac atg gac tac gtc gtg    1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg    2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
            660                 665                 670 ccc ggc ctc ctg ggc gcc tct gtg ctg ggc ctg gac gat atc cac agg    2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct    2170
Ala Trp Arg Thr Phe Val Leu Arg Val Arg Ala Gln Asp Pro Pro Pro
690                 695                 700 gag ctg tac ttt gtc aag gtg gat gtg acg ggc gcg tac gac acc atc    2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag    2266
Pro Gln Asp Arg Leu Thr Glu Val Ile Ala Ser Ile Ile Lys Pro Gln
                725                 730                 735 aac acg tac tgc gtg cgt cgg tat gcc gtg gtc cag aag gcc gcc cat    2314
Asn Thr Tyr Cys Val Arg Arg Tyr Ala Val Val Gln Lys Ala Ala His
            740                 745                 750
```

```
ggg cac gtc cgc aag gcc ttc aag agc cac gtc tct acc ttg aca gac      2362
Gly His Val Arg Lys Ala Phe Lys Ser His Val Ser Thr Leu Thr Asp
        755                 760                 765 ctc cag ccg tac atg cga cag ttc gtg gct cac ctg cag gag acc agc      2410
Leu Gln Pro Tyr Met Arg Gln Phe Val Ala His Leu Gln Glu Thr Ser
        770                 775                 780 ccg ctg agg gat gcc gtc gtc atc gag cag agc tcc tcc ctg aat gag      2458
Pro Leu Arg Asp Ala Val Val Ile Glu Gln Ser Ser Ser Leu Asn Glu
785                 790                 795                 800 gcc agc agt ggc ctc ttc gac gtc ttc cta cgc ttc atg tgc cac cac      2506
Ala Ser Ser Gly Leu Phe Asp Val Phe Leu Arg Phe Met Cys His His
                805                 810                 815 gcc gtg cgc atc agg ggc aag tcc tac gtc cag tgc cag ggg atc ccg      2554
Ala Val Arg Ile Arg Gly Lys Ser Tyr Val Gln Cys Gln Gly Ile Pro
        820                 825                 830 cag ggc tcc atc ctc tcc acg ctg ctc tgc agc ctg tgc tac ggc gac      2602
Gln Gly Ser Ile Leu Ser Thr Leu Leu Cys Ser Leu Cys Tyr Gly Asp
            835                 840                 845 atg gag aac aag ctg ttt gcg ggg att cgg cgg gac ggg ctg ctc gtg      2650
Met Glu Asn Lys Leu Phe Ala Gly Ile Arg Arg Asp Gly Leu Leu Val
850                 855                 860 aca cct cac ctc acc cac gcg aaa acc ttc ctc agg acc ctg gtc cga      2698
Thr Pro His Leu Thr His Ala Lys Thr Phe Leu Arg Thr Leu Val Arg
865                 870                 875                 880 ggt gtc cct gag tat ggc tgc gtg gtg aac ttg cgg aag aca gtg gtg      2746
Gly Val Pro Glu Tyr Gly Cys Val Val Asn Leu Arg Lys Thr Val Val
                885                 890                 895 aac ttc cct gta gaa gac gag gcc ctg ggt ggc acg gct ttt gtt cag      2794
Asn Phe Pro Val Glu Asp Glu Ala Leu Gly Gly Thr Ala Phe Val Gln
                900                 905                 910 atg ccg gcc cac ggc cta ttc ccc tgg tgc ggc ctg ctg ctg gat acc      2842
Met Pro Ala His Gly Leu Phe Pro Trp Cys Gly Leu Leu Leu Asp Thr
            915                 920                 925 cgg acc ctg gag gtg cag agc gac tac tcc agc tat gcc cgg acc tcc      2890
Arg Thr Leu Glu Val Gln Ser Asp Tyr Ser Ser Tyr Ala Arg Thr Ser
930                 935                 940 atc aga gcc agt ctc acc ttc aac cgc ggc ttc aag gct ggg agg aac      2938
Ile Arg Ala Ser Leu Thr Phe Asn Arg Gly Phe Lys Ala Gly Arg Asn
945                 950                 955                 960 atg cgt cgc aaa ctc ttt ggg gtc ttg cgg ctg aag tgt cac agc ctg      2986
Met Arg Arg Lys Leu Phe Gly Val Leu Arg Leu Lys Cys His Ser Leu
                965                 970                 975 ttt ctg gat ttg cag gtg aac agc ctc cag acg gtg tgc acc aac atc      3034
Phe Leu Asp Leu Gln Val Asn Ser Leu Gln Thr Val Cys Thr Asn Ile
            980                 985                 990 tac aag atc ctc ctg ctg cag gcg tac agg ttt cac gca tgt gtg ctg      3082
Tyr Lys Ile Leu Leu Leu Gln Ala Tyr Arg Phe His Ala Cys Val Leu
        995                 1000                1005 cag ctc cca ttt cat cag caa gtt tgg aag aac ccc aca ttt ttc          3127
Gln Leu Pro Phe His Gln Gln Val Trp Lys Asn Pro Thr Phe Phe
        1010                1015                1020 ctg cgc gtc atc tct gac acg gcc tcc ctc tgc tac tcc atc ctg          3172
Leu Arg Val Ile Ser Asp Thr Ala Ser Leu Cys Tyr Ser Ile Leu
        1025                1030                1035 aaa gcc aag aac gca ggg atg tcg ctg ggg gcc aag ggc gcc gcc          3217
Lys Ala Lys Asn Ala Gly Met Ser Leu Gly Ala Lys Gly Ala Ala
        1040                1045                1050 ggc cct ctg ccc tcc gag gcc gtg cag tgg ctg tgc cac caa gca          3262
Gly Pro Leu Pro Ser Glu Ala Val Gln Trp Leu Cys His Gln Ala
        1055                1060                1065
```

```
ttc ctg ctc aag ctg act cga cac cgt gtc acc tac gtg cca ctc      3307
Phe Leu Leu Lys Leu Thr Arg His Arg Val Thr Tyr Val Pro Leu
    1070                1075                1080 ctg ggg tca ctc agg aca gcc cag acg cag ctg agt cgg aag ctc      3352
Leu Gly Ser Leu Arg Thr Ala Gln Thr Gln Leu Ser Arg Lys Leu
1085                1090                1095 ccg ggg acg acg ctg act gcc ctg gag gcc gca gcc aac ccg gca      3397
Pro Gly Thr Thr Leu Thr Ala Leu Glu Ala Ala Ala Asn Pro Ala
    1100                1105                1110 ctg ccc tca gac ttc aag acc atc ctg gac tga tggccacccg           3440
Leu Pro Ser Asp Phe Lys Thr Ile Leu Asp
    1115                1120 cccacagcca ggccgagagc agacaccagc agccctgtca cgccgggctc tacgtccag  3500
ggagggaggg gcggcccaca cccaggcccg caccgctggg agtctgaggc ctgagtgagt  3560
gtttggccga ggcctgcatg tccggctgaa ggctgagtgt ccggctgagg cctgagcgag  3620
tgtccagcca agggctgagt gtccagcaca cctgccgtct tcacttcccc acaggctggc  3680
gctcggctcc accccagggc cagcttttcc tcaccaggag cccggcttcc actccccaca  3740
taggaatagt ccatcccag attcgccatt gttcacccct cgccctgccc tcctttgcct   3800
tccaccccca ccatccaggt ggagaccctg agaaggaccc tgggagctct gggaatttgg  3860
agtgaccaaa ggtgtgccct gtacacaggc gaggaccctg cacctggatg ggggtccctg  3920
tgggtcaaat tgggggagg tgctgtggga gtaaaatact gaatatatga gttttcagt   3980
tttgaaaaaa a                                                     3991
```

<210> SEQ ID NO 41
<211> LENGTH: 1123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175
```

-continued

```
Gln Leu Gly Ala Ala Thr Gln Ala Arg Pro Pro His Ala Ser Gly
            180                 185                 190

Pro Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605
```

```
His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Val
    850                 855                 860

Thr Pro His Leu Thr His Ala Lys Thr Phe Leu Arg Thr Leu Val Arg
865                 870                 875                 880

Gly Val Pro Glu Tyr Gly Cys Val Val Asn Leu Arg Lys Thr Val Val
                885                 890                 895

Asn Phe Pro Val Glu Asp Glu Ala Leu Gly Gly Thr Ala Phe Val Gln
            900                 905                 910

Met Pro Ala His Gly Leu Phe Pro Trp Cys Gly Leu Leu Leu Asp Thr
        915                 920                 925

Arg Thr Leu Glu Val Gln Ser Asp Tyr Ser Ser Tyr Ala Arg Thr Ser
    930                 935                 940

Ile Arg Ala Ser Leu Thr Phe Asn Arg Gly Phe Lys Ala Gly Arg Asn
945                 950                 955                 960

Met Arg Arg Lys Leu Phe Gly Val Leu Arg Leu Lys Cys His Ser Leu
                965                 970                 975

Phe Leu Asp Leu Gln Val Asn Ser Leu Gln Thr Val Cys Thr Asn Ile
            980                 985                 990

Tyr Lys Ile Leu Leu Leu Gln Ala  Tyr Arg Phe His Ala  Cys Val Leu
        995                 1000                1005

Gln Leu  Pro Phe His Gln Gln  Val Trp Lys Asn Pro  Thr Phe Phe
        1010                1015                1020

Leu Arg  Val Ile Ser Asp Thr  Ala Ser Leu Cys Tyr  Ser Ile Leu
```

```
                       1025                1030                1035

Lys Ala Lys Asn Ala Gly Met Ser Leu Gly Ala Lys Gly Ala Ala
   1040                1045                1050

Gly Pro Leu Pro Ser Glu Ala Val Gln Trp Leu Cys His Gln Ala
   1055                1060                1065

Phe Leu Leu Lys Leu Thr Arg His Arg Val Thr Tyr Val Pro Leu
   1070                1075                1080

Leu Gly Ser Leu Arg Thr Ala Gln Thr Gln Leu Ser Arg Lys Leu
   1085                1090                1095

Pro Gly Thr Thr Leu Thr Ala Leu Glu Ala Ala Ala Asn Pro Ala
   1100                1105                1110

Leu Pro Ser Asp Phe Lys Thr Ile Leu Asp
   1115                1120

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Pro Ala Leu Leu Thr Ser Arg Leu
1               5
```

POLYNUCLEOTIDES ENCODING MHC CLASS I-RESTRICTED HTERT EPITOPES, ANALOGUES THEREOF OR POLYEPITOPES

CROSS REFERENCE TO RELATED APPLICATIONS

This application is a Continuation-in-Part of U.S. application Ser. No. 11/795,027, filed Jul. 11, 2007, which is a national phase entry of PCT/EP2006/007571, filed Jul. 31, 2006, which claimed priority of European Patent Application No. 05291627.7, filed Jul. 29, 2005.

This invention relates to the field of anticancer therapy, and to the identification of immunogenic peptides derived from the human telomerase reverse transcriptase (hTERT). The present invention relates to polynucleotides encoding hTERT epitopes restricted to MHC class I molecule, analogues thereof and polyepitopes containing such epitopes and/or analogues. Are also included in the present invention, vectors and cells comprising such polynucleotides. The present invention also concerns compositions comprising hTERT polypeptides, corresponding polynucleotides, vectors and cells, for use in the treatment and/or prevention of cancer.

In light of deficits in current anticancer therapeutic approaches, antitumor therapy has enjoyed renewed interest. Recent studies have enhanced our understanding of anti melanoma immune responses associated with tumor regression. Collectively these data suggest that activated tumor-specific CD8 CTL are immunological weapon of choice for potent anti-tumor therapy. The research of over-expressed proteins permitting to trigger cytotoxic T lymphocytes to tumours of different origins is also progressing.

Telomerase is a ribonucleoprotein complex, consisting of a protein component, TERT, and an RNA component (TR) containing the template for the synthesis of the repeat unit $(T_2AG_3)$ added onto the ends of chromosomes, that stabilizes the chromosomes during replication and prevent end-to-end fusion. Maintenance of a constant telomere length prevents cells from aging, and confers immortality (Hahn et al. Nat Med 1999; 5:1164-70). High hTERT activity was found in more than 85% of human cancers, whereas most normal adult human tissues show no or little telomerase activity (Counter et al. Blood 1995; 85:2315-20).

The widespread expression of telomerase in tumors indicates that peptide fragments of hTERT could serve as tumor specific antigen(s) and this has been confirmed in several reports (Vonderheide et al. Immunity 1999; 10:673-9). Recent data from Phase I clinical trials demonstrate the feasibility of vaccine against hTERT in HLA-A2+ patients, opening the way for use of hTERT for therapeutic vaccination (Vonderheide et al. Clin Cancer Res 2004; 10:828-39; Parkhurst et al. Clin Cancer Res 2004; 10:4688-98). Nevertheless, the immunogenic hTERT peptides identified to date are restricted to one MHC allele HLA-A2.1, with only two initial reports on two HLA-supertypes, HLA-A3 and HLA-A24, represented respectively in 44.2% and 40% of the population.

Hence, the following publications reported the identification of hTRET peptides:
hTERT peptide ILAKFLHWL (SEQ ID NO: 1), restricted to HLA-A2 (Vonderheide et al. Immunity 1999; 10:673-9),
hTERT peptides MPRAPRCRA (SEQ ID NO: 2), RPAEEATSL (SEQ ID NO: 6), RPSFLLSSL (SEQ ID NO: 10) and APRCRAVRS (SEQ ID NO: 2) identified by informatic prediction within the HLA-A context (WO 00/02581). However, these peptides have never been confirmed by experimental results to be efficient epitopes, neither in a HLA-B7 context nor in any HLA context.
hTERT peptide KLFGVLRLK (SEQ ID NO: 3) (K973), restricted to HLA-A3 (Vonderheide et al. Clin Cancer Res 2001; 7:3343-8), and
hTERT peptides VYAETKHFL (SEQ ID NO: 4) (TEL324) and VYGFVRACL (SEQ ID NO: 5) (TEL 461), restricted to HLA-A24 (Arai et al. Blood 2001; 9:2903-7)

Consequently, the hTERT peptides identified so far do not cover all the population, thus excluding a large segment of patients.

In order to overcome this failure, at least in part and to thus better cover the genetic diversity of the human population, the present invention identifies new epitopes derived from hTERT, restricted to a particular HLA which is different from HLA-A3 and HLA-A24. Among the many different alleles, the present application is interested in the HLA-B7 supertype which is expressed in about 25% of the population, and particularly to the second allele the most expressed in the human HLA-B population: the HLA-*B0702 (allele present in 15-20% of individuals in human population).

The gene of the isoform-1 of the telomerase is 4015 base pairs (bp) long (NCBI Accession number AF015950) and encodes a protein of 1132 amino acids (NCBI Accession number AAC51672.1) (FIG. 1).

The invention concerns a polynucleotide encoding a human telomerase reverse transcriptase (hTERT) peptide. In a particular embodiment of the invention, the encoded peptides are 9 amino acids in length (nonamer) or 10 amino acids in length (decamer), and the polynucleotide has hence 27 or 30 nucleotides. In general, the encoded peptide is less than 15 amino acids and the polynucleotide has less than 45 nucleotides.

The invention also concerns a polynucleotide encoding hTERT peptides that are epitopes, restricted to MHC class I molecule, especially epitopes suitable to induce an immune response restricted to HLA-B7. The nucleotide sequence of the polynucleotide of the invention is, in a particular embodiment, limited to the sequence encoding the hTERT peptide. Such peptides can be chosen from the group consisting of MPRAPRCRA (SEQ ID NO: 6) (p1; amino acid residues 1 to 9), APRCRAVRSL (SEQ ID NO: 7) (p4; amino acid residues 4 to 13), APSFRQVSCL (SEQ ID NO: 8) (p68; amino acid residues 68 to 77), RPAEEATSL (SEQ ID NO: 9) (p277; amino acid residues 277 to 285), RPSFLLSSL (SEQ ID NO: 10) (p342; amino acid residues 342 to 350), RPSLTGARRL (SEQ ID NO: 11) (p351; amino acid residues 351 to 360), DPRRLVQLL (SEQ ID NO: 12) (p444, amino acid residues 444 to 452), FVRACLRRLSEQ ID NO: 13) (p464, amino acid residues 464 to 472), AGRNMRRKL (SEQ ID NO: 14) (p966, amino acid residues 966 to 974), LPGTTLTAL (SEQ ID NO: 15) (p1107, amino acid residues 1107 to 1115) and LPSPKFTIL (SEQ ID NO: 16) (p1123, amino acid residues 1123 to 1131). All these polynucleotides may be used to induce a HLA-B7-restricted immune response. In a particular embodiment, the invention especially concerns a polynucleotide encoding a HLA-B7-restricted hTERT epitope, chosen from the group consisting of RPSLTGARRL (SEQ ID NO: 11) (p351), APSFRQVSCL (SEQ ID NO: 8) (p68), APRCRAVRSL (SEQ ID NO: 7) (p4), DPRRLVQLL (SEQ ID NO: 12) (p444), FVRACLRRL (SEQ ID NO: 13) (p464), AGRNMRRKL (SEQ ID NO: 14) (p966), LPGTTLTAL (SEQ ID NO: 15) (p1107) and h LPSPKFTIL (SEQ ID NO: 16) (p1123).

As defined herein, an "epitope" is an antigenic determinant, i.e. the peptide site recognized by cells of the immune system (immune cells) and especially the site necessary to elicit an immune response. The term epitope encompasses both linear epitope for which the consecutive amino acids (especially, 9 or 10) are recognized by immune cells and, conformational epitope for which immune cells recognize amino acids to the extent they adopt a proper configuration or conformation. Consequently, in some epitopes, the conformation (three dimensional structure) is as important as the amino acid sequence (primary structure).

The expression "MHC class I-restricted" refers to the capacity for a particular peptide or epitope to have an affinity for a MHC (major histocompatibility complex) molecule of class I. Similarly, the expression "HLA-B7-restricted" refers to the capacity for a particular peptide or epitope to have an affinity for this type of HLA molecule.

Briefly, MHC genes encode cell surface polymorphic molecules that do not bind only foreign peptides but also can bind overexpressed or not self peptides or mutated self peptides, to display them on the cell surface of cell enabling their recognition by appropriate immune cells, especially T-cells. Said MHC molecules, referred to as H-2 in mice and HLA (Human Leucocyte Antigen) in humans, are classified as either class I molecules (designated HLA-A, B, or C) or class II molecules (designated DP, DQ or DR).

Accordingly, MHC class I molecules specifically bind CD8 molecules expressed on cytotoxic T lymphocytes (also named TCD8$^+$), whereas MHC class II molecules specifically bind CD4 molecules expressed on helper T lymphocytes (TCD4$^+$).

MHC class I molecules bind peptides derived from proteolytically degraded proteins especially endogenously synthesized proteins, by a cell. Small peptides obtained accordingly are transported into the endoplasmic reticulum where they associate with nascent MHC class I molecules before being routed through the Golgi apparatus and displayed on the cell surface for recognition by cytotoxic T lymphocytes.

In the present invention, the above-identified peptides have been shown on the one hand to bind either with high or medium affinity to MHC class I molecule, and on the other hand to be efficiently transported as a MHC/epitope complex to the cell surface of cells. In a preferred embodiment, the MHC class I molecule is an MHC allele of the HLA-B7 supertype family; the hTERT epitope is said HLA-B7 supertype-restricted. Said family encompasses alleles B0702, B0703, B0704, B0705, B1508, B3501, B3502, B3503, B51, B5301, B5401, B5501, B5502, B 5601, B5602, B6701 and B7801, family from which the HLA-B0702 is preferred (HLA-B0702-restricted hTERT epitope).

A MHC stabilization assay may be used to test the affinity of a peptide for a particular HLA class I molecule (relative avidity), such as the one described in Firat et al. (1999. Eur. J. of Immunol. 29: 3112-3121), incorporated herein by reference. Briefly, MHC class I molecule-transfected cells are incubated overnight at 2×10$^5$ cells/well in 96-well plates in serum free medium AIM-V (Invitrogen Corp., Gibco), supplemented with 100 ng/ml of human β2-microglobulin,
in the absence of peptides (negative control),
in the presence of a reference peptide (positive control), and
in the presence of the peptides to be tested (hTERT peptides in the present case).
Peptides are incubated at various final concentrations ranging from 0.1 to 100 μM (with intermediate concentrations of 1 and 10 μM). The transfected cells are then labelled with a saturating concentration of an antibody recognizing the particular HLA MHC class I molecule, then washed twice and finally stained with a secondary antibody before flow cytometry. Results are expressed as values of relative avidity, that is the ratio of concentration of tested peptide necessary to reach 20% of the maximal binding by the reference to that of the reference peptide. Therefore, the lower the value, the stronger the binding. Following this method, a peptide is said to have a high relative affinity for a particular HLA class I molecule, when RA<1. In contrast, a medium relative affinity is concluded when RA is comprised between 1 and 5, and preferably between 1 and 3.

Among the hTERT nonamers and decamers, and particularly the above-identified peptides, the following MHC class I-restricted hTERT epitopes can be classified as having high relative affinity for MHC class I molecule: MPRAPRCRA (SEQ ID NO: 6) (p1), APRCRAVRSL (SEQ ID NO: 7) (p4) and APSFRQVSCL (SEQ ID NO: 8) (p68). Using the same approach, the following MHC class I-restricted hTERT epitopes can be classified as having a medium relative affinity for MHC class I molecule: RPAEEATSL (SEQ ID NO: 9) (p277), RPSFLLSSL (SEQ ID NO: 10) (p342), DPRRLVQLL (SEQ ID NO: 12) (p444) and RPSLTGARRL (SEQ ID NO: 11) (p351).

The present invention also relates to a polynucleotide encoding a MHC class I-restricted epitope analogue, i.e., epitopes having at least one amino acid substitution compared to a class I-restricted hTERT epitope as described above, especially HLA-B7-restricted epitope analogue.

The term "analogue" as defined herein relates to a peptide whose sequence is derived from a hTERT peptide as described above by at least one amino acid substitution, either conservative, semi-conservative or non-conservative. An analogue is opposed to an epitope by the fact that its nucleotide and/or amino acid sequence is not found in the reference hTERT gene or protein disclosed in FIG. 1 which are considered within the present application as the molecules of reference to define the so-called wild type peptides or polynucleotides. Such an analogue may result from the substitution in the corresponding nucleotide sequence of one or several nucleic base(s) in the codon encoding said amino acid. Therefore, a polynucleotide analogue differs from its wild type counterpart (polynucleotide encoding hTERT peptide with the reference sequence from which the peptide analogue is derived from) by at least one substitution, and preferably one, two or three substitutions in the codon(s) encoding the amino acid residue to be substituted. As an example, the APRRLVQLL (SEQ ID NO: 17) peptide (called p444*) is derived from the p444 peptide by the substitution of the first amino acid residue (D->A).

A particular analogue of a HLA-B7-restricted analogue has the same length or is shorter than the epitope from which it derives.

As a particular embodiment, the hTERT epitopes described above or the analogues always conserve in their primary structure a proline (P) in position 2, and/or one of the following amino acids in the last C-terminal position: A, L, I, M, V, F, W or Y. Therefore, the hTERT peptides, including the analogues, have the following consensus sequence: X-P-X$_{6-7}$-[ALIMVFWY], wherein X refer to any amino acid, X$_{6-7}$ refers to the number of amino acids and [ALIMVFWY] refers to one of these amino acids.

Therefore, to provide an epitope analogue, the amino acid substitution or the corresponding codon substitution in the polynucleotide is not located in the second position (or second codon). In a preferred embodiment, no substitution is carried out in the C-terminal position, even though the last C-terminal amino acid can be replaced by an equivalent amino acid, i.e. either A, L, I, M, V, F, W or Y. Finally, in a preferred embodiment, the substitution is located in the first amino acid position, wherein any amino acid is replaced by an alanine (A).

In a further embodiment of the invention, the last C-terminal amino acid of a decamer is deleted to give a nonamer, provided that the resulting nonamer maintains or adopts the X-P-X$_{6-7}$-[ALIMVFWY] consensus sequence. In the same way, an amino acid selecting among A, L, I, M, V, F, W and Y is added at the C-terminal end of a nonamer to give rise to decamer, provided that the resulting decamer maintains or adopts the X-P-X$_{6-7}$-[ALIMVFWY] consensus sequence.

In case of substitution, deletion or addition, including especially those illustrated above, taken individually or as combinations, the tridimensional conformation of the peptide analogue must be the same or slightly modified with respect to the one of the wild type counterpart, to ensure a correct folding of the analogue and its correct binding to the MHC class I molecule. The MHC stabilization assay described above can be used to check that such constraints are fulfilled.

The resulting analogue has at least the same characteristics as its wild type counterpart, in terms of affinity for a particular MHC class I molecule, especially HLA-B7 molecule, and has essentially the same capacity to be transported as an epitope/MHC complex on the cell surface and/or has essentially the same capacity to elicit an immunogenic response when tested in the same conditions.

In a preferred embodiment, the starting peptide is a hTERT epitope having a medium affinity, and the resulting analogue has a higher affinity than its wild type counterpart. In another embodiment, the analogue has a higher immunogenicity than its wild type counterpart. As an example, the p444* peptide analogue quoted above has an increased affinity for MHC class I molecule compared to the p444 peptide from which it is derived from. Accordingly, in a particular embodiment the aspects and features of the invention described herein apply to the p444* peptide analogue or its polynucleotide counterpart, including as combined features.

This is an object of the invention to provide hTERT epitope or analogue, able to elicit an immune response, and particularly a CTL response (Cytotoxic T Lymphocyte). However, the T lymphocytes do not recognize said analogue that is used to stimulate said lymphocytes only, via antigen presenting cells. In an embodiment of the invention, the analogue as described above keeps its immunogenic behaviour, and is able to elicit an immune response against cells overexpressing hTERT epitopes, i.e. that CTLs recognize the wild type epitope, even if stimulated with an epitope analogue. In a particular embodiment, the lymphocytes stimulated by an epitope analogue of the invention do not react against cells, which do not overexpressed hTERT epitopes. Therefore, stimulated lymphocytes do not react with cells overexpressing other epitopes (cross reaction) or with cells expressing hTERT epitope as basal level (healthy cells). In a particular embodiment, all the characteristics mentioned above are in a HLA-B7 environment, and preferably in a HLA-B0702 context.

A conventional cytotoxicity assay may be performed by using a standard 4-5 h $^{51}$Cr release assay to test the capacity of stimulated lymphocytes to react against target cells, such as in the Firat publication (1999. Eur. J. of Immunol. 29: 3112-3121) incorporated herein by reference. Briefly, cell suspension containing CTLs, are activated with peptide (hTERT peptide or analogue in the present case) plus self MHC Class I molecule in vivo. Target cells (expressing or not the corresponding HTERT epitope) previously incubated with $^{51}$Cr, are then incubated with activated lymphocytes. The recognition of target cells by activated CTL leads to the apoptosis of target cells and the release of $^{51}$Cr, wherein said release is proportional to the number of target cells killed. An incubation of target cells with a control peptide is used as a negative control to calculate the spontaneous release of $^{51}$Cr. Specific percentage of lysis is calculated by subtracting non-specific lysis observed with the control peptide to lysis obtained with the peptides to be tested. The higher the percentage, the more targets have been killed by the CTL. Specific lysis is determined at several ratios of Effector (CTL) to target cells (E:T). The specific lysis is calculated as the ratio between [experimental release−spontaneous release] and [total release−spontaneous release].

The present invention also concerns a polynucleotide encoding a polyepitope. A polyepitope is defined as a polypeptide having at least two epitopes, chosen among the MHC class I-restricted, especially HLA-B7-restricted hTERT epitopes (p1, p4, p68, p277, p342, p351, p444, p464, p966, p1107 and p1123) and/or MHC class I-restricted, especially HLA-B7-restricted, epitope analogues of the invention. The polynucleotide of the invention comprises or consists of at least two polynucleotide units encoding said epitopes or analogues. A polynucleotide unit is defined as the coding sequence for an epitope or analogue of the invention as disclosed herein.

The invention particularly concerns a polynucleotide encoding a polyepitope, comprising at least two epitopes chosen among (a) RPSLTGARRL (SEQ ID NO: 11) (p351), (b) APSFRQVSCL (SEQ ID NO: 8) (p68), (c) APRCRAVRSL (SEQ ID NO: 7) (p4), (d) DPRRLVQLL (SEQ ID NO: 12) (p444), (e) FVRACLRRL (SEQ ID NO: 13) (p464), (f) AGRNMRRKL (SEQ ID NO: 14) (p966), (g) LPGTTLTAL (SEQ ID NO: 15) (p1107) and (h) LPSPKFTIL (SEQ ID NO: 16) (p1123), or their analogues as defined above. Another polynucleotide, encoding a polyepitope, comprises at least one polynucleotidic unit chosen in the group of either a polynucleotide encoding a HLA-B7-restricted hTERT epitope corresponding to (a) RPSLTGARRL (SEQ ID NO: 11) (p351), (b) APSFRQVSCL (SEQ ID NO: 8) (p68), (c) APRCRAVRSL (SEQ ID NO: 7) (p4), (d) DPRRLVQLL (SEQ ID NO: 12) (p444), (e) FVRACLRRL (SEQ ID NO: 13) (p464), (f) AGRNMRRKL (SEQ ID NO: 14) (p966), (g) LPGTTLTAL (SEQ ID NO: 15) (p1107) and (h) LPSPKFTIL (SEQ ID NO: 16) (p1123) and/or their analogues as defined above, and at least one polynucleotidic unit chosen in the group of the polynucleotides encoding the sequence MPRAPRCRA (SEQ ID NO: 6) (p1), RPAEEATSL (SEQ ID NO: 9) (p277) or RPSFLLSSL (SEQ ID NO: 10) (p342), or their analogues as defined above.

None of the polyepitope-encoding polynucleotides of the invention coincides with the coding sequence of the full length hTERT.

In a particular embodiment of the invention, the number of MHC class I restricted hTERT epitopes and/or analogues in the prepared polyepitope is limited to 30. In another embodiment, the number of HLA-B7 restricted hTERT epitopes and/or analogues is limited to approximately 30, and is preferably 2, 3, 4, 5, 6, 7, 8, 9, 10, 15, 20, 25 or 30. In another embodiment, the number of HLA-B0702 restricted hTERT epitopes and/or analogues is limited to approximately 10, and is preferably 2, 3, 4, 5, 6, 7, 8, 9 or 10.

Accordingly, the polynucleotide encoding a polyepitope has 30 or less polynucleotide units, especially 2, 3, 4, 5, 6, 7, 8, 9, 10, 15, 20, 25 or 30 or any number within this range.

In a particular embodiment the polynucleotide units (and accordingly the epitopes) of the polynucleotide are consecutive.

In such a particular embodiment of the invention, the size of the nucleic sequence encoding the consecutive hTERT epitopes or analogues is less than 3000 bp, and preferably less than 2000 bp, 1000 bp, 500 bp, 400 bp, 300 bp, 200 bp or 100 bp.

In a particular embodiment, the polynucleotide encoding the multiple epitopes (polyepitope) consists of a nucleic acid molecule encoding a truncated or mutated form of the hTERT protein. In a preferred embodiment, the truncated or mutated form of the hTERT protein is deprived of its catalytic activity, i.e., is not capable to direct the synthesis of the repeat unit ($T_2AG_3$) at the ends of chromosomes, participating in the maintenance of telomere length. Such a hTERT protein deprived of its catalytic activity i.e., the retrotranscriptase activity, is said non-functional. Therefore, in another particular embodiment, the nucleic acid molecule encoding a truncated or mutated form of the hTERT protein lacks the catalytic activity domain of hTERT. In a particular embodiment, the nucleic acid molecule encoding a truncated form of the hTERT protein encodes a protein consisting of at least the 500 last C-terminal amino acids.

In a particular embodiment, the polynucleotide encodes a hTERT protein that is deleted for amino acids 867 to 869 (VDD sequence), corresponding to nucleotides 2654 to 2662 of FIG. 1 (wild-type) and providing nucleotide 2657 to be contiguous to nucleotide 2658 in FIG. 9 representing the deletion site, or alternatively for amino acids 864 to 872, corresponding to nucleotides 2645 to 2671 of FIG. 1 (wild-type) and providing nucleotide 2648 to be contiguous to nucleotide 2649 in FIG. 10 representing the deletion site. In a particular embodiment, the encoded hTERT protein has a deletion that comprises at least the amino acid residues 867 to 869 i.e., that the deletion is larger than the 3 amino acid residues (VDD sequence). As an example are the 864-872 deletion described above as well as a 22 amino acid deletion starting from amino acid residue 857 to 879 (according to FIG. 1) or a deletion comprising the amino acids N-terminal and the 5 amino acids C-terminal to the VDD sequence (from amino acid 862 to amino acid 874 according to FIG. 1, corresponding to nucleotides 2639 to 2679). In a particular embodiment, the invention concerns a polynucleotide comprising or consisting of the nucleotide sequence as set forth in FIG. 9 or FIG. 10.

The polynucleotide units encoding the multiple epitopes of the invention can be arranged consecutively, i.e., the 3' end of the first polynucleotide unit is directly linked to the 5' end of the second polynucleotide unit (and so on), resulting in a polynucleotide encoding a peptidic sequence exclusively composed of consecutive epitopes. Such a polynucleotide can encode a polyepitope comprising or consisting of the p1, p4, p68, p277, p342, p351, p444, p464, p966, p1107 and p1123 peptides. In a particular embodiment, the polynucleotide encodes the following peptidic sequence MPRAPR-CRAAPRCRAVRSLAPSFRQVSCLRPAEEAT SLRPS-FLLSSLRPSLTGARRL (SEQ ID NO: 20), comprising thus 6 MHC class I-restricted, particularly HLA-B7 restricted, hTERT epitopes.

The multiple epitopes of the invention can alternatively be separated by a one-amino acid spacer or a peptide spacer, i.e., meaning that the different polynucleotide units are separated by one or several codon(s) encoding respectively one or several amino acid(s). As spacers improving the processing of multiple epitopes, 4 amino acid-peptides composed of an arginine (R) in the C terminal position and hydrophilic residues (A, K, D and/or T) in other positions are preferred. Especially, 4 amino acid-peptides having a positively charged residue or an acidic residue in the C terminal position may be used, dependently or independently of hydrophilic residues (A, K, D and/or T) in other positions. In a particular embodiment, said spacers are internal processing sequences such as endosomal or lysosomal processing sequences, enabling the better processing of the multiple epitopes and avoiding the processing of new peptides resulting from overlapping cutting. Such a separation having recourse to a spacer can be used to separate all or, to the contrary, part of the polynucleotide units and accordingly, all or part of the epitopes.

The order in which the epitopes are arranged can be determined by the man skilled in the art, according to the following criteria: some orders may facilitate either the transcription and/or the translation of the polynucleotide, may facilitate the transport of the resulting expressed polyepitope in the endoplasmic reticulum (ER), especially if the tridimensional conformation impacts the properties, and may facilitate the processing of the polyepitope in several epitopes or analogues and avoid the processing of overlapping epitopes.

The polyepitope of the invention enables the elicitation of a CTL response against at least one, especially against several epitopes or analogues contained in the polyepitope, simultaneously, in a single animal or human.

In a particular embodiment, the polynucleotide encoding the polyepitope of the invention further comprises a polynucleotide encoding a target signal, operably linked to the polynucleotidic unit encoding the most N-terminal epitope of the at least two epitopes. "Operably linked" as used herein means that the target signal (upstream sequence) is linked to the N-terminal epitope (downstream sequence) in a way enabling the targeted signal to be operational, i.e., enabling to target the polyepitope to the correct cellular compartment or domain. Therefore, the link between the two sequences allows each sequence to play its own function in different locations and/or different stages. In a particular embodiment, said target signal is an endoplasmic reticulum signal sequence, and allows the polyepitope to be directed to the ER, for proper processing and association with the MHC class I molecule.

In a further embodiment, a codon encoding a methionine residue is added upstream of the sequence encoding the most N-terminal epitope, to enable the correct translation of the polynucleotide, if the translational process requires an initiation codon. Such a codon is added, only when the most N-terminal epitope does not possess a methionine residue in its first position.

The present invention also relates to a polynucleotide, according to the definitions given above, comprising or consisting of at least two polynucleotide units selected from the group consisting of a. ATGCCGCGCGCTCCCCGCTGCCGAGCC (SEQ ID NO: 21) (n1), b. GCTCCCCGCTGCCGAGCCGTGCGCTCCCTG (SEQ ID NO: 22) (n4), c. GCCCCCTCCTTCCGCCAGGTGTCCTGCCTG (SEQ ID NO: 23) (n68), d. AGACCCGCCGAAGAAGCCACCTCTTTG (SEQ ID NO: 24) (n277), e. CGGCCCTCCTTCCTACTCAGCTCTCTG (SEQ ID NO: 25) (n342), f. AGGCCCAGCCTGACTGGCGCTCGGAGGCTC (SEQ ID NO: 26) (n351), g. GACCCCCGTCGCCTGGTGCAGCTGCTC (SEQ ID NO: 27) (n444), h. TTCGTGCGGGCCTGCCTGCGCCGGCTG (SEQ ID NO: 28) (n464), i. GCTGGGAGGAACATGCGTCGCAAACTC (SEQ ID NO: 29) (n966), j. CTCCCGGGGACGACGCTGACTGCCCTG (SEQ ID NO: 30) (n1107), k. CTGCCCTCAGACTTCAAGACCATCCTG (SEQ ID NO: 31) (n1123), and l. GCCCCCCGTCGCCTGGTGCAGCTGCTC (SEQ ID NO: 32) (n444*).

The following polynucleotides make also part of the invention:

a polynucleotide, comprising at least one polynucleotidic unit selected from:
 a. AGGCCCAGCCTGACTGGCGCTCGGAGGCTC (SEQ ID NO: 26) (n351)
 b. GCCCCCTCCTTCCGCCAGGTGTCCTGCCTG (SEQ ID NO: 23) (n68),
 c. GCTCCCCGCTGCCGAGCCGTGCGCTCCCTG (SEQ ID NO: 22) (n4),
 d. GACCCCCGTCGCCTGGTGCAGCTGCTC (SEQ ID NO: 27) (n444),
 e. TTCGTGCGGGCCTGCCTGCGCCGGCTG (SEQ ID NO: 28) (n464),
 f. GCTGGGAGGAACATGCGTCGCAAACTC (SEQ ID NO: 29) (n966),
 g. CTCCCGGGGACGACGCTGACTGCCCTG (SEQ ID NO: 30) (n1107),
 h. CTGCCCTCAGACTTCAAGACCATCCTG (SEQ ID NO: 31) (n1123), and
 i. GCCCCCCGTCGCCTGGTGCAGCTGCTC (SEQ ID NO: 32) (n444*), or their analogues as defined above, and at least one polynucleotidic unit selected from:
 j. ATGCCGCGCGCTCCCCGCTGCCGAGCC (SEQ ID NO: 21) (n1),
 k. AGACCCGCCGAAGAAGCCACCTCTTTG (SEQ ID NO: 24) (n277),
 l. CGGCCCTCCTTCCTACTCAGCTCTCTG (SEQ ID NO: 25) (n342), or their analogues as defined above.

a polynucleotide, comprising at least one polynucleotidic unit selected from:
 a. AGGCCCAGCCTGACTGGCGCTCGGAGGCTC (SEQ ID NO: 26) (n351)
 b. GCCCCCTCCTTCCGCCAGGTGTCCTGCCTG (SEQ ID NO: 23) (n68),
 c. GCTCCCCGCTGCCGAGCCGTGCGCTCCCTG (SEQ ID NO: 22) (n4),
 d. GACCCCCGTCGCCTGGTGCAGCTGCTC (SEQ ID NO: 27) (n444),
 e. TTCGTGCGGGCCTGCCTGCGCCGGCTG (SEQ ID NO: 28) (n464),
 f. GCTGGGAGGAACATGCGTCGCAAACTC (SEQ ID NO: 29) (n966),
 g. CTCCCGGGGACGACGCTGACTGCCCTG (SEQ ID NO: 30) (n1107),
 h. CTGCCCTCAGACTTCAAGACCATCCTG (SEQ ID NO: 31) (n1123), and
 i. GCCCCCCGTCGCCTGGTGCAGCTGCTC (SEQ ID NO: 32) (n444*), or their analogues as defined above.

Are also included in the present invention, polynucleotides or polynucleotide units encoding an epitope, analogue or polyepitope of the invention, taking into consideration the degeneracy of the genetic code. Therefore, each amino acid can be encoded by the codon from the hTERT nucleotide reference sequence, or by any codon encoding said amino acid.

The invention also relates to a polynucleotide comprising or consisting of any combination of at least two of these polynucleotide units or analogues thereof, selected from the above group, wherein said polynucleotide unit or analogue encodes a MHC class I-restricted, especially a HLA-B7-restricted, hTERT epitope.

All features given above concerning epitopes, analogues, polyepitopes, combination thereof, spacers, target signal sequences . . . are applicable to any polypeptide of the invention as well as to the corresponding polynucleotide sequences.

A recombinant vector, comprising or consisting of a polynucleotide of the invention, as defined above, is also one object of the present invention. The recombinant vector can be a vector for eucaryotic or procaryotic expression, such as a plasmid, a phage for bacterium introduction, a YAC able to transform yeast, a viral vector and especially a retroviral vector, or any expression vector. An expression vector as defined herein is chosen to enable the production of an epitope or analogue or polyepitope as defined above, either in vitro or in vivo.

Therefore, besides the polynucleotide, the vector of the invention can further comprise transcription regulation regions (including promoter, enhancer, ribosome binding site (RBS), polyA signal), a termination signal, a prokaryotic or eukaryotic origin of replication and/or a selection gene. The features of the promoter can be easily determined by the man skilled in the art in view of the expression needed, i.e., constitutive, transitory or inducible, strong or weak, tissue-specific and/or developmental stage-specific promoter. Therefore, tissue-specific promoters can be chosen depending on the organ in which a composition containing this vector is administered, for example injected, and depending on the intensity of expression required. In a particular embodiment, the promoter is the CMV promoter (human cytomegalovirus). Said vector can also comprise sequence enabling conditional expression, such as sequences of the Cre/Lox system or analogue systems.

The expression vectors of the invention may be viral vectors, and particularly viral expression vector, such as retroviral-derived, especially lentiviral-derived vectors such as HIV-, FIV- or SIV-derived vectors. More particularly, the lentiviral-derived vector is a human lentiviral-derived vector such as an HIV expression vector, particularly HIV-1 or HIV-2-derived vector. A retroviral-derived vector comprises a retroviral vector genome, usually included in a DNA construct, such as a plasmid, and expressed in viral particles, wherein said retroviral vector genome comprises the elements necessary for the retrotranscription, particularly the LTRs possibly mutated including deleted in part, especially deleted in the U3 region. In no case, the retroviral-derived vector contains all the nucleotide sequences encoding the full-length retroviral proteins. Possibly, it contains part of one or several of said nucleotide sequences providing it does not encode said proteins or functional fragments thereof. Said DNA construct comprising said retroviral vector genome further comprises a DNA of interest recombined with the retroviral nucleotide sequences, said DNA of interest comprising or consisting of a polynucleotide of the invention.

In a preferred embodiment, the retroviral-derived vector genome comprises a DNA flap as described below and at least one polynucleotide of the invention. In a preferred embodiment, the retroviral-derived vector is a HIV expression vector comprising a DNA flap as described below and at least one polynucleotide of the invention. HIV vectors express therefore only the nucleic acid(s) of interest, including the polynucleotides of the invention, contained between the two HIV LTRs and can thus accommodate large sequences up to 5-6 kb. A particular embodiment of the invention is a HIV expression vector, and most particularly a HIV-1 or HIV-2 expression vector, wherein a HIV-1 LTR or respectively the HIV-2 LTR is deleted for the promoter and the enhancer of the U3 domain (ΔU3). This particular deletion has been previously shown to increase the expression of the nucleic acid(s) contained in the vector, and particularly when associated with a promoter. Another particular embodiment, the vector comprises a LTR deleted in the promoter and the enhancer of the U3 domain, a promoter such as a CMV or EF1α promoter and a polynucleotide of the invention.

In another embodiment, the polynucleotide of the invention introduced in the retroviral-derived vector is included in an expression cassette.

A DNA flap (or Triplex as disclosed in WO 99/55892, WO 01/27300 and WO 01/27304) is a nucleotide sequence of retroviral or retroviral-like origin comprising two essential regions, i.e., the cPPT (central polypurine tract) and the CTS (cis-acting termination region), regions, wherein the cPPT and CTS regions induce a three-stranded DNA structure. A DNA flap suitable for the invention may be obtained from a retrovirus or retrovirus-like organism such as retrotransposon, prepared synthetically (chemical synthesis) or by amplification of the DNA flap from any retrovirus nucleic acid such as Polymerase Chain Reaction (PCR). The retrovirus, from which the DNA flap may be obtained, is particularly a retrovirus or a lentivirus, especially a human retrovirus or lentivirus and is in particular a HIV retrovirus, the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. In a more preferred embodiment, the DNA flap is obtained from an HIV retrovirus, for example HIV-1 or HIV-2 virus or any different isolate of these two types. It is noteworthy that the DNA flap is used isolated from its natural (viral genome) nucleotide context i.e., isolated from the pol gene in which it is naturally contained in a retrovirus. Therefore, the DNA flap is used, in the present invention, deleted from the unnecessary 5' and 3' parts of the pol gene and is recombined with sequences of different origin.

The DNA flap acts as a cis-determinant of the vector nuclear import, and is of great interest for the recombination and the integration of nucleic acid(s) into both non-dividing and dividing cells. Expression retroviral-derived vector, especially HIV derived-vectors, including the DNA flap sequence (TRIP vectors) are able to transduce primary B and T cells, macrophages, dendritic cells, etc with a tenfold higher efficiency than other HIV vectors that lack the DNA flap. A transduction of 80-90% of cells can be routinely obtained.

In a preferred embodiment, a vector suitable for an in vivo expression and vaccine strategy is a retroviral and especially a lentiviral vector (see WO 99/55892, WO 01/27300 and WO 01/27304). Such vectors have been shown to be particularly efficient and secure, when their genome is modified (Firat et al. 2002, The Journal of Gene Medicine 4: 38-45). Indeed, these vectors have the ability to efficiently and stably transfer therapeutic or reporter genes, in a large variety of cells and tissues, such as hematopoietic stem cells, brain, liver and retina. Moreover, this high transduction efficiency is irrespective of the proliferative status of the target cells. In particular, these vectors have been shown to efficiently induce CD8+ T cell responses both in vivo in mice and ex vivo in humans, due to their capacity to transduce antigen presenting cells such as dendritic cell (DC) with high efficiency, ex vivo as well as in vivo (Esslinger et al. Hum Gene Ther 2002; 13:1091-100; Breckpot et al. J Gene Med 2003; 5:654-67; Esslinger et al. J Clin Invest 2003; 1111:1673-81).

The vector, defined in FIG. 7, has been used for in vitro or in vivo expression of epitopes, analogues or polyepitopes of the invention. As examples of vectors, from which the vectors of the invention can be derived, are the following, all deposited with the CNCM (Collection Nationale de Culture de Microorganismes at Institut Pasteur, Paris, France):

| Vector name | Accession number | Date of deposition | Described in patent application |
|---|---|---|---|
| pTRIP.EGFP | I-2005 | Apr. 15, 1998 | WO 99/55892 |
| PTRIP-MEL.IRES-GFP | I-2185 | Apr. 20, 1999 | |
| PTRIP-TEL/AML-IRES-GFP | I-2326 | Oct. 11, 1999 | WO 01/27300 |
| PTRIP-TEL/ILKE-IRES-GFP | I-2327 | Oct. 11, 1999 | |
| PTRIP-DES-IRES-GFP | I-2331 | Oct. 11, 1999 | |

The vectors described in the patent application WO 01/27304, and especially TRIP ΔU3 Efα1 GFP and TRIP ΔU3 PL CMV GFP, can also be used to derive the vectors of the present invention.

A particular vector of the invention is the pTRIP-CMV-ΔhTERT vector, deposited at the CNCM (Institut Pasteur, Paris, France) under the number CNCM I-3660 on Jul. 28, 2006. A suitable growth medium for cultivating this vector is a TB medium, optionally supplemented with hygromycin. Another expression vector of the invention is the pTRIP-CMV-ΔhTERT vector deposited at the CNCM under the number CNCM I-3660 on Jul. 28, 2006, in which the deleted hTERT sequence has been substituted by any polynucleotide of the invention.

The present invention also relates to cells comprising the polynucleotides or polynucleotide units of the invention.

In one embodiment, the cell is transfected with a vector of the invention, by methods well known to the man skilled in the art, i.e. by chemical transfection (calcium phosphate, lipofectamine), lipid-based techniques (liposome), electroporation, photoporation, use of viral vectors . . . . In another embodiment, a cell is transformed or transduced with a polynucleotide of the invention, in a way enabling integration of the polynucleotide in the cell genome either by a recombination with the homologous cellular sequence or by insertion in the cellular genome. The transfection, infection or transduction can occur ex vivo, i.e. in an artificial environment outside the living organism.

Among cells particularly interesting in the vaccine strategy are cells of the immune system, and especially antigen presenting cells (APC). In a particular embodiment, these cells are APCs involved either in MHC class I recognition, like dendritic cells (DC) or in MHC class II recognition such as macrophages or lymphocytes B. Among DCs, ex vivo fully maturated DCs, i.e., DCs that have been in vitro maturated by epitopes or analogues, are preferred.

As used herein, the terms "transfected", "transformed" or infected" refer to a cell comprising a vector of the invention (transient expression), whereas the term "genetically transformed" refers to a cell whose genome has been definitively modified by a polynucleotide of the invention (permanent expression).

Said transitory or stably transformed cells can be any prokaryotic (bacteria) or eukaryotic (yeast, animal including mammal especially human) cells. In an embodiment, cells are non-human cells. In a particular embodiment, cells of the invention are isolated human cells, "isolated" meaning outside of its natural environment.

The invention also relates to epitopes, analogues or polyepitope as defined above when describing the polynucleotides of the invention and particularly to any polypeptide encoded by a polynucleotide or polynucleotide units of the invention. Particular polypeptides are MHC class I-restricted, especially HLA-B7-restricted, hTERT epitope, chosen from the group consisting of:
 a. MPRAPRCRA (SEQ ID NO: 6) (p1),
 b. APRCRAVRSL (SEQ ID NO: 7) (p4),
 c. APSFRQVSCL (SEQ ID NO: 8) (p68),
 d. RPAEEATSL (SEQ ID NO: 9) (p277),
 e. RPSFLLSSL (SEQ ID NO: 10) (p342),
 f. RPSLTGARRL (SEQ ID NO: 11) (p351),
 g. DPRRLVQLL (SEQ ID NO: 12) (p444),
 h. FVRACLRRL (SEQ ID NO: 13) (p464),
 i. AGRNMRRKL (SEQ ID NO: 14) (p966),
 j. LPGTTLTAL (SEQ ID NO: 15) (p1107), and
 k. LPSPKFTIL (SEQ ID NO: 16) (p1123).

Particular HLA-B7-restricted hTERT epitopes, are chosen from the group consisting of:
 a. RPSLTGARRL (SEQ ID NO: 11) (p351),
 b. APSFRQVSCL (SEQ ID NO: 8) (p68),
 c. APRCRAVRSL (SEQ ID NO: 7) (p4),
 d. DPRRLVQLL (SEQ ID NO: 12) (p444),
 e. FVRACLRRL (SEQ ID NO: 13) (p464),
 f. AGRNMRRKL (SEQ ID NO: 14) (p966),
 g. LPGTTLTAL (SEQ ID NO: 15) (p1107),
 h. LPSPKFTIL (SEQ ID NO: 16) (p1123), and
 i. APRRLVQLL (SEQ ID NO: 17) (p444*).

A particular group consists of the following MHC class I-restricted, especially HLA-B7-restricted, hTERT epitopes:
 a. MPRAPRCRA (SEQ ID NO: 6) (p1),
 b. APRCRAVRSL (SEQ ID NO: 7) (p4),
 c. APSFRQVSCL (SEQ ID NO: 8) (p68), and
 d. RPSLTGARRL (SEQ ID NO: 11) (p351).

Another group consists of the following HLA-B7-restricted hTERT epitopes: RPAEEATSL (SEQ ID NO: 9) (p277) and RPSFLLSSL (SEQ ID NO: 10) (p342). A preferred HLA-B7 allele targeted by these epitopes is HLA-B0702.

The invention also concerns analogues of the peptides disclosed above, and having at least one amino acid substitution. Features pertaining to these analogues have especially been described in the above pages. A particular peptide analogue is p444* having the following peptide sequence APRRLVQLL (SEQ ID NO: 17).

Finally, the invention also concerns any polynucleotide encoding a hTERT epitope, analogue or polyepitope as described in the present specification.

The invention also relates to a polyepitope comprising at least two epitopes and/or analogues as described above. The polyepitopes of the invention are not the full-length hTERT protein. The size of said polyepitope can range from 15 to 1000 in particular from 50 or from 100 to 1000 amino acids, especially and particularly about 100, 200, 300, 400, 500 or 1000 amino acids. Such an epitope comprises or consists of 2 to 30 epitopes or analogues, and particularly 2 to 20 or 2 to 10 epitopes and/or analogues. A particular polyepitope comprises or consists of 6 consecutive epitopes and has the following sequence: MPRAPRCRAAPRCRAVRSLAPSFRQVSCLRPAEEATSLRPSFLLSSLRPSLTGARRL (SEQ ID NO: 20). Another particular polyepitope comprises or consists of the p1, p4, p68, p277, p342 and p351 epitopes, the epitopes being either consecutive to each other in the polyepitope obtained or all or part of them being separated by peptide spacers.

Another polyepitope of the invention comprises at least two epitopes, at least one being chosen from the group consisting of:
 a. RPSLTGARRL (SEQ ID NO: 11) (p351),
 b. APSFRQVSCL (SEQ ID NO: 8) (p68),
 c. APRCRAVRSL (SEQ ID NO: 7) (p4),
 d. DPRRLVQLL (SEQ ID NO: 12) (p444),
 e. FVRACLRRL (SEQ ID NO: 13) (p464),
 f. AGRNMRRKL (SEQ ID NO: 14) (p966),
 g. LPGTTLTAL (SEQ ID NO: 15) (p1107),
 h. LPSPKFTIL (SEQ ID NO: 16) (p1123), and
 i. APRRLVQLL (SEQ ID NO: 17) (p444*),
or analogues thereof obtained by substitution of at least one amino acid residue, and at least one being chosen from the group consisting of
 j. MPRAPRCRA (SEQ ID NO: 6) (p1),
 k. RPAEEATSL (SEQ ID NO: 9) (p277),
 l. RPSFLLSSL (SEQ ID NO: 10) (p342),
or analogues thereof obtained by substitution of at least one amino acid residue, wherein said polyepitope is not the full length hTERT.

Polypeptides of the invention can be synthesized chemically, or produced either in vitro (cell free system) or in vivo after expression of the corresponding nucleic acid sequence in a cell system.

The full-length hTERT protein (SEQ ID NO: 37) as represented in FIG. 1 is excluded from the invention, as well as the corresponding full-length coding sequence (SEQ ID NO: 36). Also excluded from the present invention, the RPALLTSRL (SEQ ID NO: 42) peptide. These peptides are excluded particularly in the context of HLA-B7 recognition.

The invention also concerns an epitope, analogue, polyepitope or polynucleotide, an expression vector or host cell as defined above, for use to elicit or participate in providing a HLA-B7-restricted immune response against hTERT.

The invention also concerns a composition comprising a polynucleotide, a vector, a host cell and/or a polypeptide of the invention. In a particular embodiment, said composition is suitable for in vivo administration, i.e., said composition is prepared for injection, or more generally for association with physiologically-acceptable liquid solutions or emulsions for administration. Said composition may be used either for systemic or local administration, especially by injection, and may further comprises a pharmaceutically suitable excipient (including water, saline, dextrose, glycerol, ethanol, and combinations thereof) or a carrier and/or a vehicle.

In a particular embodiment, said composition comprises a polynucleotide of the invention encoding an epitope, analogue or encoding a polyepitope as described above. Said composition can comprise other nucleic acid molecules encoding at least one hTERT epitope or analogue thereof or polyepitope, restricted to a different MHC class I allele from that of HLA-B7. The combination of hTERT epitopes restricted to different HLA supertypes or alleles enables covering a larger population of patients in need of treatment than a sole supertype or allele. To this end, HLA-A1, -A2, -A3 and -A24 are preferred.

In another embodiment, the composition comprises nucleic acid molecules encoding at least one hTERT epitope or analogue thereof or polyepitope, restricted to MHC class II. Said composition can comprise any combination of nucleic acid molecules as described above, with at least one HLA-B7-restricted hTERT epitope, analogue or polyepitope of the present invention. The combination, in a composition of nucleic acid molecules, of polynucleotides encoding Class I and Class II-restricted epitopes enabling the reaction of various immune cells (T lymphocytes or NK cells for class I versus helper lymphocytes for class II), and/or the elicitation of various immune responses (humoral versus cellular response) is also within the present invention.

In another embodiment, the composition comprises nucleic acid molecules comprising at least such molecules encoding one tumour-specific antigen (TSA) and/or at least one tumour-associated antigen (TAA), such as prostate specific antigen (PSA), prostate-specific membrane antigen (PSMA) or prostatic acid phosphatase (PAP) (Tartour et al. 2000 Immunol Lett September 15; 74(1): 1-3; Tartour et al. 1996 Presse Med. November 16; 25(25): 1717-22).

Several types of therapeutic compositions can be used to elicit an immune response against an epitope or analogue of the invention.

A composition comprising a polynucleotide of the invention is administered to a host, for instance injected (known as DNA vaccination) and said nucleic acid expresses in vivo a polypeptide comprising or consisting of multiple epitopes according to the invention. Such DNA vaccines usually consist of plasmid vectors as described above. The delivery of naked DNA has shown to be poorly efficient, and some carriers are needed to improve the delivery and uptake of DNA into cells. Two types of carriers have been yet developed: (1) viral carriers (adenoviruses, lentiviruses, measles virus), or (2) non-viral carriers such as polymers (and especially cationic polymers), encapsulated-DNA (liposomes, comprising cationic lipids interact spontaneously and rapidly with polyanions, such as DNA and RNA, resulting in liposome/nucleic acid complexes) or DNA linked to gold microparticles. Moreover, agents, which assist in the cellular uptake of nucleic acid, such as calcium ions, bacterial proteins (*Shigella* proteins) viral proteins and other transfection facilitating agents, may advantageously be used. Another type of composition according to the invention is a composition comprising lentiviral pseudoparticles comprising a vector or vector genome as mentioned above.

Another type of composition comprises an epitope, analogue or polyepitope of the invention. Such a composition is immunogenic, i.e., it is capable of eliciting an immune response in a host in which it is administered. However, to increase the immunogenic properties of the polypeptides of the invention, an adjuvant can be administered with the polypeptide, to elicit or improve the immune response. An adjuvant is defined as any substance that enhances the immunogenicity of an antigen mixed with said adjuvant. Some adjuvants convert soluble antigens into small particles, such as aluminium hydroxide gel, oil in water emulsion or immune stimulatory complexes (ISCOMs). Another class of adjuvants comprises sterile constituents of bacteria such as cell wall or polysaccharides, Freund adjuvant. Finally, emulsifying agents or pH buffering agents can also be used to enhance the immunogenic behaviour of the epitope or analogue.

All compositions quoted above can be injected in a host via different routes: subcutaneous (s.c.), intradermal (i.d.), intramuscular (i.m.) or intravenous (i.v.) injection, oral administration and mucosal administration, especially intranasal administration or inhalation. The quantity to be administered (dosage) depends on the subject to be treated, including the condition of the patient, the state of the individual's immune system, the route of administration and the size of the host. Suitable dosages range from 200 µg to 1 mg, and can be modified by one skilled in the art, depending on circumstances.

The compositions of the invention are useful for the prophylaxis and or treatment of malignant states in patients, resulting from uncontrolled cell proliferation, including tumors, resulting from the over-expression of hTERT, as well for the treatment of detrimental consequences accompanying such malignant state, e.g., cancer. The expression "treatment" encompasses the curative effect achieved with compositions of the invention and also the beneficial effect for the patient undergoing the treatment, said effect being either obtained at cellular level or clinical level, including as a result, an improvement of the condition of the patient and/or a remission state or a recovery of a health state. In a particular embodiment, the composition of the invention further comprises additional active compounds useful for the prophylaxis or the treatment of tumors, either general compounds or compounds proved to be active in a tissue-specific cancer.

The invention also concerns a process to activate T lymphocytes against class I-restricted, particularly HLA-B7-restricted, hTERT epitopes:
   a. providing T lymphocytes, and,
   b. in vitro cultivating said T lymphocytes with at least one epitope or epitope analogue or polyepitope of the invention, in conditions enabling the activation of said lymphocytes.

In a particular embodiment, activated T lymphocytes are cytotoxic T lymphocytes (CTL). Conventional conditions to activate T lymphocytes use interleukine (IL) 2, IL-7, IL-12 and/or IL-15, and are described in Minev et al. (2000 PNAS; 97(9): 4796-4801) incorporated herein by reference.

The invention also relates to a process to check the immunogenic behaviour of a hTERT peptide, comprising:
   a. activating T lymphocytes, by in vitro cultivating said T lymphocytes with at least one epitope or epitope analogue or polyepitope of the invention, in appropriate conditions,
   b. in vitro cultivating said activated lymphocytes with target cells expressing, at their cell surface, a hTERT epitope of the invention bound to a MHC-class I molecule, in suitable conditions, and
   c. determining whether said activated lymphocytes react against said target cells.

In a particular process to check the immunogenic behaviour of a hTERT peptide, the epitope when used individually i.e., not under the form of a polyepitope, is chosen among (a) RPSLTGARRL (SEQ ID NO: 11) (p351), (b) APSFRQVSCL (SEQ ID NO: 8) (p68), (c) APRCRAVRSL (SEQ ID NO: 7) (p4), (d) DPRRLVQLL (SEQ ID NO: 12) (p444), (e) FVRACLRRL (SEQ ID NO: 13) (p464), (f) AGRNMRRKL (SEQ ID NO: 14) (p966), (g) LPGTTLTAL SEQ ID NO: 15) (p1107) and (h) LPSPKFTIL (SEQ ID NO: 16) (p1123); an example of analogue is the p444* as defined above.

A process to check the immunogenic behaviour and HLA-B7-restriction of a hTERT peptide, comprising:
   a. activating T lymphocytes as described above, with an epitope chosen among MPRAPRCRA (SEQ ID NO: 6) (p1), APRCRAVRSL (SEQ ID NO: 7) (p4), APSFRQVSCL (SEQ ID NO: 8) (p68), RPAEEATSL (SEQ ID NO: 9) (p277), RPSFLLSSL (SEQ ID NO: 10) (p342) RPSLTGARRL (SEQ ID NO: 11) (p351), DPRRLVQLL (SEQ ID NO: 12) (p444), FVRACLRRL (SEQ ID NO: 13) (p464), AGRNMRRKL (SEQ ID NO: 14) (p966), LPGTTLTAL (SEQ ID NO: 15) (p1107) and LPSPKFTIL (SEQ ID NO: 16) (p1123) or epitope analogue such as APRRLVQLL (SEQ ID NO: 17) (p444*) or polyepitope as defined above;
   b. in vitro cultivating said activated lymphocytes with target cells expressing, at their cell surface, a hTERT epitope of the invention bound to a HLA-B7 molecule, in suitable conditions, and
   c. determining whether said activated lymphocytes react against said target cells.

The activation of lymphocytes includes the presentation of said epitopes or analogues by antigen presenting cells to naïve (not activated) T lymphocytes. Once naïve T lymphocytes have recognized the epitope or analogue of the invention, in the context of a particular class-I HLA molecule, they are said "activated" and ready to recognize said epitope on the cell surface of a target cell. The contact between said activated lymphocytes (effector cells) and target cells (expressing the epitope, from which the lymphocyte has been activated), leads to the secretion of molecules and killing of the target cells. If an epitope or analogue used to activate lymphocytes leads to an efficient destruction of a target cell bearing said epitope by said activated lymphocytes, said epitope can be considered as immunogenic enough to allow not only in vitro but also in vivo T cell reaction against cells expressing said epitopes. Suitable conditions for target cells/lymphocytes recognition are a 4 hour-contact at 37° C. in RPMI medium.

The invention also relates to a process to in vitro maturate cells, and especially antigen presenting cells (APC), B cells, T cells and/or dendritic cells, against MHC class I-restricted, particularly HLA-B7-restricted, hTERT epitopes. Such a process to in vitro maturate cells comprises:
 a. providing cells,
 b. enabling the maturation of said cells with at least one MHC class I-restricted, particularly HLA-B7-restricted, hTERT epitope or epitope analogue or polyepitope of the invention, and
 c. optionally, favouring the expansion of said maturated cells.

As described above, the activation of lymphocytes requires epitope presentation by maturated antigen presenting cells. In a preferred embodiment of the invention, said cells express at least one HLA-B7 allele. One of them, dendritic cells (DC), are particularly efficient in presentation of endogenous epitopes restricted to MHC class I, to T lymphocytes. One of the objectives in the maturation of said cells is their administration once maturated, to a patient in need of treatment. The administration of said maturated DCs would result in vivo in the activation of patient's lymphocytes, and rapid reaction against cell expressing the epitope (the one, the DCs have been transformed with).

In a particular embodiment, a process to in vitro maturate dendritic cells comprises:
 a. providing dendritic cells,
 b. enabling the maturation of said dendritic cells with at least one MHC class I-restricted hTERT epitope or epitope analogue or polyepitope of the invention, and
 c. optionally, favouring the expansion of said maturated dendritic cells.

In a particular embodiment, said dendritic cells are isolated from either circulating blood or bone marrow cells. In another embodiment, dendritic cells are isolated from the patient in need of treatment or from an HLA-matched donor, to avoid rejection after the administration to said patient.

The maturation of DCs can be achieved by genetic transformation of said dendritic cells with a polynucleotide of the invention, by transfection of said dendritic cells with a vector of the invention or by contacting said dendritic cells with at least one epitope, epitope analogue or polyepitope of the invention. The genetic transformation is preferred because of its efficiency and the permanent expression of the epitope, analogue or polyepitope encoded by the polynucleotide inserted in the DC genome.

The invention also concerns a polynucleotide encoding a HLA-B7-restricted hTERT epitope for use in the prevention and/or treatment of cancer. In a particular embodiment, said polynucleotide, for use in the prevention and/or treatment of cancer encodes a HLA-B7-restricted hTERT epitope or analogue thereof or a polyepitope comprising at least one HLA-B7-restricted hTERT epitope or analogue thereof as described in the present application. As far as the polyepitope-encoding polynucleotide is concerned, it does not coincide with the coding sequence of the full-length hTERT. On the other hand, it can coincide with a mutated or deleted version of HTERT, said mutation or deletion suppressing the catalytic activity of the human telomerase. In a particular embodiment, said polynucleotide comprises at least one polynucleotide unit encoding a HLA-B7-restricted hTERT epitope, chosen from the group consisting of:
 a. MPRAPRCRA (SEQ ID NO: 6) (p1),
 b. APRCRAVRSL (SEQ ID NO: 7) (p4),
 c. APSFRQVSCL (SEQ ID NO: 8) (p68),
 d. RPAEEATSL (SEQ ID NO: 9) (p277),
 e. RPSFLLSSL (SEQ ID NO: 10) (p342),
 f. RPSLTGARRL (SEQ ID NO: 11) (p351)
 g. DPRRLVQLL (SEQ ID NO: 12) (p444),
 h. FVRACLRRL (SEQ ID NO: 13) (p464),
 i. AGRNMRRKL (SEQ ID NO: 14) (p966),
 j. LPGTTLTAL (SEQ ID NO: 15) (p1107), and
 k. LPSPKFTIL (SEQ ID NO: 16) (p1123),
or at least one analogue of said HLA-B7-restricted hTERT, such as APRRLVQLL (SEQ ID NO: 17) (p444*), or any combination forming a polynucleotide having at least two polynucleotide units encoding said HLA-B7 epitopes and/or analogues.

The invention concerns a HLA-B7 hTERT epitope, and especially a HLA-B0702 restricted epitope for use in the prevention and/or treatment of cancer. The invention relates also to a polynucleotide, a vector, a host cell or a polypeptide of the invention for use in the prevention and/or treatment of cancer.

The invention also relates to the use of a HLA-B7 hTERT epitope, (or corresponding polynucleotide) for the manufacture of a drug for the prevention and/or treatment of cancer. Particular HLA-B7 hTERT epitopes (or corresponding polynucleotides) are those described above as well as vectors, cells or compositions comprising or consisting of them. In a particular embodiment, the use of polynucleotide, vector, host cell or polypeptide comprising or consisting of a polyepitope of the invention in the manufacture of a drug for the prevention and/or treatment of cancer is intended for patients having at least one HLA-B7 allele as defined above, and particularly at least one HLA-B0702 allele.

Each definition provided in the specification applies to each and any peptide (epitope, analogue or polyepitope) as well as to each and any polynucleotide, taken individually (as such) or encompassed in a group.

BRIEF DESCRIPTION OF THE DRAWINGS

FIG. 1: Gene encoding the hTERT protein (SEQ ID NO: 36) and corresponding amino acid sequence (SEQ ID NO: 37).

The coding sequence is located between the nucleotide 56 and 3454. Initiation and termination codons are underlined. First line is the nucleotide sequence; second line is the corresponding amino acid sequence. Third line is the numerotation of the hTERT coding sequence, starting from the initiation codon as the first amino acid.

Figure 2:
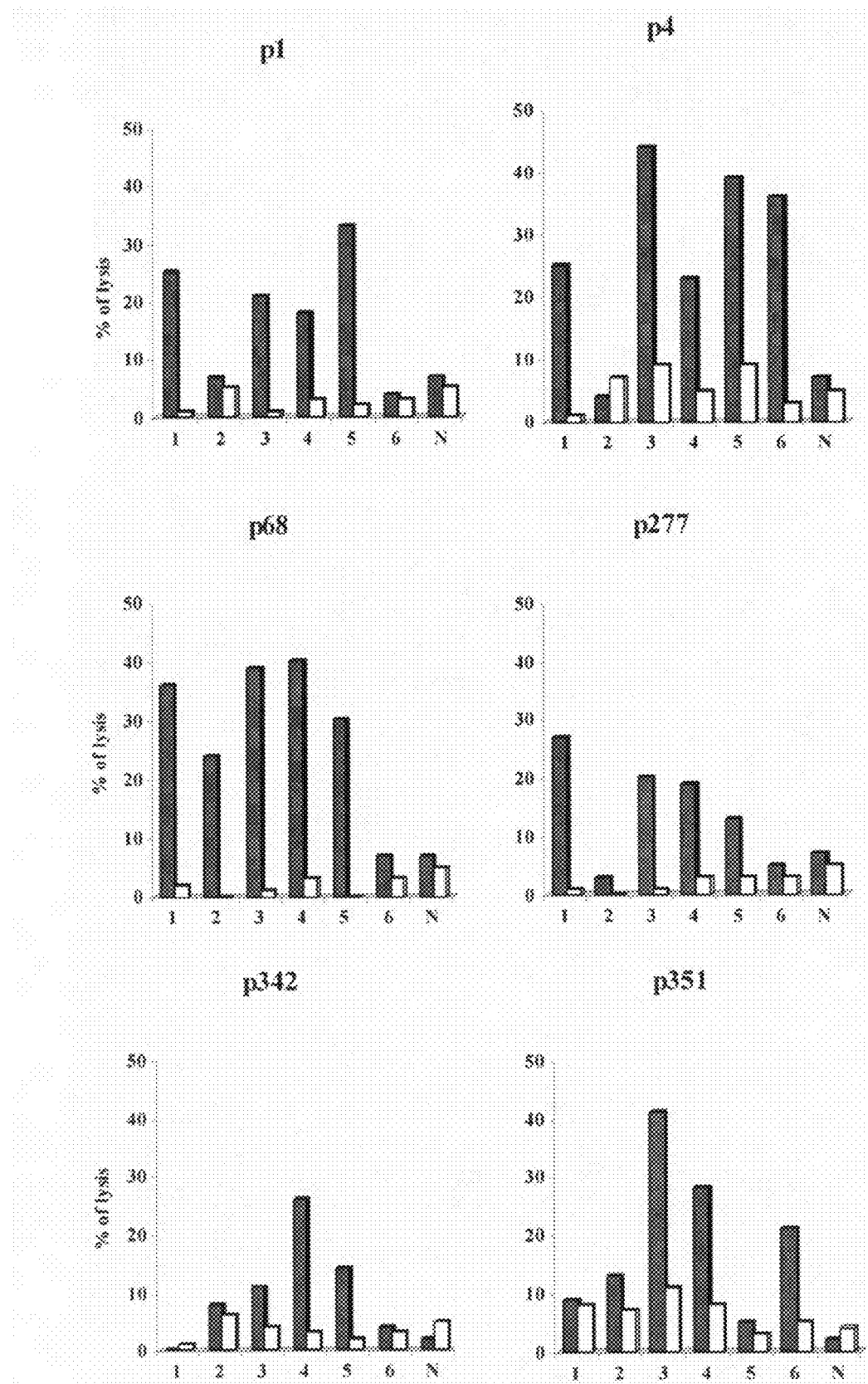

FIG. 2: hTERT derived peptides are processed in HLA-B0702 transgenic mice.

HLA-B7 Tg mice and one naïve mice (N) were immunized with 100 µg DNA encoding Htert. On day 14, spleen cells from each mouse were separately in vitro stimulated with different hTERT-derived peptides. Effector cells were essayed 6 days later against RMA-B7 targets loaded with relevant (■) or control (□) peptides as described in the material and methods. Percentage of lysis at a 60/1 ratio are shown (results from two independent experiments).

Figure 3:
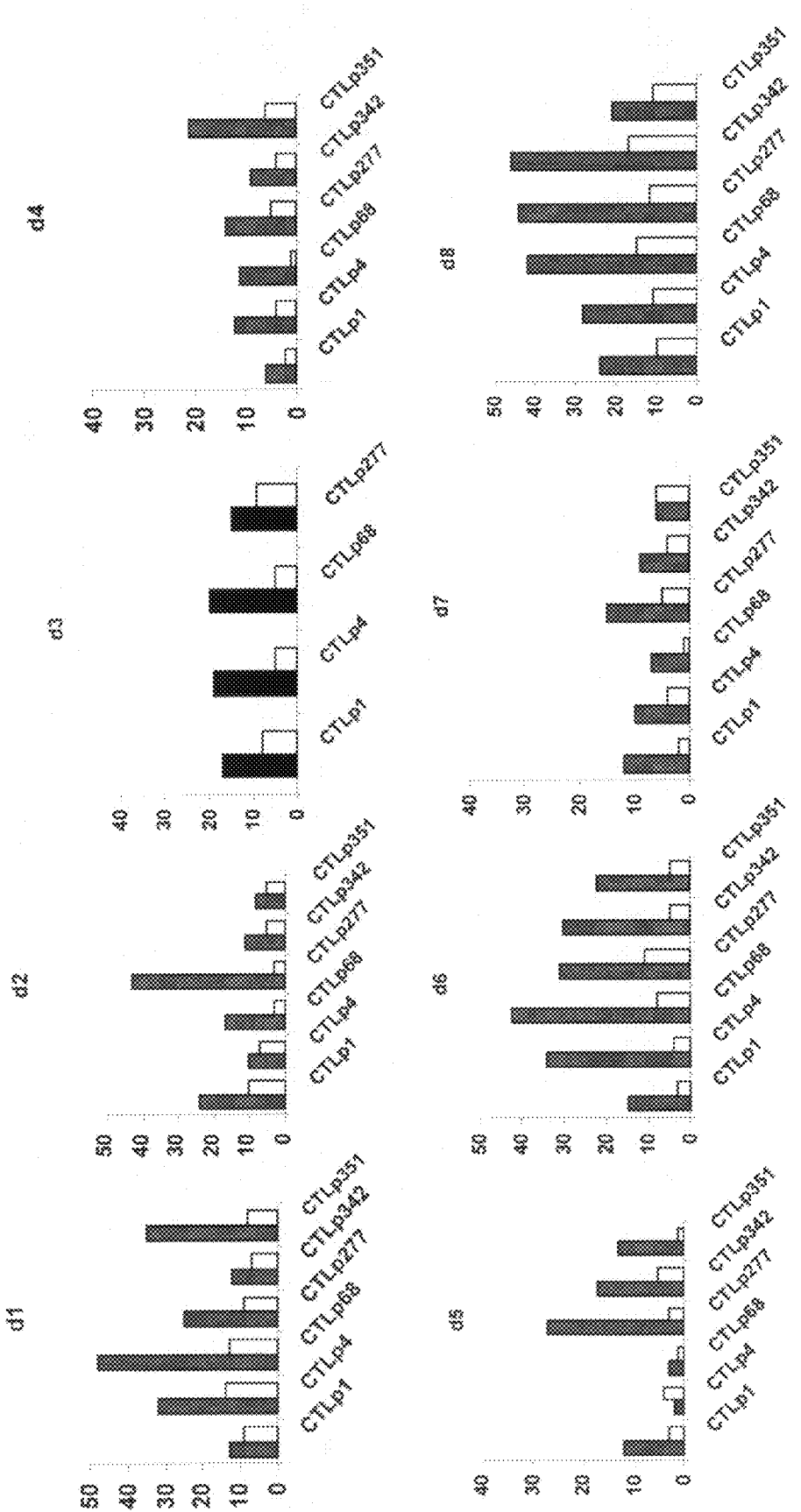

FIG. 3: Induction of CTL response against hTERT in PBMC from health blood donors.

T-lymphocyte cells from HLA-*B0702+ healthy donors were activated with each of the six hTERT peptide-pulsed autologous PBMC as detailed in materials and Method. After four rounds of weekly stimulation, effector cells, pulsed with relevant (■) or control (□) peptides, were essayed for lytic activity against $^{51}$Cr-labeled T2-B7 cells. Percentage of lysis at a 20/1 effector-target ratio is shown. Results from 8 out of 10 donors are presented (d1 to d8).

Figure 4:
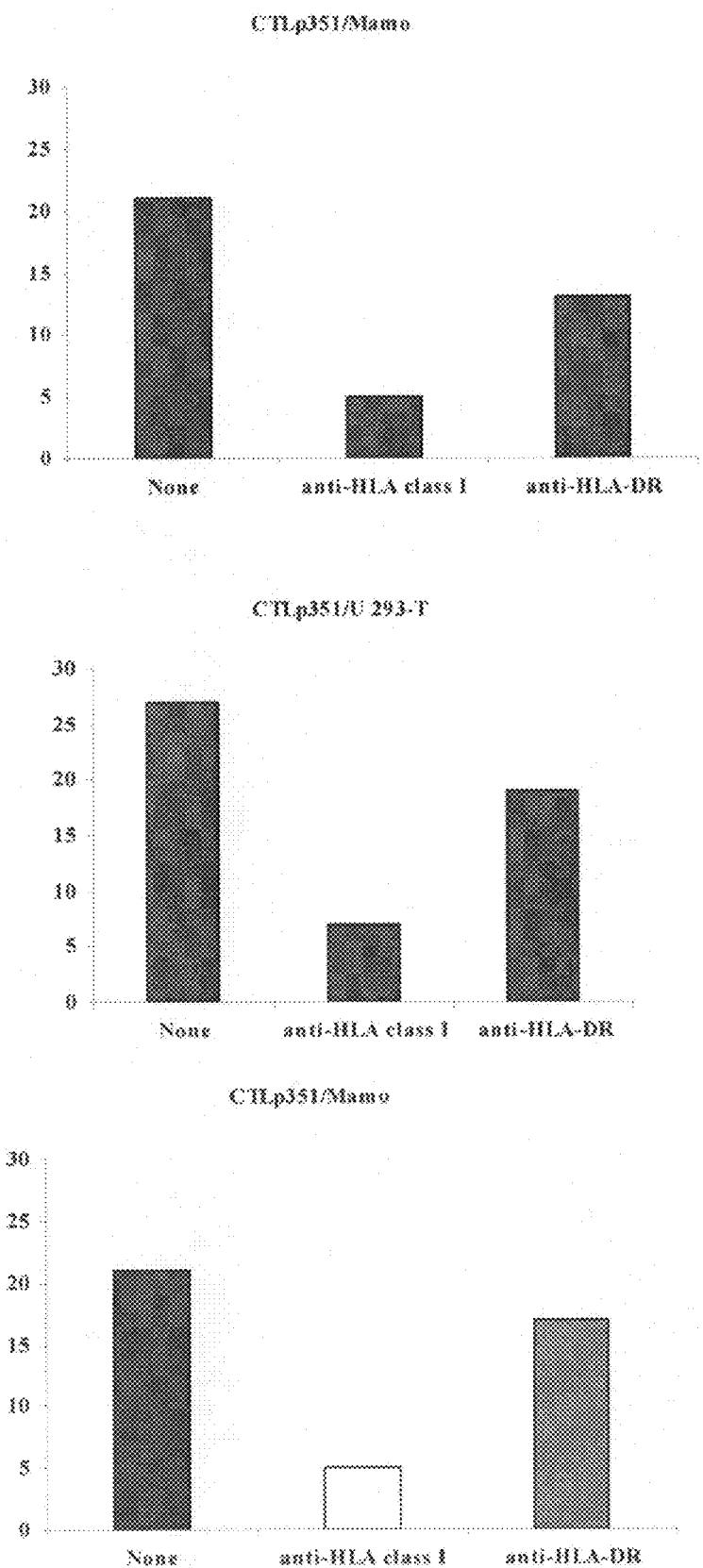

FIG. 4: Effect of an anti-HLA class I mAb on cytotoxicity of CTLp351 against tumor cells.

The cytotoxicity of the CTLp351 line against HLA-*B0702+ tumor cell lines Mamo and U293T pre-treated either in absence (none) or presence of HLA mAbs (anti-HLA class I mAb or an anti-class II mAb (HLA-DR)) was determined by standard $^{51}$Cr-release assay at effector-target ratio of 10/1.

FIG. 5: Ex-vivo detection of hTERT-specific T-cell response after Lv-hTERT immunization.

A) HLA-B7 transgenic mice were immunized with recombinant Trip-hTERT particles or control Trip-GFP (1500 ng). After 12 days, hTERT peptide-specific T cells producing IFNγ of each mouse were detected ex vivo by IFNγ-ELISPOT assay within freshly spleen cells. The number of IFNγ SFCs was calculated after subtracting negative control values. Results from three independent experiments are represented.

B) HHD mice were immunized with Trip-hTERT as described above. hTERT peptide-specific T cells producing IFNγ were detected ex vivo by ELISPOT as described above. Results from two independent experiments are represented.

Figure 6:
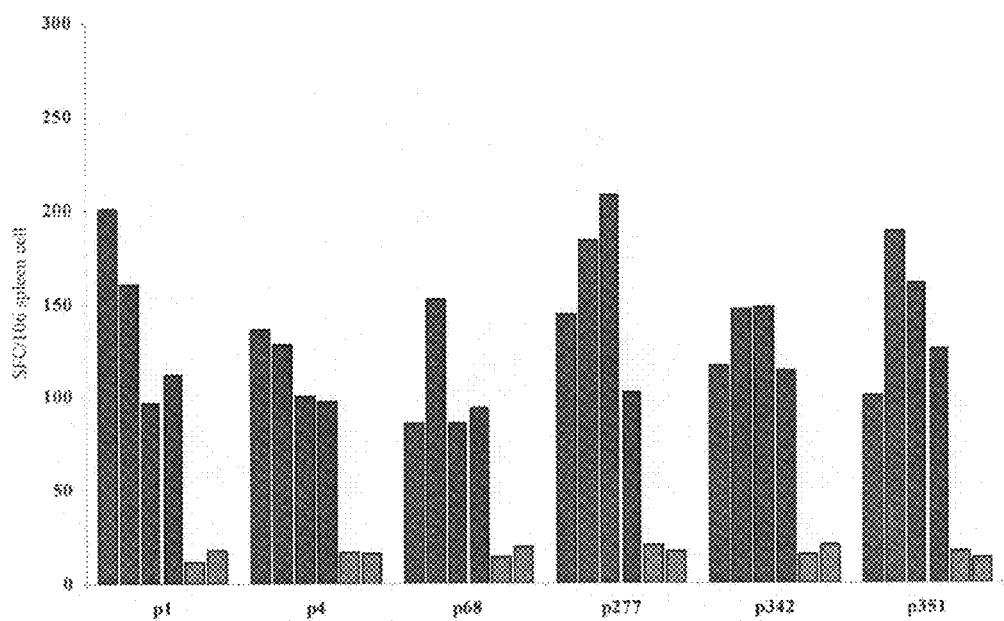

FIG. 6: Priming of specific CD8+ T cells responses in HLA-B*0702 transgenic mice following Trip-hTERT immunization HLA-B*0702 transgenic mice were immunized either with Trip-hTERT (4 first black bars) or control (2 last horizontal vertical stripe bars). 12 days later, IFN-γ producing-single cells within splenocytes of each mouse were detected ex vivo by IFN-γ ELISPOT assay. Ficoll purified lymphocytes from freshly isolated splenocytes of individual immunized mice were directly cultured with or without 5 μg/ml of each HLA-B*0702-restricted hTERT-derived peptides for 24 h. The number of specific-IFN-γ SFCs was calculated after subtracting non-specific values obtained with control without peptide (<15 SFC), and the responses were considered positive for SFC≧30.

Figure 7:
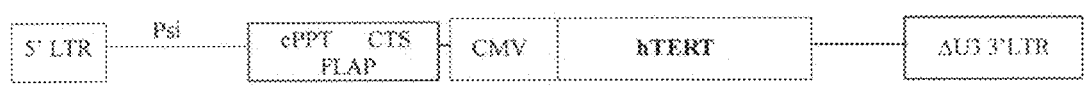

FIG. 7: Schematic representation of the pTRIP-hTERT

This lentiviral-derived vector contains the psi sequence, the cPPT and CTS central cis-active sequences (Flap) of the HIV-1 genome and the CMV promoter which allows the expression of the gene of interest. Moreover, the U3 domain is deleted in the 3'LTR (ΔU3).

FIG. 8:

A) DNA pTRIP-CMV-ΔhTERT immunization primed hTERT-specific CD8+ T cells responses in HHD mice. HHD mice (HLA-A2.1 Tg) were DNA immunized with a DNA encoding a non-functional form of HTERT (pTRIP-CMV-ΔhTERT). Ten days later, IFN-γ producing peptide-specific T cells were detected ex vivo by IFN-γ-ELISPOT assay. Ficoll purified lymphocytes from splenocytes of individual immunized mouse were directly cultured for 24 h, with or without 5 μg/ml of each HLA-A2.1-restricted hTERT-derived peptide. The number of specific-IFN-γ SFCs was calculated as described above. Responses were considered positive for SFC≧30.

B) Induction of short CTL responses in HHD mice after pTRIP-CMV-ΔhTERT immunization. HHD mice were immunized with a DNA encoding a non-functional form of HTERT (pTRIP-CMV-ΔhTERT) for 10 days. Spleen cells from individual mice were restimulated in vitro with HLA-A2.1-restricted hTERT-derived p540 and pY572 peptides for 6 days. Effector cells were tested in a $^{51}$Cr-release assay against HHD-transfected EL4 cells loaded with either the relevant peptide or the irrelevant peptide.

FIG. 9: Sequence of a non-functional hTERT protein (deletion of amino acids 867 to 869), DNA sequence disclosed as SEQ ID NO: 38 and amino acid sequence disclosed as SEQ ID NO: 39.

The coding sequence is located between the nucleotide 59 and 3348. Initiation and termination codons are underlined. First line is the nucleotide sequence; second line is the corresponding amino acid sequence. Third line is the numerotation of the hTERT coding sequence, starting from the initiation codon as the first amino acid.

FIG. 10: Sequence of a non-functional hTERT protein (deletion of amino acids 864 to 872). DNA sequence disclosed as SEQ ID NO: 40 and amino acid sequence disclosed as SEQ ID NO: 41.

The coding sequence is located between the nucleotide 59 and 3430. Initiation and termination codons are underlined. First line is the nucleotide sequence; second line is the corresponding amino acid sequence. Third line is the numerotation of the hTERT coding sequence, starting from the initiation codon as the first amino acid.

Figure 11:
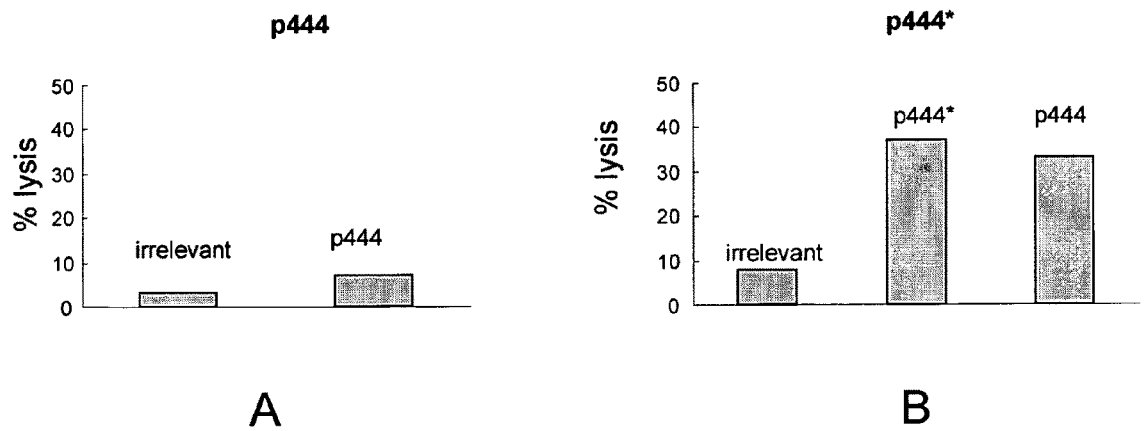

FIG. 11: Immunogenicity of p444 and p444* HLA-B*0702 restricted peptides.

(A) Immunogenicity of p444. CTL were tested against RMA-B7 targets loaded with peptide as indicated. (B) Immunogenicity of p444* peptide. CTL were tested against RMA-B7 targets loaded with p444*, p444 and an irrelevant peptide as indicated.

FIG. 12: Recognition of endogenous TERT by p444 specific murine CTL.

(A) CTL were tested against RMA-B7 targets loaded with decreasing doses of p444 or p444* peptides as indicated. (B) CTL were tested against COS cells transfected with HLA-B*0702 and/or TERT as indicated FIG. 13: Induction of p444* specific human CTL.

CTL were stimulated with T2-cells loaded with peptides as indicated. CTL maximal activation is obtained by PMA/ionomycin treatment.

EXAMPLES

I

Materials and Methods

Blood Donors

Peripheral bloods samples were obtained following written informed consent from adult healthy platelet donors (centre de transfusion sanguine de l'hôpital Mondor, Créteil, France). HLA typing of peripheral blood donors was performed in the HLA laboratory of the H. Mondor. Hospital Creteil (France). The study was approved by the French Blood Bank Institute.

Mice

HLA-*B0702 transgenic (Tg) mice, expressing an HLA-B0702 α1α2, H2-Kd α3 chimeric construct, in combination with constitutive murine β2-m molecule (HLA-B7$^{mα3}$) and HHD transgenic mice expressing a chimeric HLA-A2.1/H2-Db molecule, were deleted of their H2-Db and H2-kb genes as previously described (Pascolo et al. J Exp Med 1997; 185: 2043-51; Rohrlich et al. Int Immunol 2003; 15:765-72). These mice are on a C57BL/6 background and were bred and maintained under specific pathogen-free conditions in our animal facility.

Tumor Cells Lines

The T-B hybrid T1, EBV-transformed B cell JY, renal cancer cell line U293T and Burkitt lymphoma cell Raji were from American type Culture Collection (ATCC). Melanoma cell lines (SK23MEL, LB34, and KUL68) were kindly provided by P. Coulie (Bruxell, Belgium) and EBV-transformed B cell BBG.1 and BC3 were kindly provided by H. Collandre (R.A.H.P., Grenoble, France).

HLA-*B0702 transfected TAP deficient T2 cells (T2-B7) were kindly provided by P. Cresswell (Smith et al. J Immunol 1996; 156:3755-64). Murine lymphoma cell lines RMA, and EL4 were from ATCC; theses cells were also transfected with HLA-*B0702 gene and used as target cells Epitope Selection Peptide Synthesis We used predictive algorithm "SYFPEITHI" (Lu and Celis E Cancer Res 2000; 60:5223-7) to analyse amino acid sequence of hTERT for the existence of 9-amino acid (nonamer) or 10-amino acid (decamer) peptides, predicted to bind to HLA-*B0702. We selected candidate peptides that contain canonical HLA-B7-binding anchors, Pro at position 2 and hydrophobic aliphatic (Ala or Leu) at carboxyl-termini, and according to their highest predictive score. Six peptides were retained and synthesized, three 9-amino acid peptides named p1, (MPRAPRCRA (SEQ ID NO: 6), residues 1-9), p277 (RPAEEATSL (SEQ ID NO: 9), residues 277-285) and p342 (RPSFLLSSL (SEQ ID NO: 10), residues 342-350), and three 10-amino acid peptides, p4 (APRCRAVRSL (SEQ ID NO: 7), residues 4-13) p68, (APSFRQVSCL (SEQ ID NO: 8), residues 68-77), and p351 (RPSLTGARRL (SEQ ID NO: 11), residues 351-360) (anchor positions are underlined).

Peptides derived from human cytomegalovirus pp65, RPHERNGFTV (SEQ ID NO: 33) (R10TV), and human immunodeficiency virus type 1 IPRRIRQGL (SEQ ID NO: 34) were synthesized and were used as control peptides. Peptide derived from hepatitis B virus core 128-140 (TPPATRPPNAPIL (SEQ ID NO: 35)) was used as helper peptide for peptide immunization in mice. Peptides were purchased from PRIM to a minimum purity 80% and were reconstituted in distilled water or DMSO at a concentration of 2 mg/ml.

HLA-B0702 Binding/Stabilization Assay

The relative avidity of hTERT derived peptides for HLA-*B0702 was measured by using a MHC stabilization assay on HLAB0702 transfected T2 (T2-B7) cells in comparison with a reference peptide (R10TV) as described (Rohrlich et al. Int Immunol 2003; 15:765-72). Briefly, T2-B7 were incubated overnight at 2×10$^5$ cells/well in 96-well plates in serum free medium AIM-V (Invitrogen Corp., Gibco), supplemented with 100 ng/ml of human β2-microglobulin, in the absence (negative control) or in the presence of either reference peptide R10V or hTERT peptides at various final concentrations (100, 10, 1 and 0.1 µM). T2-B7 cells were labelled with a saturating concentration of ME.1 an anti-HLA-B7 mAb, then washed twice and finally stained with FITC-conjugated F(ab')2 goat anti-mouse Ig before flow cytometry.

Results are expressed as values of relative avidity, that is the ratio of concentration of test peptide necessary to reach 20% of the maximal binding (obtained with the reference peptide) over the concentration of the reference peptide. Therefore, the lower the value, the stronger the binding.

Peptide Immunization of HLA-*B0702 Transgenic Mice for CTL Induction

Female HLA-*B0702 transgenic mice at 8-10 weeks of age were injected subcutaneously (s.c.) at the base of the tail with 50 µg of individual HLA-B0702 restricted hTERT peptides supplemented with 140 µg of helper peptide co-emulsified in incomplete Freund's adjuvant (Difco, Detroit, Mich.). Ten days later, spleen cells of individual mouse were re-activated in vitro with relevant peptide in six wells plate. Effector CTL cells were tested in a standard 4-5 h $^{51}$Cr-release assay, using relevant or negative control peptide-pulsed, HLA-*B0702 transfected RMA cells (RMA-B7). Mice were considered as responders, when specific lysis ≧10% was observed.

DNA Immunization in HLA-*B0702 Transgenic Mice

The LvCMV-hTERT plasmid vector encoding the hTERT gene under the control of CMV promotor was purified on plasmid Giga kit columns under endotoxin-free conditions (Qiagen). Anesthetized HLA-*B0702 Transgenic mice were injected with said plasmid (50 µg each side) into regenerating tibialis anterior muscles. 14 days after, spleen cells of individual mouse were re-activated in vitro with peptide-pulsed (10 µg/ml), syngenic γ-irradiated (50 Gy) LPS-lymphoblast in complete medium, supplemented with 10% supernatant from Con A-activated rat spleens cells. Cytotoxicity assays were performed 6 days as described.

Lentiviral Vector Construct and Production

The pTRIP-deltaU3-CMV-hTERT (referred as TRIPLv-hTERT or Lv-hTERT or pTrip-hTERT) (FIG. 7) construct was created by first subcloning an EcoRI-SalI hTERT insert derived from the pBABE-hygro-hTERT plasmid (Counter et al. Proc Natl Acad Sci U.S.A. 1998; 95:14723-8) into the pSP73 vector (Promega). A BglII-SalI fragment was then inserted into the pTRIP-CMV plasmid cut with BamH1 and XhoI. Pseudo typed recombinant retroviral particles were produced by transient (48 h) transfection of 293T cells as described (Zenriou et al. Cell 2000; 14; 101:173; Firat et al. J Gene Med 2002; 4:38-45). The recombinant retroviral particles were concentrated by ultra-centrifugation and resuspended in PBS. The amount of vector particles was estimated from that of p24 protein in a commercially available ELISA assay (NEN, DUPONT, France Perkin Elmer).

The pTRIP-CMV-ΔhTERT vector, deposited at the CNCM (Institut Pasteur, Paris, France) under the number CNCM I-3660 on Jul. 28, 2006, was carried out as described in the paragraph above. However, the hTERT protein was rendered non-functional by deletion of amino acids 867 to 869, corresponding to nucleotides 2654 to 2662 of FIG. 1 (wild-type). The catalytically dead hTERT RT mutant (ΔhTERT) was generated by creating a deletion of amino acid residues 867 to 869 using the QuickChange XL Site-Directed Mutagenesis Kit (Stratagene) and verified by sequencing.

Immunization in MHC class I Transgenic Mice and CTL Detection

Immunization with TRIPLv-hTERT was performed as a single subcutaneously (at the base of the tail) injection of 1500 ng of TripLv-hTERT suspension or control vector.

Immunization was performed in HLA.A2 transgenic mice as a single intraperitoneal injection of recombinant lentiviral particles, pTRIP-CMV-ΔhTERT or Trip-GFP as a control, equivalent to 1500 ng of p24 antigen in 500 µl of PBS.

12 days later, hTERT peptide-specific T among splenocytes were detected by an ELISPOT assay (see below). Cytotoxicity assays were performed on the same immune splenocyte populations after in vitro stimulation with peptide-pulsed as described above.

Evaluation of T-Cell Response by Ex Vivo IFN-γ ELISPOT Assay

Peptide-specific T cells from immunized mice were detected by IFN-γ ELISPOT assay as previously described (Miyahira et al. J Immunol Methods 1995; 181:45-54). Anti-mouse IFN-γ mAb's (3 µg/ml; Pharmigen, Becton Dickinson biosciences) were coated onto 96-well nitrocellulose microplates (multi screen; Millipore corp, Molsheim, France). After red cell lysis, freshly isolate spleen lymphocytes of individual mouse ($5 \times 10^5$, $2.5 \times 10^5$ and $1.25 \times 10^5$ cells/well) were directly cultured with or without 5 µg of native hTERT peptide for 18 h at 37° C. After washings, the plates were incubated 2 hours with biotinylated anti-mouse IFN-γ (2 µg/ml; Pharmigen, Becton Dickinson biosciences). Finally, the plates were washed and incubated at 37° C. for 1 h with alkaline phosphatase-conjugate streptavidin (Roche molecular biochemicals, Mannheim, germany). Positive controls include cells stimulated with phorbol myristate acetate (100 ng/ml, Sigma)) and ionomycin (1 µg/ml). IFNγ spot-forming cells (SFCs) were developed by adding peroxidase substrates (BCIP/NBT, Promega Corp, Madison W; USA) and counted using automated image analysis system a Bioreader 2000 (Biosys, Karben, germany). The number of specific SFCs was calculated after subtracting negative control values (<10 SFC). Responses were positive if the mean of SFCs in stimulated well was greater than the mean+2 S.D. of the SFCs in the negative control wells and greater than 50 SFC/$10^6$ cells.

Cytolytic Assay

Cytotoxicity assays were performed by using standard 4-5 h $^{51}$Cr release assay as previously described (Firat et al. J Gene Med 2002; 4:38-45). Specific lysis in % was calculated by subtracting non-specific lysis observed with the control peptide. Mice were considered as responders when specific lysis ≧10% was observed.

Generation of hTERT Peptide-Specific CTL in Human

Human CTL from donors were obtained after in vitro re-activated PBMC for 4 weeks with hTERT peptide HLA-B0702 restricted as described previously (Hernandez et al. Proc Natl Acad Sci U.S.A. 2002; 99:12275-80). Briefly, Ficoll-purified human PBMCS were thawed and incubated ($4 \times 10^6$/well) in 24-well plates in RPMI 1640, 1 mM sodium pyruvate, 100 IU/ml penicillin, 100 µg/ml streptomycin, 10 mM HEPES, 5×10-5 M 2-mercaptoethanol supplemented with heat inactivated 10% human serum (Institut Jacques Boy, Reims, France). They were stimulated with each hTERT peptide (10 µg/ml) and recombinant human IL-7 (20 ng/ml; R&D Systems) was added.

On day 7, lymphocytes were re-activated with peptide-pulsed γ-irradiated autologous PBMCs (50 Gy). The next day, 20 IU/ml human IL-2 (Roche, Mannheim, Germany) was added to the culture. CTL lines were re-activated weekly during four cycles. For some donors, CD8$^+$ T cells were purified after three round cycle, using CD8 microbeads (Miltenyi Biotec, Bergisch Gladbach, Germany.) according to manufacturer's recommendations and activated once before functional test. Cytolytic assays were performed 6 days after the last re-activation against various $^{51}$Cr-labeled targets: T2-B7 pulsed with tested hTERT peptides or irrelevant peptide, or tumor cell lines.

In some experiments, tumors cells were incubated with an anti-HLA class I framework mAb, w6/32 (BD Pharmigen) or anti-HLA-*B0702 mAb, ME.1, or an anti-HLA-DR mAbB, G46.6 (BD Pharmigen) at an optimal concentration (10 µg/mL) for 30 minutes to determine whether cytotoxicity was restricted to HLA class I.

II

Results

1. Immunogenicity of HLA-*B-0702 Predicted Peptides Derived from hTERT.

Using a T-cell epitope prediction program, we analysed the hTERT protein sequence and retained six peptides (3 nonamers and 3 decamers) due to their high predictive score (Table I). We next tested their ability to bind HLA-B0702 molecule using antigen-transporter (TAP)-deficient T2 cells transfected with HLA-B0702 gene (T2-B7). Three peptides p1, p4 and p68 respectively show a high relative affinity (RA≦1) and the three others p277, p342 and p351 exhibited medium RA>1 (Table I). These data indicate that these six peptides are excellent binders to HLA-B0702. Therefore, one might expect such complexes, formed in the endoplasmic reticulum, to reach the surface of tumor cells and be available for CTL recognition.

To test if these peptides are immunogenic in vivo, we have immunized HLA-*B0702 transgenic mice. The six peptides tested were shown to be able to induce CTL responses, although differences were noticed (Table I). Two peptides p4 and p68, binding with a high affinity to the HLA-B7 molecules, induce strong CTL response in all mice tested. In contrast, peptides (p277 and p342), having lower affinity for the HLA-B7 molecules, enable the generation of moderate specific CTL, in only 50% of mice tested. CTL lines specific for hTERT epitopes, generated from transgenic mice, recognized human T2-B7 pulsed with their respective specific peptides (data not shown), demonstrating the high affinity of their TCR for the complex MHC/peptide. Thus, there is an overall correlation between the results of binding/stabilization of HLAB0702 and the in vivo CTL response in HLA-B7 transgenic mice.

TABLE 1

Immunogenicity of selected hTERT HLA-*B0702 binding peptide

| | | | | | Immunogenicity‡ | |
|---|---|---|---|---|---|---|
| Peptide* | Sequence | SEQ ID NO: | Score§ | Relative avidity† | R/T** | Specific Lysis (%) |
| p1 | MPRAPRCRA | 6 | 23 | 0.4 | 4/6 | 30, 39, 35, 28 |
| p4 | APRCRAVRSL | 7 | 25 | 0.3 | 6/6 | 52, 53, 48, 51, 46, 49 |

TABLE 1-continued

Immunogenicity of selected hTERT HLA-*B0702 binding peptide

| | | | | | Immunogenicity‡ | |
|---|---|---|---|---|---|---|
| Peptide* | Sequence | SEQ ID NO: | Score§ | Relative avidity† | R/T** | Specific Lysis (%) |
| p68 | APSFRQVSCL | 8 | 25 | 0.4 | 6/6 | 63, 78, 75, 69, 70, 72 |
| p277 | RPAEEATSL | 9 | 23 | 4.7 | 3/6 | 29, 33, 29 |
| p342 | RPSFLLSSL | 10 | 23 | 2.5 | 3/6 | 26, 39, 32, |
| p351 | RPSLTGARRL | 11 | 23 | 1.5 | 4/6 | 47, 31, 37, 26 |

*The figure represents the first amino acid of the peptide. Therefore, "p4" indicates that the alanine residue is the fourth amino acid of the coding sequence.
§Algorithm score obtained by using SYFPEITHI predictive program
†The relative avidity of hTERT peptides for HLA-B*0702 was measured by using a MHC stabilization assay in comparison with a reference peptide as detailed in material and methods.
‡HLA-B*0702 transgenic mice were immunized with candidate peptides (six mice for each peptide) as detailed above. Ten days later, spleen cells of individual mice were restimulated in vitro with each hTERT peptide. Cytolytic activities were assayed by 4-5 h 51Cr release assay using peptide loaded RMA-B7 target cells. The Specific lysis was calculated by subtracting non-specific lysis observed with the R10TV control peptide. Specific lysis at a 75:1 effector/target ratio was showed.
**R/T: responder (specific lysis ≥ 10%) versus tested mice.

2. hTERT-Derived Peptides were Processed in HLA-B0702 Transgenic Mice.

To assess the presentation of endogenously synthesized hTERT peptides in the context of the HLA-B0702 molecule against these six hTERT epitopes identified, HLA-*B0702 transgenic mice were immunised with cDNA encoding hTERT, forty days after peptide-specific CTL responses within spleen cells of individual mice were evaluated. As shown in FIG. 2, hTERT peptide-specific CTLs were induced in most immunized mice (M), from 50 to 80% of mice for p4, p68, p1, p277 and p351. In contrast, p342-specific CTLs can be induced in about 15% tested mice. No significant hTERT-specific CTL responses were also induced from non-immunized naïve mice. Thus, these six hTERT epitopes are effectively intracellularly processed. Moreover, natural peptides similar in term of amino acid sequence or structure to the synthetic ones, are presented by the corresponding HLA-*B0702 molecules on the cell surface.

Further, these data show that multiple CTL specificity can be induced simultaneously against several hTERT epitopes in a single mice and validate our HLA-Class I transgenic mouse model for their potential to test candidate vaccines.

3. Induction of Primary CTL Responses from Healthy Donors by hTERT Peptides.

We studied whether hTERT peptides would be effective in raising HLA-B7-restricted CTLs, using PBMCs of HLA-B0702 healthy donors in an in vitro immunization protocol. CTL responses were generated in eight out of ten individuals ($d_1$ to $d_8$), and peptide-specific CTL responses were obtained in at least 50% of donors, except for p342 (20%) (FIG. 3). hHTERT epitope recognition by in vitro generated CTLs varies among donors, depending upon their genetic background (FIG. 3). Therefore, by random testing of HLA-B0702 healthy donors, it was clearly established that these hTERT peptides are immunogenic in human, implying that specific CTL precursors for hTERT are not deleted in the peripheral adult repertoire. Therefore, we asked whether CTL lines generated from healthy donors would be able to kill HLA-matched hTERT+ tumor cells.

4. Specific hTERT CTL were Able to Lyse Tumors of Differents Origins hTERT-specific CTLs from donors were tested for their capacity to lyse human tumour cell lines of different origins. The results presented in Table 2 show that, CTL lines generated in vitro from healthy donors killed HLA-B0702+ tumour cells, whereas no cytotoxicity against HLA-B0702− tumors was detected. (See for example CTLp351 in $d_1$, $d_2$ and $d_3$ in KU L268 or 293-UT target (respectively 52, 25, 20 and 34, 41 and 19%) versus T1 or BBG1 target (respectively 9, 2, 6 and 0, 0, 2%). Differences were observed in tumor recognition according to the CTL specificity; this could be explained by differential presentation of hTERT peptides on the surface of the tumor cells. Importantly, p351-specific CTL lines generated from different donors recognize the majority of tumor cell lines tested (Table 2). In contrast, all p4-specific CTL lines do not lyse all the type of tested tumors. CTL lines, specific for p1 and p68 peptides, only recognize the T1-B7 targets. p342-specific CTL lines recognize only melanoma cells (LB 34 and KU 268 target). Finally, p277-specific CTL lines recognize renal cancer (293 UT) but neither melanoma nor lymphoid tumor cells. On the other hand, normal PBMCs and CD40 activated B cells were not lysed by these hTERT peptide-specific CTL lines, regardless of HLA type (two last lines of Table 2).

As shown in FIG. 4, the cytotoxic activity of CTLp351 line toward HLA-B7+ tumor cells is inhibited by an anti-class I mAb anti-HLA-B0702, but not by an anti-HLADR mAb (MHC class II). Similar data were obtained with other peptide-specific CTL lines (data not shown) and suggest that CTL lines exert cytotoxicity against hTERT+ tumor cells in an HLA-B0702-restricted manner. Collectively, these results show that these six hTERT derived peptides are not equally naturally expressed at the tumor cell surface and that hTERT peptide-specific CTLs can discriminate between tumor cells and normal cells, through the recognition of hTERT peptide in context of HLA-B0702 molecules.

5. Lentiviral Vector Encoding hTERT Vaccination Induces Efficient Peptide-Specific T Cell Responses in Mice.

We next tested candidate vaccines, comprising either a full-length hTERT gene or a non-functional hTERT gene, inserted in a HIV-derived flap vector (FIG. 7). Previous data have shown that lentiviral vectors of this type target dendritic cells in vitro and in vivo, and induce strong poly-specific anti tumor CTL responses in animals. Therefore, we immunized HLA-*B0702 transgenic mice with either recombinant Lv-hTERT or with pTRIP-CMV-ΔhTERT. Twelve days after, spleen cells of individual mice were evaluated by an ex vivo ELISPOT assay.

As shown in FIG. 5A, peptide-specific CD8+ T cell responses were obtained against HLA-B0702 restricted hTERT epitopes, as compared with mice that received Lv-GFP control vector. Functional analysis of the induced peptide-specific CD8+ cells in chromium release assay after in vitro stimulation confirmed ex vivo ELISPOT data (Table 3)

and show that efficient specific CTL response is generated against these six peptides in about 50-70% of mice after a single injection of Lv-hTERT and in 100% of the mice after a boost with TRIPLv-hTERT (FIG. 6). This was also associated with strong CTL responses in all mice (Table 3). Additionally, as show in Table 3, immunization of HHD mice transgenic for HLA-A2.1 with the same vector induced potent CTL responses specific for two HLA-A2.1.1 restricted epitopes previously classified as dominant (p540) and cryptic (p572). Collectively, these results clearly show that administration of Lv-hTERT result in the induction of very efficient multispecific T cell response in mice, supporting that hTERT could serve as polyepitope and polyallelic TAA for cancer immunotherapy.

Figures 8A, 8B:
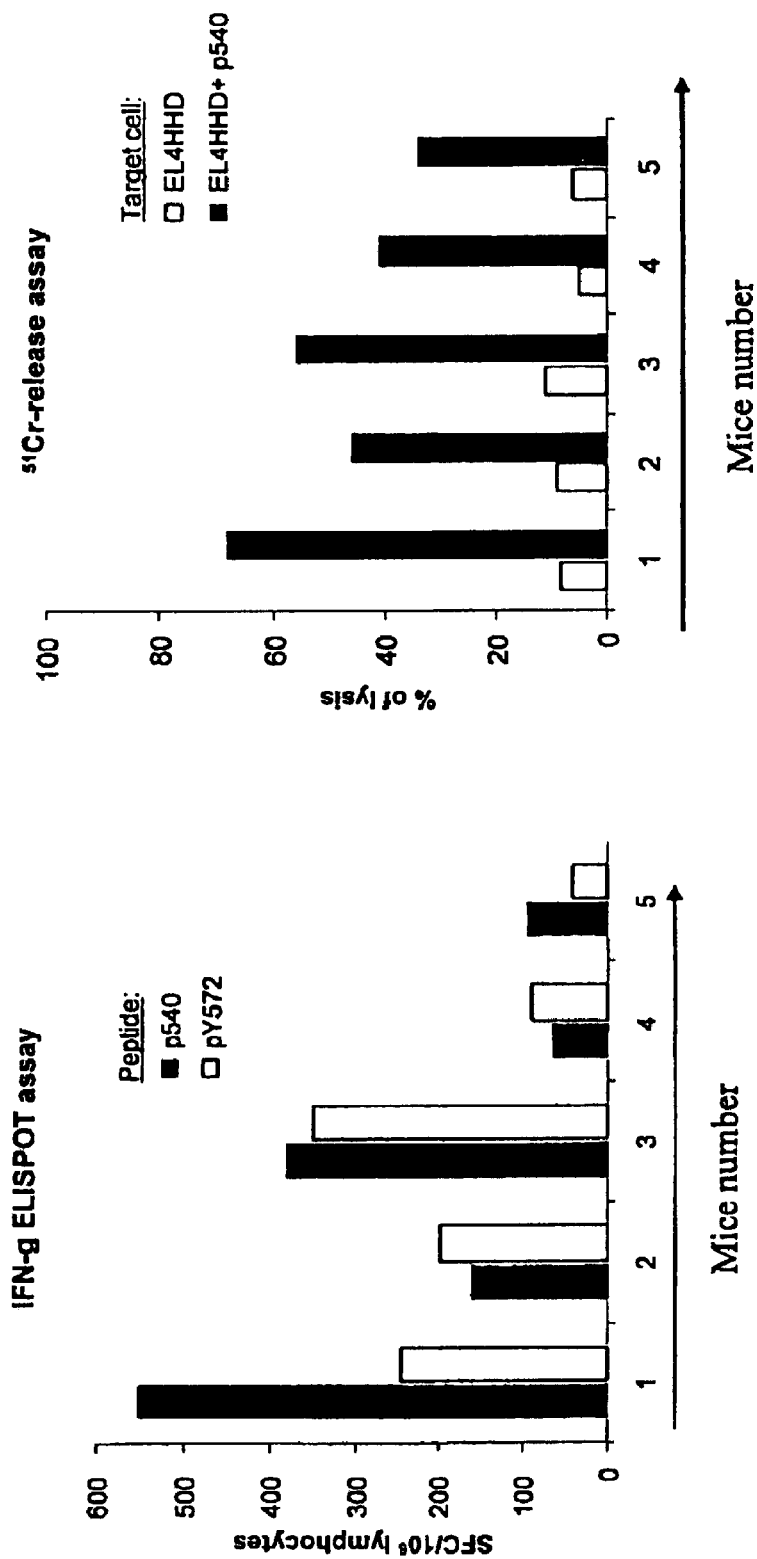

As shown in FIG. 8, hTERT peptide-specific CD8+ T cell responses were detected ex vivo in HLA-A2 transgenic (Tg) mice after a single injection of recombinant pTRIP-CMV-ΔhTERT. We showed that CD8+ T cells specific for p540 and PY572 epitopes were induced at least in 50% of immunized mice (FIG. 8). These results clearly showed that the two epitopes were correctly endogenously processed and presented in HLA-A2 Tg mice after immunization with pTRIP-CMV-ΔhTERT.

Collectively, these results showed that a single injection of TRIP-hTERT resulted in the induction of a potent multi-specific anti-hTERT CD8+ T-cells response in both HLA transgenic mice groups.

III

Conclusion

New hTERT epitopes, which are in vivo immunogenic and processed in H-2-class I knockout HLA-B0702 transgenic mice have identified. Further, in vitro, hTERT peptide immunization using HLA-B702+PBL from healthy donors induce specific CTL responses recognizing hTERT+ tumors from various origins, implying that there is no deletion in the human T cell repertoire for these epitopes. Moreover, it was shown that depending upon the tumor origins, peptides repertoire expressed on the cell surface could be qualitatively different, underlining, the utility to characterize hTERT as polyepitope tumor associated antigens for circumvent antigenic variability of cancer cells. Finally, a humanized HLA-*B0702 and HLA-A2 1 transgenic mice Were used, to test a candidate vaccine consisting of a non-functional telomerase gene inserted in a new generation of lentiviral derived flap vector. A strong hTERT specific CD8+ T cell responses were observed in all the HLA-transgenic mice. These data support the use for therapeutic vaccination in cancer patients and extend the potential applicability of hTERT as a therapeutic target to cover a large population of cancer patients.

TABLE 2 anti-hTRT CTL from normal donors lyses tumor cells of various types

| | | | Percent lysis* | | | | | | | | | | | | | | | | |
|---|---|---|---|---|---|---|---|---|---|---|---|---|---|---|---|---|---|---|---|
| | | | CTL p1 | | | CTL p4 | | | CTL p68 | | | CTL p277 | | | CTL p342 | | | CTL p351 | | |
| Cell target | Cell type | HLA-B7 | d1 | d6 | d8 | d1 | d6 | d8 | d1 | d6 | d8 | d1 | d6 | d8 | d1 | d6 | d8 | d1 | d6 | d8 |
| T1 | T-B hybrid | − | 9 | 10 | 5 | 8 | 6 | nd | 0 | 7 | 6 | 3 | 5 | 9 | 3 | 6 | 4 | 9 | 2 | 6 |
| T1-B7 | T-B hybrid | + | 29 | 26 | 14 | 5 | 7 | nd | 19 | 30 | 4 | 56 | 30 | 12 | 2 | 17 | 5 | 38 | 24 | 31 |
| Sk23mel | Melanoma | − | 0 | 1 | 0 | 0 | 2 | 0 | 10 | 3 | 4 | 1 | 4 | 0 | 4 | 4 | 3 | 5 | 2 | 1 |
| LB34 | Melanoma | + | 5 | 4 | 0 | 0 | 4 | 2 | 13 | 7 | 11 | 0 | 0 | 2 | 28 | 22 | 14 | 52 | 25 | 20 |
| KUL68 | Melanoma | + | 9 | 4 | 7 | 6 | 3 | 0 | 0 | nd | 0 | 7 | 4 | nd | 26 | 14 | 9 | 34 | 41 | 19 |
| 293-UT | Renal cell | + | 2 | 8 | 4 | 1 | 6 | 7 | 3 | 0 | 0 | 36 | 17 | 22 | 9 | 17 | 4 | 28 | 22 | 25 |
| BBG1 | EBV-B cell | − | 0 | 4 | 3 | 0 | 0 | 2 | 2 | 0 | 1 | 0 | 0 | 5 | 1 | 1 | 0 | 0 | 0 | 2 |
| JY | EBV-B cell | + | 2 | 0 | 4 | 0 | 6 | nd | 0 | 0 | 9 | 3 | 0 | 1 | 8 | 10 | 6 | 27 | 18 | 15 |
| Raji | B lymphoma | − | 4 | 1 | nd | 5 | 0 | nd | 0 | 0 | nd | 6 | nd | 1 | 0 | nd | 0 | 4 | 0 | nd |
| Autologous PBMC | Normal cell | + | 0 | 0 | 0 | 4 | 0 | 1 | 0 | 0 | 0 | 0 | 0 | 1 | 0 | 2 | 0 | 0 | 0 | 1 |
| Autologous B cell CD40§ | Normal cell | + | 0 | 0 | 0 | 3 | 0 | 2 | 2 | 0 | 0 | 0 | 0 | 6 | 0 | 2 | 3 | 0 | 0 | 4 |

*hTERT peptide specific-CTL lines (CTLp1, CTLp4, CTLp68, CTLp277, CTLp342, CTLp351) were obtained from healthy donors that were responder after subsequent in vitro immunization as described in material and methods. Cytotoxicity was measured in a standard $^{51}$Cr-labeled release assay. Specific lysis: for a 30:1 effector: target ratio were shown
§Autologous B lymphocytes from normal donors were activated for 48 h with a trimeric CD40 L (40 µg/ml).

TABLE 3

Induction of CTL responses following Lv-hTERT immunization
Flap+ Lv-hTRT immunization

| HLA-B7 Tg mice | | | HHD mice | | |
|---|---|---|---|---|---|
| Restimulating peptide | R/T | Specific lysis (%) | Restimulating peptide | R/T | Specific lysis (%) |
| P1 | 4/8 | 27, 30, 29, 32 | P540 | 2/6 | 21, 18 |
| P4 | 6/8 | 18, 25, 54, 33, 16 | pY572 | 5/6 | 22, 19, 14, 35, 24 |
| p68 | 4/8 | 15, 64, 24, 16, | | | |
| p277 | 5/8 | 21, 25, 23, 52, 33 | | | |
| p342 | 4/8 | 18, 24, 20, 37 | | | |
| p351 | 5/8 | 17, 20, 18, 36, 19 | | | |

IV

Supplementary Examples

The examples have been performed using the following materials and methods:

Transgenic Mice. The HLA-B7H-2 class-I knockout mice were previously described (Rohrlich et al., 2003).

Cells. HLA-B*0702 transfected murine RMA-B7 and human T2-B7 cells were previously described (Rohrlich et al., 2003) and were grown in FCS 10% supplemented RPMI 1640 culture medium.

Peptides and Plasmids. Peptides were synthesized by Epytop (Nîmes, France). HLA-B*0702 plasmid was provided by Dr. Lemonnier (Institut Pasteur, Paris, France) (Rohrlich et al., 2003) and TERT plasmid was provided by Dr Weinberg (MIT, Boston, Mass.) (Meyerson et al, 1997).

Measurement of Peptide Relative Affinity to HLA-B*0702. The protocol used has been described previously (Rohrlich et al., 2003). Briefly, T2-B7 cells were incubated at 37° C. for 16 hours with peptides concentrations ranging from 100 μM to 0.1 μM, and then stained with ME-1 monoclonal antibody (mAb) to quantify the surface expression of HLA-B*0702. For each peptide concentration, the HLA-B*0702 specific staining was calculated as the percentage of staining obtained with 100 μM of the reference peptide $CMV_{265-274}$. The relative affinity (RA) was determined as: RA=(Concentration of each peptide that induces 20% of HLA-B*0702-expression/Concentration of the reference peptide that induces 20% of HLA-B*0702 expression).

CTL Induction in vivo in HLA-B*0702 Transgenic Mice. Mice were injected subcutaneously with 100 μg of peptide emulsified in Incomplete Freund's Adjuvant (IFA) in the presence of 150 μg of the I-$A^b$ restricted $HBVcore_{128}$ T helper epitope. After 11 days, 5×$10^7$ spleen cells were stimulated in vitro with peptide (10 μM). On day 6 of culture, the bulk responder populations were tested for specific cytotoxicity.

Peptide Processing Assay on COS-7 Transfected Cells. 2.2×$10^4$ simian COS-7 cells were plated in flat-bottomed 96-well plates in DMEM+10% FCS, in triplicate for each condition. Eighteen hours later, cells were transfected with 100 ng of each DNA plasmid with DEAE Dextran. After 4 hours, PBS+10% DMSO was added for 2 minutes. Transfected COS cells were incubated in DMEM+10% FCS during 40 hours and then used to stimulate murine CTL in a TNFα secretion assay.

TNFα Secretion Assay. Transfected COS-7 cells at day 4 were suspended in 50 μl of RPMI+10% FCS and used as stimulating cells. 5×$10^4$ murine T cells were then added in 50 μl RPMI 10% FCS and incubated for 6 hours. Each condition was tested in triplicate. 50 μl of the supernatant was collected to measure TNFα. Standard dilutions were prepared in 50 μl with final doses of TNFα ranging from 104 to 0 pg/ml. On both the supernatants and the standard dilutions, 3×$10^4$ TNFα sensitive WEHI-164c13 cells in 50 μl were added. They were incubated for 16 h at 37° C. Inhibition of cell proliferation was evaluated by the MTT colorimetric method (Espevik and Nissen-Meyer, 1986).

Generation of CTL from human PBMC. PBMC were collected by leukapheresis from healthy HLA-B*0702 volunteers. Dendritic cells (DC) were produced from adherent cells cultured for seven days (2×$10^6$ cells/ml) in the presence of 500 IU/ml GM-CSF and 500 IU/ml IL-4 (R&D Systems, Minneapolis, Minn.) in complete medium (RPMI-1640 supplemented with 10% heat inactivated human AB serum, 2 μM L-Glutamine and antibiotics). On day seven, DC were pulsed with 10 μM peptides for 2 hrs; maturation agents Poly I:C (Sigma, Oakville, Canada) at 100 ng/ml and anti-CD40 mAb (clone G28-5, ATCC, Manassas, Va.) at 2 μg/ml were added in the culture and DCs were incubated at 37° C. overnight or up to 48 hours. Mature DC were then irradiated (3500 rads). $CD8^+$ cells were purified by positive selection with CD8 MicroBeads (Miltenyi Biotec, Auburn, Calif.) according to the manufacturer's instructions. 2×$10^5$ $CD8^+$ cells+6× $10^4$ $CD8^-$ cells were stimulated with 2×$10^4$ peptide pulsed DC in complete culture medium supplemented with 1000 IU/ml IL-6 and 5 IU/ml IL-12 (R&D Systems, Minneapolis, Minn.) in round-bottomed 96 well plates. From day seven, cultures were weekly restimulated with peptide-loaded DC in the presence of 20 IU/ml IL-2 (Proleukin, Chiron Corp., Emeryville, Calif.) and 10 ng/ml IL-7 (R&D Systems, Minneapolis, Minn.). After the third in vitro restimulation, bulk cell cultures were tested for IFNγ intracellular staining.

Cytotoxic assay. Targets were labelled with 100 μCi of $Cr^{51}$ for 60 min, plated in 96-well V-bottomed plates (3×$10^3$ cell/well in 100 μL of RPMI 1640 medium) and, when necessary, pulsed with peptides (1 μM) at 37° C. for 2 hours. Effectors were then added in the wells and incubated at 37° C. for 4 hours. Percentage of specific lysis was determined as: % Lysis=(Experimental Release−Spontaneous Release)/(Maximal Release−Spontaneous Release)×100.

IFNα intracellular staining. T cells ($10^5$) were incubated with 2×$10^5$ T2-B7 cells loaded with stimulating peptide in the presence of 20 μg/ml Brefeldin-A (Sigma, Oakville, Canada). Six hours later they were washed, stained with r-phycoerythrin-conjugated anti-CD8 antibody (Caltag Laboratories, Burlingame, Calif., USA) in PBS for 25 min at 4° C., washed again, and fixed with 4% PFA. The cells were then permeabilized with PBS, 0.5% BSA, 0.2% saponin (Sigma, Oakville, Canada), and labeled with an allophycocyanin-conjugated anti-IFNγ mAb (PharMingen, Mississauga, Canada) for 25 min at 4° C. before analysis with a FACSCalibur® flow cytometer.

Example 1

Affinity of p444 and p444* Peptides p444 peptide with the HLA-B*0702 specific anchor motifs, i.e. P2 and L at C-terminal position (Sidney et al., 1996) belonging to TERT antigen was tested for binding to the HLA-B*0702 molecule. p444 was not able to bind to the HLA-B*0702. This demonstrates that the presence of anchor motifs is not sufficient to ensure a high binding affinity to HLA-B*0702. Enhancement of HLA-B*0702 affinity of p444 should, therefore require the replacement of unfavourable secondary anchor motifs with favourable motifs. Our interest was focused on the secondary anchor position 1 where alanine has been described to be favourable (Sidney, Southwood et al., 1996). Indeed, p444 modified at the first position with an alanine (p444*) exhibits a strong affinity for the HLA-B*0702 molecule (table 1).

TABLE I

| p444 and p444* HLA-B*0702 affinity of peptides | | |
|---|---|---|
| peptide | séquence | RA |
| p444 | DPRRLVQLL | >10 |
| p444* | APRRLVQLL | 1.4 |

Example 2

Immunogenicity of p444 and p444* Peptides p444 and p444* peptides have been tested for their capacity to induce a specific CTL immune response in HLA-B7 transgenic mice. Only the high affinity p444* was immunogenic confirming that immunogenicity of peptides is strongly related to their affinity for HLA (FIG. 11). Moreover, p444* generated CTL recognized the optimized peptide and the corresponding native peptide.

Example 3

CTL Induced by P444* Peptide Recognize Endogenous TERT p444* was tested for its ability to induce CTL able to recognize endogenous TERT. HLA-B7 transgenic mice were then immunized with the p444* and eleven days later their spleen cells were in vitro stimulated with the native p444 peptide. Generated CTL killed RMA-B7 targets loaded with decreasing concentrations of p444* and p444 peptides. The half maximal lysis of p444 loaded and p444* loaded targets was obtained with 5.5 nM and 1 nM respectively (FIG. 12A). CTL were then tested for their capacity to recognize COS-7 cells expressing HLA-B*0702 and endogenous TERT. Results presented in FIG. 12B show that CTL recognized COS-7 cells transfected with both HLA-B*0702 and TERT but not COS-7 cells transfected with either HLA-B*0702 or TERT demonstrating that p444 is an HLA-B*0702 restricted epitope naturally processed from endogenous TERT.

Example 4

P444* Stimulates CTL from Healthy Donors

Figure 13:
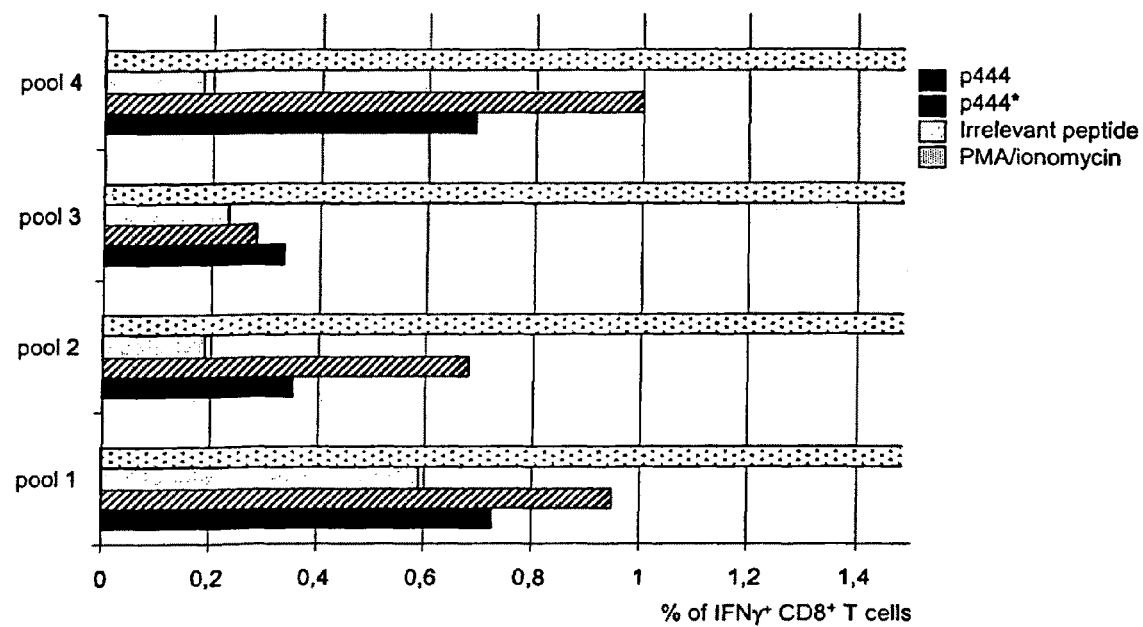

CD8 cells from healthy donors were in vitro stimulated with autologous dendritic cells loaded with p444* peptide. After four stimulations, proliferating cells were divided into 4 pools. Each pool was then tested for intracellular IFNg production upon stimulation with T2-B7 cells loaded with optimized p444* or native p444. Results from D5609 responding donor are presented in Figure. IFNγ producing CTL were detected in pools 2 and 4 after stimulation with either p444 or p444* loaded T2B7 cells (FIG. 13).

BIBLIOGRAPHY

Schroers R, Huang X F, Hammer J, Zhang J, Chen S Y Identification of HLA DR7-restricted epitopes from human telomerase reverse transcriptase recognized by CD4+ T-helper cells. Cancer Res. 2002 May 1; 62(9): 2600-5.

Vonderheide R H, Domchek S M, Schultze J L, George D J, Hoar K M, Chen D Y, Stephans K F, Masutomi K, Loda M, Xia Z, Anderson K S, Hahn W C, Nadler L M. Vaccination of cancer patients against telomerase induces functional antitumor CD8+ T lymphocytes. Clin Cancer Res. 2004 Feb. 1; 10(3):828-39.

Gross D A, Graff-Dubois S, Opolon P, Comet S, Alves P, Bennaceur-Griscelli A, Faure O, Guillaume P, Firat H, Chouaib S, Lemonnier F A, Davoust J, Miconnet I, Vonderheide R H, Kosmatopoulos K. High vaccination efficiency of low-affinity epitopes in antitumor immunotherapy. J Clin Invest. 2004 February; 113(3):425-33.

Scardino A, Gross D A, Alves P, Schultze J L, Graff-Dubois S, Faure O, Tourdot S, Chouaib S, Nadler L M, Lemonnier F A, Vonderheide R H, Cardoso M, Kosmatopoulos K. HER-2/neu and hTERT cryptic epitopes as novel targets for broad spectrum tumor immunotherapy. J. Immunol. 2002 Jun. 1; 168(11):5900-6.

Vonderheide R H, Schultze J L, Anderson K S, Maecker B, Butler M O, Xia Z, Kuroda M J, von Bergwelt-Baildon M S, Bedor M M, Hoar K M, Schnipper D R, Brooks M W, Letvin N L, Stephans K F, Wucherpfennig K W, Hahn W C, Nadler L M. Equivalent induction of telomerase-specific cytotoxic T lymphocytes from tumor-bearing patients and healthy individuals. Cancer Res. 2001 Dec. 1; 61 (23): 8366-70.

Vonderheide R H, Anderson K S, Hahn W C, Butler M O, Schultze J L, Nadler L M. Characterization of HLA-A3-restricted cytotoxic T lymphocytes reactive against the widely expressed tumor antigen telomerase. Clin Cancer Res. 2001 November; 7(11):3343-8.

Vonderheide R H, Hahn W C, Schultze J L, Nadler L M. The telomerase catalytic subunit is a widely expressed tumor-associated antigen recognized by cytotoxic T lymphocytes. Immunity. 1999 June; 10(6):673-9.

Minev B, Hipp J, Firat H, Schmidt J D, Langlade-Demoyen P, Zanetti M. Cytotoxic T cell immunity against telomerase reverse transcriptase in humans. Proc Natl Acad Sci USA. 2000 Apr. 25; 97(9):4796-801.

Hernandez J, Garcia-Pons F, Lone Y C, Firat H, Schmidt J D, Langlade-Demoyen P, Zanetti M. Identification of a human telomerase reverse transcriptase peptide of low affinity for HLA A2.1 that induces cytotoxic T lymphocytes and mediates lysis of tumor cells. Proc Natl Acad Sci USA. 2002 Sep. 17; 99(19):12275-80. Epub 2002 Sep. 6.

Arai J, Yasukawa M, Ohminami H, Kakimoto M, Hasegawa A, Fujita S. Identification of human telomerase reverse transcriptase-derived peptides that induce HLA-A24-restricted antileukemia cytotoxic T lymphocytes. Blood. 2001 May 1; 97(9):2903-7.

Rohrlich P S, Cardinaud S, Lule J, Montero-Julian F A, Prodhomme V, Firat H, Davignon J L, Perret E, Monseaux S, Necker A, Michelson S, Lemonnier F A, Charneau P, Davrinche C. Use of a lentiviral vector encoding a HCMV-chimeric IE1-pp65 protein for epitope identification in HLA-Transgenic mice and for ex vivo stimulation and expansion of CD8(+) cytotoxic T cells from human peripheral blood cells. Hum Immunol. 2004 May; 65(5):514-22.

Firat H, Zennou V, Garcia-Pons F, Ginhoux F, Cochet M, Danos O, Lemonnier F A, Langlade-Demoyen P, Charneau P. Use of a lentiviral flap vector for induction of CTL immunity against melanoma. Perspectives for immunotherapy. J Gene Med. 2002 January-February; 4(1):38-45.

Ayyoub M, Migliaccio M, Guillaume P, Lienard D, Cerottini J C, Romero P, Levy F, Speiser D E, Valmori D. Lack of tumor recognition by hTERT peptide 540-548-specific CD8(+) T cells from melanoma patients reveals inefficient antigen processing. Eur J Immunol. 2001 September; 31(9):2642-51.

Esslinger C, Chapatte L, Finke D, Miconnet I, Guillaume P, Levy F, MacDonald H R. In vivo administration of a lentiviral vaccine targets DCs and induces efficient CD8(+) T cell responses. J Clin Invest. 2003 June; 111 (11):1673-81.

Esslinger C, Romero P, MacDonald H R. Efficient transduction of dendritic cells and induction of a T-cell response by third-generation lentivectors. Hum Gene Ther. 2002 Jun. 10; 13(9):1091-100.

Parkhurst M R, Riley J P, Igarashi T, Li Y, Robbins P F, Rosenberg S A. Immunization of patients with the hTERT: 540-548 peptide induces peptide-reactive T lymphocytes that do not recognize tumors endogenously expressing telomerase. Clin Cancer Res. 2004 Jul. 15; 10(14):4688-98.

Firat H, Garcia-Pons F, Tourdot S, Pascolo S, Scardino A, Garcia Z, Michel M L, Jack R W, Jung G, Kosmatopoulos K, Mateo L, Suhrbier A, Lemonnier F A, Langlade-Demoyen P. H-2 class I knockout, HLA-A2.1-transgenic mice: a versatile animal model for preclinical evaluation of antitumor immunotherapeutic strategies. Eur J Immunol. 1999 October; 29(10):3112-21.

Frolkis M, Fischer M B, Wang Z, Lebkowski J S, Chiu C P, Majumdar A S. Dendritic cells reconstituted with human telomerase gene induce potent cytotoxic T-cell response against different types of tumors. Cancer Gene Ther. 2003 March; 10(3):239-49.

Vonderheide R H. Telomerase as a universal tumor-associated antigen for cancer immunotherapy. Oncogene. 2002 Jan. 21; 21(4):674-9. Review.

Sun B, Huang Q, Liu S, Chen M, Hawks C L, Wang L, Zhang C, Hornsby P J. Progressive loss of malignant behavior in telomerase-negative tumorigenic adrenocortical cells and restoration of tumorigenicity by human telomerase reverse transcriptase. Cancer Res. 2004 Sep. 1; 64(17):6144-51.

Tajima K, Ito Y, Demachi A, Nishida K, Akatsuka Y, Tsujimura K, Hida T, Morishima Y, Kuwano H, Mitsudomi T, Takahashi T, Kuzushima K. Interferon-gamma differentially regulates susceptibility of lung cancer cells to telomerase-specific cytotoxic T lymphocytes. Int J Cancer. 2004 Jun. 20; 110(3):403-12.

Su Z, Vieweg J, Weizer A Z, Dahm P, Yancey D, Turaga V, Higgins J, Boczkowski D, Gilboa E, Dannull J. Enhanced induction of telomerase-specific CD4(+) T cells using dendritic cells transfected with RNA encoding a chimeric gene product. Cancer Res. 2002 Sep. 1; 62(17):5041-8.

Heiser A, Maurice M A, Yancey D R, Coleman D M, Dahm P, Vieweg J. Human dendritic cells transfected with renal tumor RNA stimulate polyclonal T-cell responses against antigens expressed by primary and metastatic tumors. Cancer Res. 2001 Apr. 15; 61(8):3388-93.

Breckpot K, Dullaers M, Bonehill A, van Meirvenne S, Heirman C, de Greef C, van der Bruggen P, Thielemans K. Lentivirally transduced dendritic cells as a tool for cancer immunotherapy. J Gene Med. 2003 August; 5(8):654-67.

Espevik, T., and Nissen-Meyer, J. (1986). A highly sensitive cell line, WEHI 164 clone 13, for measuring cytotoxic factor/tumor necrosis factor from human monocytes. J Immunol Methods 95, 99-105.

Meyerson, M., Counter, C. M., Eaton, E. N., Ellisen, L. W., Steiner, P., Caddle, S. D., Ziaugra, L., Beijersbergen, R. L., Davidoff, M. J., Liu, Q., et al. (1997). hEST2, the putative human telomerase catalytic subunit gene, is up-regulated in tumor cells and during immortalization. Cell 90, 785-795.

Rohrlich, P. S., Cardinaud, S., Firat, H., Lamari, M., Briand, P., Escriou, N., and Lemonnier, F. A. (2003). HLA-B*0702 transgenic, H-2 KbDb double-knockout mice: phenotypical and functional characterization in response to influenza virus. Int Immunol 15, 765-772.

Sidney, J., Southwood, S., del Guercio, M. F., Grey, H. M., Chesnut, R. W., Kubo, R. T., and Sette, A. (1996). Specificity and degeneracy in peptide binding to HLA-B7-like class I molecules. J Immunol 157, 3480-3490.

The invention claimed is:

1. An isolated polynucleotide encoding a hTERT (human telomerase reverse transcriptase) epitope consisting of APRRLVQLL (SEQ ID NO: 17) (p444*).

2. An isolated polynucleotide according to claim 1, comprising at least the polynucleotidic unit gcccccgtcgcctggtgcagctgctc (SEQ ID NO: 32) (n444*).

3. An expression vector comprising a polynucleotide according to claim 1, or 2.

4. An isolated cell comprising a vector according to claim 3.

5. An isolated cell genetically transformed with a polynucleotide according to claim 1, or 2.

6. An isolated cell according to claim 4, which is an antigen presenting cell (APC).

7. An isolated cell according to claim 6 that is a dendritic cell (DC).

8. An isolated cell according to claim 7 that is an ex vivo maturated DC.

9. An isolated cell according to claim 4, which is a non-human mammal cell.

10. An isolated cell according to claim 4, which is an isolated human cell.

11. An isolated polypeptide encoded by a polynucleotide according to claim 1, or 2.

12. A composition comprising at least one component chosen from the group consisting of: a. a polynucleotide according to claim 1, or 2, or
   b. a vector according to claim 3, or,
   c. an isolated cell according to claim 4, and
   d. an isolated polypeptide according to claim 11.

* * * * *